United States Patent
Hariri et al.

(10) Patent No.: US 8,926,964 B2
(45) Date of Patent: Jan. 6, 2015

(54) METHODS OF GENERATING NATURAL KILLER CELLS

(75) Inventors: Robert J. Hariri, Bernardsville, NJ (US); Mohammad A. Heidaran, Chatham, NJ (US); Stephen Jasko, Rutherford, NJ (US); Lin Kang, Edison, NJ (US); Eric Law, East Brunswick, NJ (US); Ajai Pal, Bridgewater, NJ (US); Bhavani Stout, Lebanon, NJ (US); Vanessa Voskinarian-Berse, Millington, NJ (US); Andrew Zeitlin, Somerset, NJ (US); Xiaokui Zhang, Livingston, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 0 days.

(21) Appl. No.: 13/182,250

(22) Filed: Jul. 13, 2011

(65) Prior Publication Data

US 2012/0148553 A1    Jun. 14, 2012

Related U.S. Application Data

(60) Provisional application No. 61/363,981, filed on Jul. 13, 2010, provisional application No. 61/497,897, filed on Jun. 16, 2011.

(51) Int. Cl.
*A01N 63/00* (2006.01)
*C12N 5/00* (2006.01)
*C12N 5/0783* (2010.01)
*A61K 35/12* (2006.01)

(52) U.S. Cl.
CPC ...... *C12N 5/0646* (2013.01); *C12N 2501/2303* (2013.01); *C12N 2501/2302* (2013.01); *C12N 2501/91* (2013.01); *C12N 2501/145* (2013.01); *C12N 2500/36* (2013.01); *C12N 2500/46* (2013.01); *C12N 2501/59* (2013.01); *C12N 2501/2315* (2013.01); *C12N 2501/2307* (2013.01); *C12N 2501/26* (2013.01); *C12N 2500/33* (2013.01); *C12N 2500/25* (2013.01); *C12N 2501/998* (2013.01); *A61K 2035/124* (2013.01); *C12N 2501/125* (2013.01); *C12N 2500/38* (2013.01); *C12N 2500/05* (2013.01); *C12N 2500/44* (2013.01)
USPC ...................................... 424/93.71; 435/377

(58) Field of Classification Search
USPC ...................................... 424/93.71; 435/377
See application file for complete search history.

(56) References Cited

U.S. PATENT DOCUMENTS

| | | |
|---|---|---|
| 3,862,002 A | 1/1975 | Sanders |
| 4,798,824 A | 1/1989 | Belzer et al. |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,356,373 A | 10/1994 | Dracker et al. |
| 5,372,581 A | 12/1994 | Anderson |
| 5,415,665 A | 5/1995 | Hessel et al. |
| 5,436,151 A | 7/1995 | McGlave et al. |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,552,267 A | 9/1996 | Stern et al. |
| 5,580,777 A | 12/1996 | Bernard |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

Mrozek et al. (Role of interleukin-15 in the Development of Human CD56+ Natural Killer Cells From CD34+ Hematopoietic Progenitor Cells. 1996. Blood, 87(7): 2632-2640).*
van den Brink et al. (The Generation of Natural Killer (NK) Cells from NK Precursor Cells in Rat Long-Term Bone Marrow Cultures. J. Exp. Med (1990) 172:303-313).*
U.S. Appl. No. 13/013,721, filed Jan. 25, 2011, Zhang et al.
U.S. Appl. No. 13/081,415, filed Apr. 6, 2011, Abbot.
U.S. Appl. No. 13/081,422, filed Apr. 6, 2011, Edinger.
U.S. Appl. No. 13/089,029, filed Apr. 18, 2011, Hariri.
U.S. Appl. No. 13/107,727, filed May 13, 2011, Edinger et al.

(Continued)

*Primary Examiner* — Karen Cochrane Carlson
*Assistant Examiner* — Natalie Moss
(74) *Attorney, Agent, or Firm* — Jones Day

(57) ABSTRACT

Provided herein are methods of producing natural killer cells using a two-step expansion and differentiation method. Also provided herein are methods of suppressing tumor cell proliferation, of treating individuals having cancer or a viral infection, comprising administering the NK cells produced by the method to an individual having the cancer or viral infection.

26 Claims, 8 Drawing Sheets

(56) References Cited

U.S. PATENT DOCUMENTS

Figure 1:
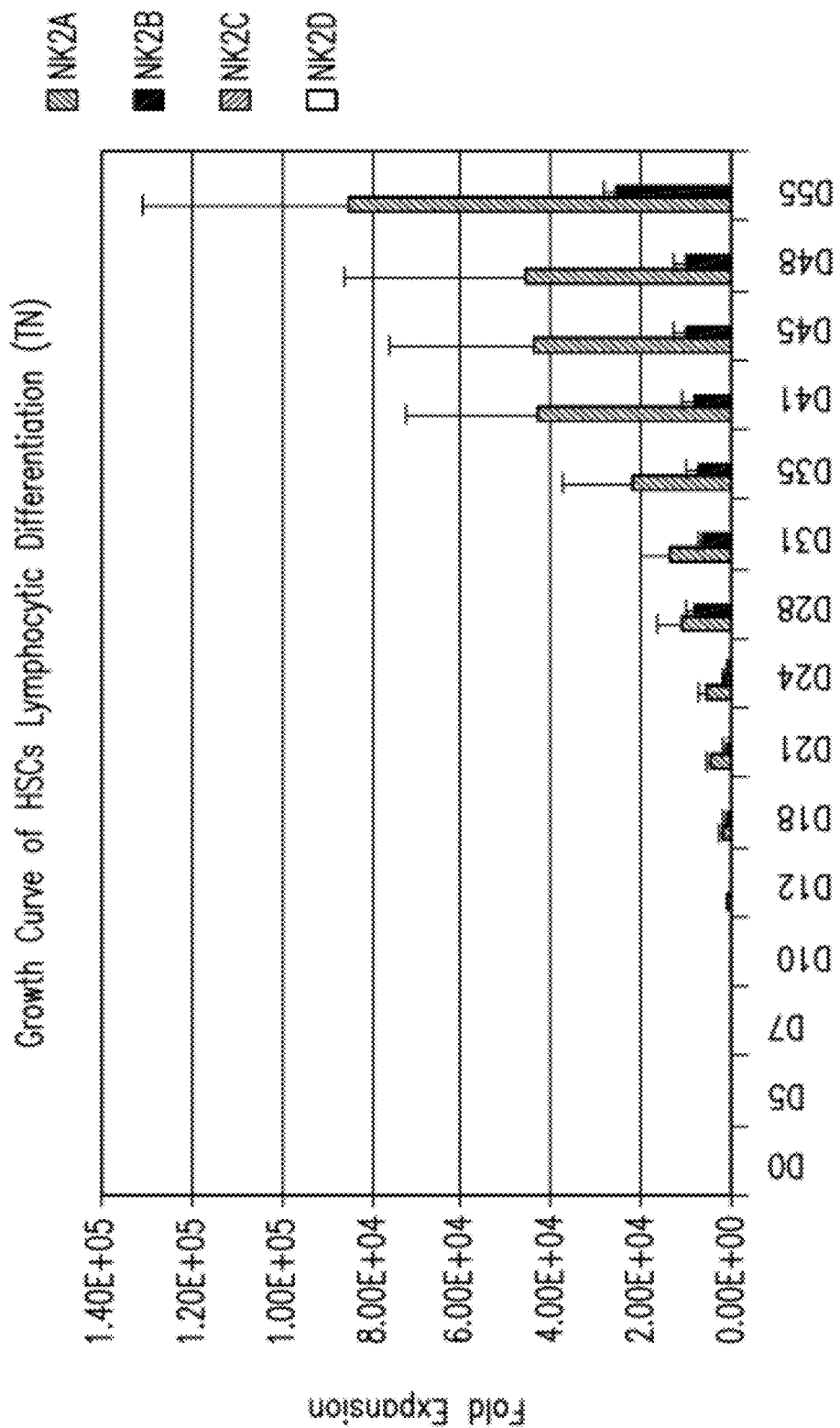

| | | | |
|---|---|---|---|
| 5,677,139 A | 10/1997 | Johnson |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,806,529 A | 9/1998 | Reisner et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,861,315 A | 1/1999 | Nakahata et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaille et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,102,871 A | 8/2000 | Coe |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswell |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,291,240 B1 | 9/2001 | Mansbridge et al. |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakamam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,497,875 B1 | 12/2002 | Sorrell et al. |
| 6,534,084 B1 | 3/2003 | Vyakamam et al. |
| 6,541,024 B1 | 4/2003 | Kadiyala et al. |
| 6,548,299 B1 | 4/2003 | Pykett |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,875,607 B1 | 4/2005 | Reubinoff et al. |
| 6,916,655 B2 | 7/2005 | Yasumoto et al. |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 8,202,703 B2 | 6/2012 | Edinger et al. |
| 8,263,065 B2 | 9/2012 | Zhang et al. |
| 2001/0005591 A1 | 6/2001 | Qasba et al. |
| 2001/0038836 A1 | 11/2001 | During et al. |
| 2002/0102239 A1 | 8/2002 | Koopmans |
| 2002/0123141 A1 | 9/2002 | Hariri |
| 2002/0132343 A1 | 9/2002 | Lum |
| 2002/0160510 A1 | 10/2002 | Hariri |
| 2003/0007954 A1 | 1/2003 | Naughton et al. |
| 2003/0032179 A1 | 2/2003 | Hariri |
| 2003/0044976 A1 | 3/2003 | Dominko et al. |
| 2003/0044977 A1 | 3/2003 | Sakuragawa et al. |
| 2003/0045552 A1 | 3/2003 | Robarge et al. |
| 2003/0068306 A1 | 4/2003 | Dilbert Mehmet |
| 2003/0096841 A1 | 5/2003 | Robarge et al. |

(56) References Cited

U.S. PATENT DOCUMENTS

| | | |
|---|---|---|
| 2003/0161818 A1 | 8/2003 | Weiss et al. |
| 2003/0180269 A1 | 9/2003 | Hariri |
| 2003/0187515 A1 | 10/2003 | Hariri |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0084815 A1 | 4/2006 | Muller et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0060616 A1 | 3/2007 | Bennett et al. |
| 2007/0092497 A1 | 4/2007 | Hariri |
| 2007/0092967 A1 | 4/2007 | Han et al. |
| 2007/0116682 A1 | 5/2007 | Atala et al. |
| 2007/0122903 A1 | 5/2007 | Rezania et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0224174 A1* | 9/2007 | Kang et al. .................. 424/93.7 |
| 2007/0253931 A1 | 11/2007 | Varney et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2009/0004150 A1 | 1/2009 | Schwartz-Albiez et al. |
| 2009/0017539 A1 | 1/2009 | Spanholtz |
| 2009/0053805 A1 | 2/2009 | Hariri |
| 2009/0104164 A1 | 4/2009 | Zhang et al. |
| 2009/0123442 A1 | 5/2009 | Dilber et al. |
| 2009/0126482 A1 | 5/2009 | Heidaran et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2009/0263361 A1 | 10/2009 | Lee et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0178275 A1 | 7/2010 | Spanholtz |
| 2010/0183571 A1 | 7/2010 | Paludan et al. |
| 2010/0216181 A1* | 8/2010 | Daigh et al. ................... 435/29 |
| 2010/0260847 A1 | 10/2010 | Hariri |
| 2010/0285586 A1* | 11/2010 | Timmins et al. ............... 435/377 |
| 2010/0291679 A1 | 11/2010 | Edinger et al. |
| 2010/0297689 A1 | 11/2010 | Edinger et al. |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |

(56) References Cited

U.S. PATENT DOCUMENTS

| | | |
|---|---|---|
| 2012/0122215 A1 | 5/2012 | Edinger et al. |
| 2012/0156782 A1 | 6/2012 | Tryggvason et al. |
| 2012/0171161 A1 | 7/2012 | Abramson et al. |
| 2012/0171295 A1 | 7/2012 | Abramson et al. |
| 2012/0230959 A1 | 9/2012 | Abbot et al. |
| 2012/0328583 A1 | 12/2012 | Herzberg et al. |
| 2013/0022581 A1 | 1/2013 | Edinger et al. |
| 2013/0028871 A1 | 1/2013 | Edinger et al. |
| 2013/0071362 A1 | 3/2013 | Bhatia et al. |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1288293 A1 | 3/2003 |
| EP | 1384775 A1 | 1/2004 |
| EP | 1405649 | 4/2004 |
| EP | 1535994 | 6/2005 |
| EP | 1775341 | 4/2007 |
| EP | 2411507 | 2/2012 |
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06666 | 5/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 97/18298 | 5/1997 |
| WO | WO 98/37903 | 9/1998 |
| WO | WO 99/03973 | 1/1999 |
| WO | WO 99/64566 | 12/1999 |
| WO | WO 00/17325 | 3/2000 |
| WO | WO 00/27999 | 5/2000 |
| WO | WO 00/38762 | 7/2000 |
| WO | WO 00/73421 | 12/2000 |
| WO | WO 01/93909 | 12/2001 |
| WO | WO 02/46373 | 6/2002 |
| WO | WO 02/063962 | 8/2002 |
| WO | WO 02/064755 | 8/2002 |
| WO | WO 03/042405 | 5/2003 |
| WO | WO 03/068937 | 8/2003 |
| WO | WO 03/086373 | 10/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/095584 | 6/2005 |
| WO | WO 2005/055929 | 10/2005 |
| WO | WO 2005/097190 | 10/2005 |
| WO | WO 2005/105992 | 11/2005 |
| WO | WO 2006/015214 | 2/2006 |
| WO | WO 2006/111706 | 10/2006 |
| WO | WO 2007/011693 | 1/2007 |
| WO | WO 2007/024441 | 3/2007 |
| WO | WO 2007/037682 | 4/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/073552 | 6/2007 |
| WO | WO 2007/076522 | 7/2007 |
| WO | WO 2007/079183 | 7/2007 |
| WO | WO 2007/087293 | 8/2007 |
| WO | WO 2008/019148 | 2/2008 |
| WO | WO 2008/051568 | 5/2008 |
| WO | WO 2008/060541 | 5/2008 |
| WO | WO 2008/100497 | 8/2008 |
| WO | WO 2008/118020 | 10/2008 |
| WO | WO 2009/045360 | 4/2009 |
| WO | WO 2010/013947 | 2/2010 |
| WO | WO 2010/027094 | 3/2010 |
| WO | WO 2010/110734 | 9/2010 |
| WO | WO 2010/111631 | 9/2010 |
| WO | WO 2012/009422 | 1/2012 |
| WO | WO 2012/075412 | 6/2012 |

OTHER PUBLICATIONS

U.S. Appl. No. 13/107,778, filed May 13, 2011, Edinger et al.
U.S. Appl. No. 13/108,871, filed May 16, 2011, Hariri.
U.S. Appl. No. 13/108,891, filed May 16, 2011, Hariri.
U.S. Appl. No. 13/108,901, filed May 16, 2011, Hariri.
U.S. Appl. No. 13/584,612, filed Aug. 13, 2012, Hariri et al.
U.S. Appl. No. 13/650,803, filed Oct. 12, 2012, Heidaran et al.
U.S. Appl. No. 13/711,331, filed Dec. 11, 2012, Hariri et al.
U.S. Appl. No. 13/727,217, filed Dec. 26, 2012, Hariri et al.
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).
Addison, et al., "Metabolism of Prednisolone by the Isolated Perfused Human Placental Lobule," J. Ster. Biochem. Mol. Biol., 39(1):83-90 (1991).
Aggarwal, et al., "Human Mesenchymal Stem Cells Modulate Allogeneic Immune Cell Responses," Blood 105(4):1815-22 (2005).
Alici et al., "Autologous antitumor activity by NK cells expanded from myeloma patirents using GMP-compliant components," Blood 111:3155-3162 (2008).
Alici et al., "Anti-myeloma activity of endogenous and adoptively transferred activated natural killer cells in experimental multiple myeloma model," Exp Hematol. 35(12):1839-46 (2007).
Allikmets et al., "A human placenta specific ATP binding cassette gene (ABCP) on chromosome 4q22 that is involved in multidrug resistance," Cancer Res. 58(23):5337-5339 (1998).
Anker In't P, et al., "Isolation of Mesenchymal Stem Cells of Fetal or Maternal Origin from Human Placenta," Stem Cells; 22:1338-45 (2004).
Aplin, "Implantation, trophoblast Differentiation and Haemochorial Placentation: Mechanistic Evidence in vivo and in vitro," Journal of Cell Science 99:681-692 (1991).
Ashihara, et al., "Successful Peripheral Blood Stem Cell Transplantation for Myelodysplastic Syndrome," Bone Marrow Transplantation 24(12): 1343-1345 (1999).
Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barkholt et al., "Resetting the immune system in refractory Crohn's disease: is autologous hematopoietic stem cell transplantation the way forward?" Immunotherapy. Sep. 2009;1(5):753-64.
Barlow et al., "Comparison of Human Placenta- and Bone Marrow-Derived Multipotent Mesenchymal Stem Cells," Stem Cells and Development 17:1095-1108 (2008).
Barry et al., "The Monoclonal Antibody SH-2, Raised Against Human Mesenchymal Stem Cells, Recognizes an Epitope on Endoglin (CD105)," Osiris Therapeutics Inc., (2001) Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Battula et al., "Prospective Isolation and Characterization of Mesenchymal Stem Cells from Human Placenta Using a Firzzled-9-Specific Monoclonal Antibody," Differentiation 76:326-336 (2008).
Belvedere, et al., "Increased Blood Volume and CD34(+)CD38(−) Progenitor Cell Recovery Using a Novel Umbilical Cord Blood Collection System," Stem Cells 18(4):245-251 (2000).

(56) References Cited

OTHER PUBLICATIONS

Bloxam et al., "Culture of Syncytiotrophoblast for the Study of Human Placental Transfer. Part I: Isolation and Purification of Cytotrophoblast,"Placenta 18:93-98 (1997).

Bloxam, "Human Placental Trophoblast Culture: One-Sided and Two-Sided Models," Proceedings of the Nutrition Society 50:349-354 (1991).

Bossolasco et al., "Molecular and phenotypic characterization of human amniotic fluid cells and their differentiation potential," Cell Research 16:329-336 (2006).

Bullen et al., "Two-Sided Culture of Human Placental Trophoblast. Morphology, Immunocytochemistry and Permeability Properties," Placenta 11:431-450 (1990).

Campagnoli, et al., "Identification of Mesenchymal Stem/Progenitor Cells in Human First-Trimester Fetal Blood, Liver, and Bone Marrow." Blood 98(8):2396-402 (2001).

Caniggia et al., "Oxygen and Placental Development During the First Trimester: Implications for the Pathophysiology of Pre-Eclampsia," PubMed, Placenta 21(Suppl A):S25-30 (2000).

Caplan, "The Mesengenic Process," Clin. Plast. Surg. 21(3):429-435 (1994).

Carayol et al., "NK Cells Differentiated from Bone Marrow, Cord Blood and Peripheral Blood Stem Cells Exhibit Similar Phenotype and Functions," European Journal of Immunology 28(6):1991-2002 (1998).

Carlens et al., "A new method for in vitro expansion of cytotoxic human CD3-CD56+ natural killer cells," Hum Immunol. 62(10):1092-8 (2001).

Carter, et al., "Characterization of MSC Potential to Treat GVHD Using Molecular Markers Linked to MSC-Mediated Immunosuppression in Vitro," Blood, 106(11) part 2, Abstract No. 4322,160B (2005).

Cester et al., "Cation Transport Across Cultured Trophoblast Membrane in Preeclampsia," Clin. And Exper. Hyper. In Pregnancy, B11(1):59-69 (1992).

Chang, et al., "Placenta-Derived Multipotent Cells Exhibit Immunosuppressive Properties That Are Enhanced in the Presence of Interferon-gamma," Stem Cells 24:2466-2477 (2006).

Chao, et al., "Stem Cell Transplantation (Cord Blood Transplants)." American Society of Hematology p. 354-371 (2004).

Chen, et al. "Intravaneous Administration of Human Umbilical Cord Reduces Behavioral Deficits after Stroke in Rats," Stroke 32(11): 2682-2688 (2001).

Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).

Chen, et al., "Therapeutic Benefit of Intravenous Administration of Bone Marrow Stromal Cells after Cerebral Ischemia in Rats," Stroke, 32(4):1005-11 (2001).

Chies et al., "Sickle Cell Disease: A Chronic Inflammatory Condition," Medical Hypotheses 57(1):46-50 (2001).

Chin, et al., "Enhanced Interferon Production and Lymphokine-Activated Cytotoxicity of Human Placental Cells," Cellular Immunology 113:1-9 (1988).

Clark, et al., "Placental Trophoblast from Successful Human Pregnancies Expresses the Tolerance Signaling Molecule, CD200 (OX-2)" Am. J. Reprod. Immunol., 50(3):187-195 (2003).

Contractor, et al., "A comparison of the effects of different perfusion regimens on the structure of the isolated human placental lobule," Cell Tissue Res. 237:609-617 (1984).

Cosma, et al., "Use and Application of Stem Cells in Toxicology," SOT Annual Meeting, p. 4, Abstract 19 (2003).

Cotte et al., "Preparation of Highly Purified Cytotrophoblast from Human Placenta with Subsequent Modulation to Form Syncytiotrophoblast in Monolayer Cultures," In Vitro 16(8):639-646 (1980).

Czarneski, et al., "Effects of Cord Blood Transfer on the Hematopoietic Recovery Following Sublethal Irradiation in MRL 1pr/1pr Mice," Proc. Soc. Exp. Biol. Med. 220(2):79-87 (1999).

Database WPI Week 200357 Derwent Publications Ltd., London, GB, AN 2003-59905 & CN 1 407 888 A (Zhou S) Apr. 2, 2003 (2003).

Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).

Davies, et al. "Thalidomide and Immunomodulatory Derivatives Augment Natural Killer Cell Cytotoxicity in Multiple Myeloma," Blood 98(1):210-216 (2001).

Davies, et al., "Engraftment and Survival After Unrelated-Donor Bone Marrow Transplantation: A Report from the National Marrow Donor Program," Blood; 96(13): 4096-4102 (2000).

Davila, et al., "Use and Application of Stem Cells in Toxicology," Toxicological Sciences 79:214-223 (2004).

De Coppi, , et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81 (2004).

De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93 (2002).

De Coppi, et al., "Human fetal stem cell isolation from amniotic fluid for tissue reconstruction," J. Urology 167(4 Supp.) 85 (Abstract 338) (2002).

De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7 (2005).

De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).

Dezell et al., Natural killer cell differentiation from hematopoietic stem cells: a comparative analysis of heparin- and stromal cell-supported methods. Biol Blood Marrow Transplant. 18(4):536-45. Epub Dec. 7, 2011. (2012).

Dominici, et al., "Minimal Criteria for Defining Multipotent Mesenchymal Stromal Cells. The International Society for Cellular Therapy Position Statement," Cytotherapy 8(4):315-317 (2006).

Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).

Dushnik-Levinson, et al. "Embryogenesis in vitro: study of differentiation of embryonic stem cells." Biol Neonate. 67(2):77-83 (1995).

Eissens et al., Defining early human NK cell developmental stages in primary and secondary lymphoid tissues. PLoS One. 2012;7(2):e30930.Epub Feb. 3, 2012.

Elchalal, et al., "Postpartum Umbilical Cord Blood Collection for Transplantation: a Comparison of Three Methods," Am. J. of Obstetrics & Gyn. 182(1 Pt 1):227-232 (2000).

Ende, "Berashis Cells in Human Umbilical Cord Blood Vs. Embryonic Stem Cells," J. Med. 33(14):167-171 (2002).

Ende, "Collection of Umbilical Cord Blood for Transplantation," Blood 80(6):1623-1624 (1992).

Ende, "The Feasibility of Using Blood Bank Stored (4° C) Cord Blood, Unmatched for HLA for Marrow Transplantation," Am. J. Clin. Pathol. 111:773-781 (1999).

Ende, et al., "Human Umbilical Cord Blood Cells Amerliorate Alzheimer's Disease in Transgenic Mice," J. Med. 32(3-4):241-7 (2001).

Ende, et al., "Human Umbilical Cord Blood Cells Ameliorate Huntington's Disease in Transgenic Mice," J. Med. 32(3-4):231-240 (2001).

Ende, et al., "Human Umbilical Cord Blood Effect on SOD Mice (Amyotrophic Lateral Sclerosis)," Life Sci. 67(1):53-59 (2001).

Ende, et al., "Parkinson's Disease Mice and Human Umbilical Cord Blood," Journal of Medicine 33(1-4):173-180 (2002).

Ende, et al., "Pooled Umbilical Cord Blood as a Possible Universal Donor for Marrow Reconstitution and Use in Nuclear Accidents," Life Sci. 69:1531-1539 (2001).

(56) References Cited

OTHER PUBLICATIONS

Ende, et al., "The Effect of Human Cord Blood on SJL/J Mice After Chemoablation and Irradiation and Its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Esser et al., NK cells engineered to express a GD2-specific antigen receptor display built-in ADCC-like activity against tumour cells of neuroectodermal origin. J Cell Mol Med. 16(3):569-81 (2012).
Evans, "Stem Cell Therapy: Moving towards Reality," Am. J. Obstet. Gynecol. 194:662-663 (2006).
Fasouliotis, et al., "Human umbilical cord blood banking and transplantation: a state of the art," Eur. J. Obstet. Gynecol. Reprod. Biol. 90(1):13-25 (2000).
Fauriat et al., "Deficient expression of NCR in NK cells from acute myeloid leukemia: evolution during leukemia treatment and impact of leukemia cells in NCRdull phenotype induction," Blood 109: 323-330 (2007).
Ferlazzo et al, PNAS USA 101(47):16606-11 (2004).
Fisher et al., "Adhesive and Degradatie Properties of Human Placental Cytotrophoblast Cells In Vitro," Journal od Cell Biology 109:891-902 (1989).
Frank H G, et al., "Cell culture models of human trophoblast: primary culture of trophoblast—a workshop report." Placent Apr. 2001, vol. 22 Suppl A, pp. S107-S109, XP002443188 ISSN: 0143-4004 (2001).
Freud et al., "Evidence for Discrete Stages of Human Natural Killer Cell Differentiation In Vivo," Journal of Eperimental Medicine 203(4):1035 (2006).
Garcia-Olmo et al., "Autologous Stem Cell Transplantation for Treatment of Rectovaginal Fistula in Perianal Crohn's Disease: A New Cell-based Therapy", Int. J. Colorectal Dis. 18:451-454 (2003).
Genbacev et al., "Regulation of Human Placental Development by Oxygen Tension," 277(5332):1669-1672 (1997).
Gluckman, et al., "Cord Blood Heamatopoietic Stem Cells: Biology and Transplantation," In: Hematology, American Society of Hematology Education Program Book p. 1-14 (1998).
Gluckman, et al., "Results of Unrelated Umbilical Cord Blood Hematipoeietic Stem Cell Transplant," Transfusion Cinique et Biologique 8(3):146-154 (2001).
Greenwood et al., "Membrane Potential Difference and Intracellular Cation Concentrations in Human Placental Trophoblast Cells in Culture," Journal of Physiology 492.3:629-640 (1996).
Guimaraes et al., "Evaluation of ex vivo expanded human NK cells on antileukemia activity in SCID-beige mice," Leukemia. 20(5):833-9 (2006).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos, et al. "Isolation and characterization of endothelial progenitor cells from mouse embryos," Development. 125(8):1457-68 (1998).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.
Herrera, et al., "Mesenchymal Stem Cells Contribute to the Renal Repair of Acute Tubular Epithelial Injury,"• Int. J. Mol. Med.: 14(6):1035-41 (2004).

Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirano et al., "CD9 is Expressied in Extravillous Trophoblasts in Association with Integrin α3 and integrin α5," Molecular Human Reproduction 5(2):162-167 (1999).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075 (2000).
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells,"• Biochemical and Biophysical Research Communications; 362:347-53 (2007).
Huss, "Isolation of Primary and Immortalized CD34-Hematopoietic and Mesenchymal Stem Cells from Various Sources," Stem Cells 18:1-9 (2000).
Huss, "Perspectives on the Morphology and Biology of CD34-Negative Stem Cells," J. Hematother. Stem. Cell Res. 9(6):783-793 (2000).
Igura, et al., "Isolation and Characterization of Mesencymal Progenitor Cells from Chorionic Villi of Human Placenta," Cytotherapy 6(6): 543-553 (2004).
Imai et al., Genetic modification of T cells for cancer therapy. J Biol Regul Homeost Agents. Jan.-Mar.;18(1):62-71 (2004).
Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
International Preliminary Report on Patentability from PCT/US2006/049491 dated Jan. 14, 2008 (2008).
International Search Report and Written Opinion from PCT/US2006/049491 dated Sep. 26, 2007 (2007).
Iwasaki, "Recent Advances in the Treatment of Graft-Versus-Host Disease,"• Clin. Med. Res.; 2(4):243-52 (2004).
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2000).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in the Human Placenta," Trophoblast Research 10:21-65 (1997).
Kawata, et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Kliman et al., "Purification, Characterization, and In Vitro Differentiation of Cytotropholblasts from Human Term Placentae," Endocrinology 118(4):1567-1582 (1986).

(56) References Cited

OTHER PUBLICATIONS

Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81 (2004).
Korbling, et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Surce of Hmatopoietic Sem Cells for Transplantation into Unrelated Recipients," N. Engl. J. Med. 335:157-166 (1996).
Landon et al., "The Effects of Ethanol Methotrexate and Diphenylhydantoin on [$^{14}$C] Leucine Incorporation by Human Trophoblasst Cells Cultured In Vitro," British Journal of Obstetrics and Gynaecology 94:252-255 (1987).
Law, E., et al., "Enhanced ex vivo expansion of cord blood CD34+ cells by novel immunomodulatory agents (IMiD)," Stem Cell Symposium, State of New Jersey Commission on Science & Technology (Abstract) (2005).
Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).
Le Blanc, et al., "Treatment of Severe Acute Graft-Versus-Host Disease With Third Party Haploidentical Mesenchvmal Stem Cells,"• Lancet; 363(9419):1439-41 (2004).
Lebkowski, et al., "Serum and Plasma Levels of FGF-2 and VEGF in Healthy Blood Donors," Cancer J. 7(Suppl 2):S83-S93 (2001).
Lee-Macary et al, J Immunol Methods 252(1-2):83-92 (2001).
Lehmann et al., Ex Vivo Generated Natural Killer Cells Acquire Typical Natural Killer Receptors and Display a Cytotoxic Gene Expression Profile Similar to Peripheral Blood Natural Killer Cells. Stem Cells Dev. 21(16):2926-2938 (2012).
Leonard, et al., "The Role of ABC Transporters in Clinical Practice," Oncologist. 8:411-424 (2003).
Li, et al., "Mesenchymal Stem Cells Derived from Human Placenta Suppress Allogenic Umbilical Cord Blood Lymphocyte Proliferation." Cell Res. 15: 539-547 (2005).
Lin, et al. "Murine CD200(+)CK7(+) trophoblasts in a poly (I:C)-induced embryo resorption model." Reproduction (Cambridge), vol. 130, No. 4, Oct. 2005, pp. 529-537, XP002443406 ISSN: 1470-1626 (2005).
Lipinski et al., "Human Trophoblast Cell-Surface Antigen Defined by Monoclonal Antibodies," Proc. Natl. Acad. Sci. USA, Medical Sciences 78(8):5147-5150 (1981).
Loke et al., "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Luedke et al., Cetuximab therapy in head and neck cancer: Immune modulation with interleukin-12 and other natural killer cell-activating cytokines. Surgery. Jul. 6, 2012.
Ma, et al., "Development of an in vitro Human Placenta Model by the Cultivation of Human Trophoblasts in a Fiber-Based Bioreactor System," Tissue Engineering 5, 91-102 (1999).
Ma, et al., "Human Umbilical Cord Wharton's Jelly-Derived Mesenchymal Stem Cells Differentiation into Nerve-Like Cells," Chinese Med. Jour., 118(23):1987-93 (2005).
Mackay, et al., "Chondrogenic Differentiation of Cultured Human Mesenchymal Stem Cells from Marrow," Tissue Engineering; 4(4):415-28 (1998).
Malmberg et al., "NK cell-mediated targeting of human cancer and possibilities for new means of immunotherapy," Cancer Immunol Immunother. 57(10):1541-52 (2008).
McMaster et al, "Human Placental HLA-G Expression is Restricted to Differentiated Cytotrophoblasts," J. Immunol. 154(8):3771-3778 (1995).
Melchner, et al., "Human Placental Conditioned Medium Reverses Apparent Commitment to Differentiation of Human Promyelocytic Leukemia Cells (HL60)," Blood 66(6):1469-1472 (1985).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki, et al., "Isolation of Multipotent Stem Cells from Placenta." AASLD Abstracts, Hepatology, Oct. 2003, Abstract 279, p. 290A (2003).
Miki, et al., "Production of Hepatocytes from Human Amniotic Stem Cells." Hepatology, Abstract 20, vol. 36, No. 4, Pt. 2 (2002).
Miki, et al., "Stem Cell Characteristics of Amniotic Epithelial Cells." Stem Cells Express, published online Aug. 9, 2005; doi:10. 1634/stemcells.2004-0357 (2005).
Miller et al., "Successful adoptive transfer and in vivo expansion of human haploidentical NK cells in patients with cancer," Blood 105:3051-3057 (2005).
Minguell, et al., "Mesenchymal Stem Cells," Exp. Biol. Med. 226:507-520 (2001).
Moore, et al., "A Simple Perfusion Technique for Isolation of Maternal Intervillous Blood Mononuclear Cells from Human Placentae," J. Immunol. Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Morgan et al., "Human Placental Cell Culture," Biochemical Society Transactions 12: 317-318 (1984).
Morgan et al., "Long-Term Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol.; 15(7):1794-1804 (2004).
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood; 99(11):4200-06 (2002).
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Muhlemann, et al., "Cytomegalovirus in the Perfused Human Term Placenta in vitro," Placenta 16:367-373 (1995).
Müller et al., Expression of a CD20-specific chimeric antigen receptor enhances cytotoxic activity of NK cells and overcomes NK-resistance of lymphoma and leukemia cells. Cancer Immunol Immunother. 57(3):411-23 (2008).
Myllynen "In Search of Models for Hepatic and Placental Pharmacokinetics," [Dissertation] University of Oulu, (2003).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int.; 70(1):121-29 (2006).
Nishishita, et al., "A Potential Pro-Angiogenic Cell Therapy with Human Placenta-Derived Mesenchymal Cells," Biochem. Biophys. Res. Commun. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Notice of Opposition by Farmindustria S.A. to corresponding claims filed in Peru; English translation Jan. 18, 2008 (2008).
Oda et al., "Trophoblast Stem Cells," Methods in Enxymology 419(15):387-400 (2006).

(56) References Cited

OTHER PUBLICATIONS

Paludan, et al., "Immune Suppression by Placenta Derived Adherent Cells (PDAC) Correlate with Monocyte Chemoattractant Protein-1 and IL-2 Secretion," Blood 108 (abstract only) 48B (2006).
Paludan, et al., "Placental Derived Stem Cells (PDAC) Suppress the Allo-MLR and the EBV Regression Assay," http://www.call4abstract.com/hem/finalpreview.php?absnum=552996 (2006).
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci, et al., "Comparison of Gene Expression of Umbilical Cord Vein and Bone Marrow-Derived Mesenchymal Stem Cells," Stem Cells; 22(7):1263-78 (2004).
Papaioannou, et al., "Stem Cells from Early Mammalian Embryos" Stem Cells Handbook:19-31 (2004).
Pegram et al., Adoptive transfer of gene-modified primary NK cells can specifically inhibit tumor progression in vivo. J Immunol. 181(5):3449-55 (2008).
Pellegrini, et al., "FADD and Caspase-8 Are Required for Cytokine-Induced Proliferation of Hemopoietic Progenitor Cells," Blood 106(5):1581-1589 (2005).
Pende et al., "Analysis of the receptor-ligand interaction in the natural killer-mediated lysis of freshly isolated myeloid or lymphoblastic leukemias: evidence for the involvement of the poliovirus receptor (CD155) and Nectin-2 (CD112)," Blood 105: 2066-2073 (2004).
Pera, et al., "Human Embryonic Stem Cells," J. Cell. Sci. 113:5-10 (2000).
Petroff et al., "Isolation and Culture of Term Human Trophoblast Cells," Methods in Molecular Medicine, Placenta and Trophoblast, 1(16):203-217 (2006).
Pinho et al., "Ex vivo differentiation of natural killer cells from human umbilical cord blood CD34+ progenitor cells," Cell Commun Adhes 18(3):45-55. Epub Sep. 12, 2011. (2011).
Pinho et al., "Genetic regulation of ex vivo differentiated natural killer cells from human umbilical cord blood CD34+ cells," J Recept Signal Transduct Res. Jul. 4, 2012, published online.
Pittenger., et al. "Multilineage Potential of Adult Human Mesenchymal Stem Cells." Science 284(5411):143-147 (1999).
Portmann-Lanz, et al., "Placental Mesenchymal Stem Cells as Potential Autologous Graft for Pre- and Perinatal Neuroregeneration" Am. J. Obstet Gynecol. 194:664-673 (2006).
Potgens et al., "Human Trophoblast Contains an Intracellular Protein Reactive with and Antibody against CD133—A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured; 38(Supp. 4):S23-33 (2007).
Quinn et al., "Mouse Trophoblast Stem Cells," Methods in Molecular Medicine 121(1):125-148 (2005).
Rachmilewitz et al., "Intermediate Cells During Cytotrphoblast Differentiation in Vitro," Cell Growth & Differentiation 4:395-402 (1993).
Reyes, et al., "Purification and ex vivo Expansion of Postnatal Human Marrow Mesodermanl Progenitor Cells," Blood 98(9):2615-2625 (2001).
Reyes, et al., Origin of endothelial progenitors in human postnatal bone marrow.J Clin Invest. 109(3):337-46 (2002).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Ringler et al., "In Vitro Systems for the Study of Human Placental Endocrine Function," Endocrine Reviews 11(1):105-123 (1990).
Rong-Hao et al., "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Roussev et al., "Phenotypic Characterization of Normal Human Placental Mononuclear Cells", Journal of Reproductive Immunology, Elsevier Science Ireland Ltd., IE, vol. 25, No. 1, pp. 15-29 (Sep. 1993).
Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Rubnitz et al, 2010, NKAML: A Pilot Study to Determine the Safety and Feasibility of Haploidentical Natural Killer Cell Transplantation in Childhood Acute Myeloid Leukemia, J. Clin Oncol 28, published ahead of print on Jan. 19, 2010 as 10.1200/JCO.2009.24.4590.
Ruggeri et al., "Effectiveness of donor natural killer cell alloreactivity in mismatched hematopoietic transplants," Science 295:2097-2100 (2002).
Russo, "Fighting Darwin's Battles. Symposium Marks Evolutionist Victory, Anti-Evolution Growth" The Scientist 15:6 (2001).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Sapin, "Esterification of Vitamin A by the Human Placenta Involves Villous Mesenchymal Fibrlboasts," pediatric Research 48(4):565-572 (2000).
Saric et al., "An IFN-γ-induced Aminopeptidase in the ER, ERAP I, Trims Precursors to MHC Class I-presented Peptides," Nature Immunology 3(12):1169-1176 (2002).
Schulz et al., "Human Embryonic Stem Cells as Models for Trophoblast Differentiation," Placenta 29(SupplA): S10-S16 (2008).
Schutz, et al., "Isolation and Cultivation of Endothelial Cells Derived from Human Placenta," Eur. J. Cell Biol. 395-401 (1996).
Schwab, "Fast and Reliable Culture Method for Cells from 8-10 Week Trophoblast Tissue," Lancet 323:1082 (1984).
ScienCell—Human Amniotic Epithelial Cells. http://www.sciencellonline.com/products/7100.htm.
Shamblott, et al., "Derivation of Pluripotent Stem Cells from Cultured Human Primordial Germ Cells," Proc. Natl. Acad. Sci. USA 95(23):13726-13731 (1998).
Sherley, "Asymmetric Cell Kinetics Genes: The Key to Expansion of Adult Stem Cells in Culture", Stem Cell 20:561-72 (2002).
Shook et al., Natural killer cell engineering for cellular therapy of cancer. Tissue Antigens. Dec;78(6):409-15 (2011).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sikkema-Raddatz, "Four Years' Cytogenetic Experience with the Culture of Chorionic Villi," Prenatal Diagnosis 20:950-955 (2000).
Sirchia, et al., "Placental/Umbilical Cord Blood Transplantation," Haematologica 84:738-747 (1999).
Slager, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).
Southard et al., "Important contents of the UW solution," Transplantation 49(2):251-257 (1990).
Spanholtz et al., High log-scale expansion of functional human natural killer cells from umbilical cord blood CD34-positive cells for adoptive cancer immunotherapy. PLoS One Feb. 15;5(2):e9221 (2010).
Spanholtz et al., Clinical-grade generation of active NK cells from cord blood hematopoietic progenitor cells for immunotherapy using a closed-system culture process. PLoS One 6(6):e20740. Epub Jun. 16, 2011. (2011).
Stanworth, et al., "Stem Cells: Progress in Research and Edging towards the Clinical Setting," Clin. Med. 1(5):378-382 (2001).

(56) References Cited

OTHER PUBLICATIONS

Stromberg et al., "Isolation of Functional Human Trophoblast Cells and Their Partial Characterization in Primary Cell Culture," In Vitro 14(7):6331-638 (1978).
Sunderland et al., "HLA A, B, C Antigens Are Expressed on Nonvillous Trophoblast of the Early Human Placenta," Journal of Immunology 127(6):2614-2615 (1981).
Tabiasco, et al., "Human decidual NK cells: Unique phenotype and functional properties—a review," Placenta, W.B. Saunders, 27:34-39 (2006).
Takahashi et al., "Induction fo CD16(+) CD56(bright) NK cells with antitumour cytotoxicity not only from CD16(−) CD56(bright) NK cells but also from CD16(−) CD56(dim) NK cells", Scandinavian Journal of Immunology, pp. 126-138, XP002528954 (2007).
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-7 (1998).
Toma, et al., "Human Mesenchymal Stem Cells Differentiate to a Cardiomyocyte Phenotype in the Adult Murine Heart," Circulation; 105:93-98 (2002).
Triulzi et al., Antibody-dependent natural killer cell-mediated cytotoxicity engendered by a kinase-inactive human HER2 adenovirus-based vaccination mediates resistance to breast tumors. Cancer Res. Oct. 1;70(19):7431-41 (2010).
Truman et al., "Human Placental Cytotrophoblast Cells: Identification and Culture," Arch Gynecol. Obstet. 246:39-49 (1989).
Truman et al., "The Effects of Substrate and Epidermal Growth Factor on Human Placental Trophoblast Cells in Culture," In Vitro Cellular & Developmental Biology 22(9):525-528 (1986).
Turner, et al., "A modified Harvest Technique for Cord Blood Hematopoietic Stem Cells," Bone Marrow Transplantation 10:89-91 (1992).
Ulloa-Montoya, et al., "Culture Systems for Pluripotent Stem Cells," Journal of Bioscience and Bioengineering; 100(1):12-27 (2005).
Verneris et al., 2010, Natural Killer Cell Consolidation for Acute Myelogeous Leukemia: A Cel Therapy Ready for Prime Time?, J Clin Oncol, vol. 28, 2010, published ahead of print on Jan. 19, 2010 as 10.1200/JCO.2009.26.4002.
Viacord, Umblicical cord blood can save lives (Informational brochure), Boston: ViaCell CENTR-BRO R1 Oct. 2001 (2001).
Wang, et al., "Enhanced Recovery of Hematopoietic Progenitor and Stem Cells from Cultivated, Postpartum Human Placenta," Blood 98(11/1):183a Abstract No. 769 (2001).
Wang, et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Watanabe, et al, "Multilineage Potential of Human Placenta-Derived Mesenchymal Cells," Blood 100(11):517a, Abstract 2022 (2002).
Weiss et al., "Human Umbilical Cord Matrix Stem Cells: Preliminary Characterization and Effect of Transplantation in a Rodent Model of Parkinson's Disease", 24, 781-792 (2006).
Weissman et al., "Stem and Progenitor Cells: Origins, Phenotypes, Lineage Commitments, and Transdifferentiations", Annu. Rev. Cell Dev. Biol. 17:387-403 (2001).
Wiesmann, et al., "Effects of Caspase Inhibitors on Hematopoietic Engraftment After Short-Term Culture," Cell. Transplant. 11(4):351-358 (2002).
Woods, et al., "Osomometric and permeability characteristics of human placental/umbilical cord blood CD34+ cells and their application to cryopreservation," J. Hemather. Stem Cell Res. 9(2):161-173 (2000).
Wulf et al., "Mesengenic Progenitor Cells Derived from Human Placenta," Tissue Engineering 10(7/8): 1136-1147 (2004).
Xu et al., "BMP4 Initiates Human Embryonic Stem Cell Differentiation to Trophoblast," Nature Biology 20:1261-1264 (2002).
Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).
Ye, et al., "Recovery of Placental-Derived Adherent Cells with Mesenchymal Stem Cell Characteristics," Blood 98(11/1):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yen, B. Linju et al, "Isolation of multipotent cells from human term placenta" Stem Cells (Dayton, Ohio) vol. 23, No. 1, Jan. 2005, pp. 3-9, XP002443187 ISSN: 1065-5099 (2005).
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Yu et al., "FLT3 Ligand Promotes the Generation of a Distinct CD34+ Human Natural Killer Cell Progenitor That Responds to Interleukin-15," Blood 92(10):1647-1657 (1998).
Yui et al., "Functional, Long-term Cultures of Human Term Trophoblasts Purified by Column-elimination of CD9 Expressing Cells," Placenta 15:231-246 (1994).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol., 47(1):109-16 (2003).
Zhang, et al., "Human Placenta-Derived Mesenchymal Progenitor Cells Support Culture Expansion of Long-Term Culture-Initiating Cells from Cord Blood CD34+ Cells." Exp. Hematol. 32: 657-664 (2004).

* cited by examiner

# US 8,926,964 B2

METHODS OF GENERATING NATURAL KILLER CELLS

1. RELATED APPLICATIONS

This application claims the benefit of U.S. Provisional Patent Application Ser. No. 61/363,981, filed Jul. 13, 2010 and U.S. Provisional Patent Application Ser. No. 61/497,897, filed Jun. 16, 2011, the disclosures of which are incorporated by reference herein in their entirety.

2. FIELD

Provided herein are methods of producing a population of natural killer cells, e.g., natural killer cells derived from placenta, for example, from placental perfusate (e.g., human placental perfusate) such as placenta-derived intermediate natural killer cells, or other tissues, for example, umbilical cord blood or peripheral blood. Also provided herein are expanded natural killer cell populations produced by the methods presented herein. Further provided herein are methods of using the placental perfusate, and the natural killer cells therefrom, to suppress the proliferation of tumor cells. In certain embodiments, the natural killer cells are used in combination with, or treated with, one or more immunomodulatory compounds, e.g., immunomodulatory compounds referred to as IMiDs™.

3. BACKGROUND

Natural killer (NK) cells are cytotoxic lymphocytes that constitute a major component of the innate immune system. NK cells do not express T-cell antigen receptors (TCR), CD3 or surface immunoglobulins (Ig) B cell receptor. NK cells generally express the surface markers CD16 (FcγRIII) and CD56 in humans, but a subclass of human NK cells is CD16⁻. NK cells are cytotoxic; small granules in their cytoplasm contain special proteins such as perforin and proteases known as granzymes. Upon release in close proximity to a cell targeted for killing, perforin forms pores in the cell membrane of the target cell through which the granzymes and associated molecules can enter, inducing apoptosis. One granzyme, granzyme B (also known as granzyme 2 and cytotoxic T-lymphocyte-associated serine esterase 1), is a serine protease crucial for rapid induction of target cell apoptosis in the cell-mediated immune response.

NK cells are activated in response to interferons or macrophage-derived cytokines Activated NK cells are referred to as lymphokine activated killer (LAK) cells. NK cells possess two types of surface receptors, labeled "activating receptors" and "inhibitory receptors," that control the cells' cytotoxic activity.

Among other activities, NK cells play a role in the host rejection of tumors. Because cancer cells have reduced or no class I MHC expression, they can become targets of NK cells. Accumulating clinical data suggest that haploidentical transplantation of human NK cells isolated from peripheral blood monomuclear cells (PBMC) or bone marrow mediate potent anti-leukemia effects without incurring detectable graft versus host disease (GVHD). See Ruggeri et al., *Science* 295: 2097-2100 (2002)). Natural killer cells can become activated by cells lacking, or displaying reduced levels of, major histocompatibility complex (MHC) proteins. Additionally, the activating receptors expressed on NK cells are known to mediate detection of "stressed" or transformed cells with express ligands to activating receptors and therefore trigger the NK cell activation. For instance, NCR1 (NKp46) binds viral hemagglutinins NKG2D ligands include CMV UL16-binding protein 1 (ULB1), ULB2, ULB3 and MHC-class-1-polypeptide-related sequence A (MICA) and MICB proteins. NK protein 2B4 binds CD48, and DNAM-1 binds Poliovirus receptor (PVR) and Nectin-2, both are consistently detected in acute myeloid leukemia (AML). See Penda et al., *Blood* 105: 2066-2073 (2004). Moreover, lysis of AML has been described to be mainly natural cytotoxicity receptor (NCR) dependent. See Fauriat et al., *Blood* 109: 323-330 (2007). Activated and expanded NK cells and LAK cells from peripheral blood have been used in both ex vivo therapy and in vivo treatment of patients having advanced cancer, with some success against bone marrow related diseases, such as leukemia; breast cancer; and certain types of lymphoma. LAK cell treatment requires that the patient first receive IL-2, followed by leukopheresis and then an ex vivo incubation and culture of the harvested autologous blood cells in the presence of IL-2 for a few days. The LAK cells must be reinfused along with relatively high doses of IL-2 to complete the therapy. This purging treatment is expensive and can cause serious side effects. These include fluid retention, pulmonary edema, drop in blood pressure, and high fever.

In spite of the advantageous properties of NK cells in killing tumor cells and virus-infected cells, they remain difficult to work with and to apply in immunotherapy, primarily due to the difficulty in maintaining their tumor-targeting and tumoricidal capabilities during culture and expansion. Thus, there is a need in the art to develop an efficient method to produce and expand natural killer cells that retain tumoricidal functions.

4. SUMMARY

Provided herein are methods of expanding and differentiating cells, for example, hematopoietic cells, such as hematopoietic stem cells, e.g., CD34⁺ hematopoietic stem cells, to natural killer cells. In one aspect, provided herein is a method of producing natural killer (NK) cells comprising culturing hematopoietic stem cells or progenitor cells, e.g., CD34⁺ stem cells or progenitor cells, in a first medium to produce expanded and differentiated cells, and subsequently culturing said expanded cells in a second medium in which said cells expand further and differentiate into natural killer cells. The first and second steps comprise culturing the cells in media with a unique combination of cellular factors. In certain embodiments, said cellular factors (e.g., cytokines) are not comprised within an undefined component of the media (e.g., serum), for example, the cellular factors (e.g., cytokines) are exogenous to the undefined component of the media (e.g., serum). In certain embodiments, said method is a two-step method. In certain embodiments, said method does not comprise any third or intermediate step in which the cells are contacted. In a specific embodiment, provided herein is a method of producing a population of activated natural killer (NK) cells, comprising: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; and (b) expanding the cells from the first step in a second medium comprising interleukin-2 (IL-2), to produce a population of activated NK cells. Natural killer cells produced by the methods provided herein (e.g., two-step method) are referred to herein as TSNK cells.

In certain embodiments, said first medium comprises medium comprising one or more of human serum (e.g., human serum AB) fetal bovine serum (FBS) or fetal calf serum (FCS), e.g., 5% to 20% v/v, stem cell factor (SCF), e.g., 1 ng/mL to 50 ng/mL, FMS-like tyrosine kinase-3 ligand (Flt-3 ligand), e.g., 1 ng/ml to 20 ng/mL; interleukin-7 (IL-7), e.g., 1 ng/mL to 50 ng/mL; thrombopoietin (TPO), e.g., 1 ng/mL to 50 ng/mL; interleukin-2 (IL-2), e.g., 50 IU/mL to 500 IU/mL; interleukin-15 (IL-15), e.g., 1 ng/mL to 50 ng/mL; and/or heparin, e.g., 0.1 IU/mL to 10 IU/mL. In a specific embodiment, said first medium comprises stem cell factor (SCF), interleukin-7 (IL-7) and interleukin-15 (IL-15). In another specific embodiment, said first medium comprises growth medium, human serum (e.g., human serum AB), FBS FCS, SCF, IL-7 and IL-15. In another specific embodiment, said first medium further comprises Flt-3 ligand (Flt3-L), TPO, IL-2, and/or heparin. In another specific embodiment, said first medium comprises growth medium, 10% human serum or fetal bovine serum, 20 ng/mL SCF, 10 ng/ml Flt3-L, 20 ng/mL IL-7, 20 ng/mL TPO, 200 IU/mL IL-2, 10 ng/mL IL-15, and 1.5 IU/mL heparin. In another specific embodiment, said first medium does not comprise IL-2. In another specific embodiment, said culturing in said first medium comprises culturing using feeder cells, e.g., K562 cells, e.g., mitomycin C-treated K562 cells, peripheral blood mononuclear cells (PBMCs), e.g., mitomycin C-treated PBMCs or tissue culture-adherent stem cells, e.g., mitomycin C-treated tissue culture-adherent stem cells.

In certain embodiments, said first medium is, or comprises GBGM®, AIM-V®, X-VIVO™ 10, X-VIVO™ 15, OPT-MIZER, STEMSPAN® H3000, CELLGRO COMPLETE™, and/or DMEM:F12. In certain embodiments, said medium comprises O-acetyl-carnitine (also referred to as acetylcarnitine, O-acetyl-L-carnitine or OAC), e.g., about 0.5 mM-10 mM. In one embodiment, said medium comprises Stemspan® H3000, and/or DMEM:F12 and OAC, e.g., about 0.5, 1, 2, 3, 4, 5, 6, 7, 8, 9, or 10 mM. In a specific embodiment, said medium comprises GBGM®. In another specific embodiment, said medium comprises DMEM:F12 and about 5 mM of OAC. In another specific embodiment, said medium comprises Stemspan® H3000 and about 5 mM of OAC.

In certain embodiments, said second medium comprises cell growth medium comprising one or more of: human serum (e.g., human serum AB), fetal bovine serum (FBS) or fetal calf serum (FCS), e.g., 5%-15% FCS v/v; IL-2, e.g., 10 IU/mL to 1000 IU/mL; transferrin, e.g., 10 µg/mL to 50 µg/mL; insulin, e.g., 5 µg/mL to 20 µg/mL; ethanolamine, e.g., $5 \times 10^{-4}$ to $5 \times 10^{-5}$ M; oleic acid, e.g., 0.1 µg/mL to 5 µg/mL; linoleic acid, e.g., 0.1 µg/mL to 5 µg/mL; palmitic acid, e.g., 0.05 µg/mL to 2 µg/mL; bovine serum albumin (BSA), e.g., 1 µg/mL to 5 µg/mL; and/or phytohemagglutinin, e.g., 0.01 µg/mL to 1 µg/mL. In a specific embodiment, said second medium comprises IL-2. In a more specific embodiment, said second medium comprises cell growth medium comprising human serum, FBS or FCS, e.g., 10% v/v, IL-2, transferrin, insulin, ethanolamine, oleic acid, linoleic acid, palmitic acid, bovine serum albumin (BSA) and/or phytohemagglutinin. In a more specific embodiment, said second medium comprises Iscove's Modified Dulbecco's Medium (IMDM), 10% human serum, FBS or FCS, 400 IU IL-2, 35 µg/mL transferrin, 5 µg/mL insulin, $2 \times 10^{-5}$ M ethanolamine, 1 µg/mL oleic acid, 1 µg/mL linoleic acid, 0.2 µg/mL palmitic acid, 2.5 µg/mL BSA and 0.1 µg/mL phytohemagglutinin. In another specific embodiment, said culturing in said second medium comprises culturing using feeder cells, e.g., K562 cells (e.g., mitomycin C-treated K562 cells) or PBMCs (e.g., mitomycin C-treated PBMC), e.g., at the time the cells are started in said second medium, 1, 2, 3, 4, 5, 6, 7, 8, 9 or 10 days thereafter. In certain embodiments, said medium comprises GBGM®, AIM-V®, X-VIVO™ 10, X-VIVO™ 15, OPT-MIZER, STEMSPAN® H3000, CELLGRO COMPLETE™, and/or DMEM:F12. In certain embodiments, said medium comprises one or more of O-acetyl-carnitine (also referred to as acetylcarnitine, O-acetyl-L-carnitine or OAC), or a compound that affects acetyl-CoA cycling in mitodronia, thiazovivin, Y-27632, pyintegrin, Rho kinase (ROCK) inhibitors, caspase inhibitors or other anti-apoptotic compounds/peptides, NOVA-RS (Sheffield Bio-Science) or other small-molecule growth enhancers. In certain embodiments, said medium comprises nicotinamide. In certain embodiments, said medium comprises about 0.5 mM-10 mM OAC. In one embodiment, said medium comprises Stemspan® H3000, and/or DMEM:F12 and OAC, e.g., about 0.5, 1, 2, 3, 4, 5, 6, 7, 8, 9, or 10 mM. In a specific embodiment, said medium comprises GBGM®. In another specific embodiment, said medium comprises DMEM:F12 and about 5 mM of OAC. In another specific embodiment, said medium comprises Stemspan® H3000 and about 5 mM of OAC.

In another specific embodiment, provided herein is a method of producing a population of activated natural killer (NK) cells, comprising: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; and (b) expanding the cells from step (a) in a second medium comprising interleukin-2 (IL-2), to produce a population of activated NK cells.

In another specific embodiment, provided herein is a two-step method of producing a population of activated natural killer (NK) cells, wherein a first step of said method comprises expanding a population of hematopoietic stem or progenitor cells in a first medium comprising one or more of SCF, IL-7 and IL-15, and wherein said SCF, IL-7 and IL-15 are not comprised within an undefined component of said medium (e.g., serum), and wherein a plurality of hematopoietic stem or progenitor cells within said population of hematopoietic stem or progenitor cells differentiate into NK cells during said expanding; and wherein a second step of said method comprises expanding the cells from the first step in a second medium comprising IL-2, to produce activated NK cells. In another specific embodiment, said first medium further comprises one or more of Fms-like-tyrosine kinase 3 ligand (Flt3-L), thrombopoietin (Tpo), interleukin-2 (IL-2), and/or heparin. In another specific embodiment, said first medium further comprises about 5%-20% fetal bovine serum or human serum. In another specific embodiment, the SCF is present at a concentration of about 1 to about 150 ng/mL in the first medium. In another specific embodiment, the Flt3-L is present at a concentration of about 1 to about 150 ng/mL in the first medium. In another specific embodiment, the IL-2 is present at a concentration of about 50 to about 1500 IU/mL in the first medium. In another specific embodiment, the IL-7 is present at a concentration of about 1 to about 150 ng/mL in the first medium. In another specific embodiment, the IL-15 is present at a concentration 1 to about 150 ng/mL in the first medium. In another specific embodiment, the Tpo is present at a concentration of about 1 to about 150 ng/mL in the first medium. In another specific embodiment, the heparin is present at a concentration of about 0.1 to about 30 U/mL in the first medium. In another specific embodiment, the IL-2 in the second step is present at a concentration 50 to about 1500 IU/mL in the second medium. In another specific embodiment, said second medium additionally comprises one or more of fetal calf serum (FCS), transferrin, insulin, ethanolamine, oleic acid, linoleic acid, palmitic acid, bovine serum albumin (BSA) and phytohemagglutinin.

In certain specific embodiments, said hematopoietic stem or progenitor cells are cultured in said first medium for 1, 2, 3, 4, 5, 6, 7, 8, 9, 10, 11, 12, 13, 14, 15, 16, 17, 18, 19, 20, 21, 22, 23, 24, 25, 26, 27 or 28 days before said culturing in said second medium. In certain other specific embodiments, said cells are cultured in said second medium for 1, 2, 3, 4, 5, 6, 7, 8, 9, 10, 11, 12, 13, 14, 15, 16, 17, 18, 19, 20, 21, 22, 23, 24, 25, 26, 27 or 28 days. In a more specific embodiment, said hematopoietic stem or progenitor cells are cultured in said first medium for 21 days, and then cultured in said second medium for 21 days.

Further provided herein is a population of natural killer cells produced by the two-step method described above, referred to herein as TSNK cells. In a specific embodiment, said NK cells (e.g., TSNK cells) are $CD3^-CD56^+$. In a specific embodiment, said NK cells (e.g., TSNK cells) are $CD3^-CD56^+CD16^-$. In another specific embodiment, said NK cells (e.g., TSNK cells) are additionally $CD94^+CD117^+$. In another specific embodiment, said NK cells (e.g., TSNK cells) are additionally $CD161^-$. In another specific embodiment, said NK cells (e.g., TSNK cells) are additionally $NKG2D^+$. In another specific embodiment, said NK cells are additionally $NKp46^+$. In another specific embodiment, said said NK cells are additionally $CD226^+$.

In certain embodiments, greater than 90%, 92%, 94%, 96% or 98% of said TSNK cells are $CD56^+$ and $CD16^-$. In some embodiments, at least 80%, 82%, 84%, 86%, 88% or 90% of said TSNK cells are $CD3^-$ and $CD56^+$. In other embodiments, greater than 90%, 92%, 94%, 96% or 98% of said TSNK cells are $CD56^+$, $CD16^-$ and $CD3^-$. In other embodiments, at least 50%, 52%, 54%, 56%, 58% or 60% of said TSNK cells are $NKG2D^+$. In other embodiments, fewer than 10%, 9%, 8%, 7%, 6%, 5%, 4% or 3% of said TSNK cells are $NKB1^+$. In certain other embodiments, fewer than 10%, 8%, 6%, 4% or 2% of said TSNK cells are $NKAT2^+$. In certain other embodiments, fewer than 10%, 8%, 6%, 4% or 2% of said TSNK cells are $CD56^+$ and $CD16^+$. In more specific embodiments, at least 50%, 55%, 60%, 65% or 70% of said $CD3^-$, $CD56^+$ TSNK cells are $NKp46^+$. In other more specific embodiments, at least 50%, 55%, 60%, 65%, 70%, 75%, 80% or 85% of said $CD3^-$, $CD56^+$ TSNK cells are $CD117^+$. In other more specific embodiments, at least 20%, 25%, 30%, 35%, 40% or 45% of said $CD3^-$, $CD56^+$ TSNK cells are $CD94^+$. In other more specific embodiments, at least 10%, 20%, 25%, 30%, 35%, 40%, 45% or 50% of said $CD3^-$, $CD56^+$ TSNK cells are $CD161^-$. In other more specific embodiments, at least 10%, 12%, 14%, 16%, 18% or 20% of said $CD3^-$, $CD56^+$ TSNK cells are $CD226^+$. In more specific embodiments, at least 20%, 25%, 30%, 35% or 40% of said $CD3^-$, $CD56^+$ TSNK cells are $CD7^+$. In more specific embodiments, at least 30%, 35%, 40%, 45%, 50%, 55% or 60% of said $CD3^-$, $CD56^+$ TSNK cells are $CD5^+$.

In another aspect, provided herein is the use of TSNK cells to suppress tumor cell proliferation, treat viral infection or treat cancer, e.g., blood cancers and solid tumors. In certain embodiments, the TSNK cells are contacted with, or used in combination with, an immunomodulatory compound, e.g., an immunomodulatory compound described in Section 6.2.1, below, or thalidomide.

In a specific embodiment, said cancer is a solid tumor. In another embodiment, said cancer is a blood cancer. In specific embodiments, the cancer is glioblastoma, primary ductal carcinoma, leukemia, acute T cell leukemia, chronic myeloid lymphoma (CML), acute myelogenous leukemia (AML), chronic myelogenous leukemia (CML), lung carcinoma, colon adenocarcinoma, histiocytic lymphoma, colorectal carcinoma, colorectal adenocarcinoma, prostate cancer, multiple myeloma, or retinoblastoma.

In another embodiment, the hematopoietic cells, e.g., hematopoietic stem cells or progenitor cells, from which the TSNK cells are produced, are obtained from placental perfusate, umbilical cord blood or peripheral blood. In another specific embodiment, the hematopoietic cells, e.g., hematopoietic stem cells or progenitor cells, from which the TSNK cells are produced, are combined cells from placental perfusate and cord blood, e.g., cord blood from the same placenta as the perfusate. In another specific embodiment, said umbilical cord blood is isolated from a placenta other than the placenta from which said placental perfusate is obtained. In certain embodiments, the combined cells can be obtained by pooling or combining the cord blood and placental perfusate. In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by volume to obtain the combined cells. In a specific embodiment, the cord blood and placental perfusate are combined at a ratio of from 10:1 to 1:10, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10. In a more specific embodiment, the cord blood and placental perfusate are combined at a ratio of 8.5:1.5 (85%: 15%).

In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by total nucleated cells (TNC) content to obtain the combined cells. In a specific embodiment, the cord blood and placental perfusate are combined at a ratio of from 10:1 to 10:1, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10.

In one embodiment, therefore, provided herein is a method of treating an individual having cancer or a viral infection, comprising administering to said individual an effective amount of isolated TSNK cells.

In a specific embodiment, the isolated TSNK cells have been treated with an immunomodulatory compound, e.g. an immunomodulatory compound described in Section 6.2.1 below, or thalidomide, prior to said administration. In another specific embodiment, the method comprises administering to the individual (1) an effective amount of isolated TSNK cells; and (2) an effective amount of an immunomodulatory compound or thalidomide. An "effective amount" in this context means an amount of TSNK cells, and optionally immunomodulatory compound or thalidomide, that results in a detectable improvement in one or more symptoms of said cancer or said infection, compared to an individual having said cancer or said infection who has not been administered said TSNK cells and, optionally, an immunomodulatory compound or thalidomide. In a specific embodiment, said immunomodulatory compound is lenalidomide or pomalidomide. In another embodiment, the method additionally comprises administering an anticancer compound to the individual, e.g., one or more of the anticancer compounds described in Section 6.8.3, below.

In another embodiment, provided herein is a method of suppressing the proliferation of tumor cells comprising contacting the tumor cells with a therapeutically effective amount of TSNK cells.

In a specific embodiment, the isolated TSNK cells have been treated with an immunomodulatory compound, e.g. an immunomodulatory compound described in Section 6.2.1, below, or thalidomide, prior to said contacting. In another specific embodiment, the tumor cells are additionally contacted with an effective amount of an immunomodulatory compound, e.g. an immunomodulatory compound described in Section 6.2.1, below, or thalidomide. An "effective amount" in this context means an amount of TSNK cells, and optionally an immunomodulatory compound or thalidomide, that results in a detectable suppression of said tumor cells compared to an equivalent number of tumor cells not contacted with said TSNK cells, and optionally an immunomodulatory compound or thalidomide. In another specific embodiment, the method further comprises contacting the tumor cells with an effective amount of an anticancer compound, e.g., an anticancer compound described in Section 6.8.3, below.

In a specific embodiment of this method, the tumor cells are blood cancer cells. In another specific embodiment, the tumor cells are solid tumor cells. In another embodiment, the tumor cells are primary ductal carcinoma cells, leukemia cells, acute T cell leukemia cells, chronic myeloid lymphoma (CML) cells, acute myelogenous leukemia cells, chronic myelogenous leukemia (CML) cells, glioblastoma cells, lung carcinoma cells, colon adenocarcinoma cells, histiocytic lymphoma, multiple myeloma cells, retinoblastoma cell, colorectal carcinoma cells, prostate cancer cells, or colorectal adenocarcinoma cells. In another specific embodiment, said contacting takes place in vitro. In another specific embodiment, said contacting takes place in vivo. In a more specific embodiment, said in vivo contacting takes place in a human.

In another aspect, provided herein is a method of treating an individual having multiple myeloma, comprising administering to the individual (1) lenalidomide; (2) melphalan; and (3) expanded NK cells, wherein said NK cells are effective to treat multiple myeloma in said individual. In a specific embodiment, said NK cells are cord blood NK cells, or NK cells produced from cord blood hematopoietic cells, e.g., hematopoietic stem cells. In another embodiment, said NK cells have been produced by any of the methods described herein for producing NK cells, e.g., for producing TSNK cells. In another embodiment, said NK cells have been expanded prior to said administering. In another embodiment, said lenalidomide, melphalan, and/or NK cells are administered separately from each other. In certain specific embodiments of the method of treating an individual with multiple myeloma, said NK cells are produced by a two-step method of producing a population of activated natural killer (NK) cells, wherein a first step of said method comprises expanding a population of hematopoietic stem or progenitor cells in a first medium comprising one or more of stem cell factor (SCF), interleukin-7 (IL-7) and interleukin-15 (IL-15), and wherein said SCF, IL-7 and IL-15 are not comprised within an undefined component of said medium, and wherein a plurality of hematopoietic stem or progenitor cells within said population of hematopoietic stem or progenitor cells differentiate into NK cells during said expanding; and wherein a second step of said method comprises expanding the cells from the first step in a second medium comprising interleukin-2 (IL-2), to produce activated NK cells.

In other specific embodiments of the method of treating an individual with multiple myeloma, said NK cells are produced by a method comprising: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; and (b) expanding the cells from step (a) in a second medium comprising interleukin-2 (IL-2), to produce a population of activated NK cells.

In another aspect, provided herein is a method of treating an individual having chronic lymphocytic leukemia (CLL), comprising administering to the individual a therapeutically effective dose of (1) lenalidomide; (2) melphalan; (3) fludarabine; and (4) expanded NK cells, e.g., TSNK cells, wherein said NK cells are effective to treat said CLL in said individual. In a specific embodiment, said NK cells are cord blood NK cells, or NK cells produced from cord blood hematopoietic cells, e.g., hematopoietic stem cells. In another embodiment, said NK cells have been produced by any of the methods described herein for producing NK cells, e.g., for producing TSNK cells. In a specific embodiment of any of the above methods, said NK cells have been expanded for at least 10 days prior to said administering. In a specific embodiment of any of the above methods, said lenalidomide, melphalan, fludarabine, and expanded NK cells are administered to said individual separately. In certain specific embodiments of the method of treating an individual with CLL, said NK cells are produced by a two-step method of producing a population of activated natural killer (NK) cells, wherein a first step of said method comprises expanding a population of hematopoietic stem or progenitor cells in a first medium comprising one or more of stem cell factor (SCF), interleukin-7 (IL-7) and interleukin-15 (IL-15), and wherein said SCF, IL-7 and IL-15 are not comprised within an undefined component of said medium, and wherein a plurality of hematopoietic stem or progenitor cells within said population of hematopoietic stem or progenitor cells differentiate into NK cells during said expanding; and wherein a second step of said method comprises expanding the cells from the first step in a second medium comprising interleukin-2 (IL-2), to produce activated NK cells.

In other specific embodiments of the method of treating an individual with CLL, said NK cells are produced by a method comprising: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; and (b) expanding the cells from step (a) in a second medium comprising interleukin-2 (IL-2), to produce a population of activated NK cells.

In one aspect, provided herein is a method of cryopreserving a population of NK cells, e.g., TSNK cells. In one embodiment, said method comprises: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; (b) expanding the cells from step (a) in a second medium comprising interleukin-2 (IL-2), to produce a population of activated NK cells, and (c) cryopreserving the NK cells from step (b) in a cryopreservation medium. In a specific embodiment, said step (c) further comprises (1) preparing a cell suspension solution; (2) adding cryopreservation medium to the cell suspension solution from step (1) to obtain cryopreserved cell suspension; (3) cooling the cryopreserved cell suspension from step (3) to obtain a cryopreserved sample; and (4) storing the cryopreserved sample below −80° C. In certain embodiments, the method includes no intermediary steps between step (a) and (b), and between step (b) and (c).

In another embodiment, said method of cryopreserving a population of NK cells, e.g., TSNK cells comprises: (a) expanding a population of hematopoietic stem or progenitor cells in a first medium comprising one or more of stem cell factor (SCF), IL-2, interleukin-7 (IL-7), interleukin-15 (IL-15) and heparin, and wherein said SCF, IL-2, IL-7 and IL-15 are not comprised within an undefined component of said medium, and wherein a plurality of hematopoietic stem or progenitor cells within said population of hematopoietic stem or progenitor cells differentiate into NK cells during said expanding; (b) expanding the cells from step (a) in a second medium comprising interleukin-2 (IL-2), to produce activated NK cells; and (c) cryopreserving the NK cells from step (b) in a cryopreservation medium. In a specific embodiment, said step (c) further comprises (1) preparing a cell suspension solution; (2) adding cryopreservation medium to the cell suspension solution from step (1) to obtain cryopreserved cell suspension; (3) cooling the cryopreserved cell suspension from step (3) to obtain a cryopreserved sample; and (4) storing the cryopreserved sample below −80° C. In certain embodiments, the method includes no intermediary steps between step (a) and (b), and between step (b) and (c), and/or no additional culturing steps prior to step (a).

In another specific embodiment, the hematopoietic cells, e.g., hematopoietic stem or progenitor cells from which the TSNK cells are produced express one or more of the microRNAs hsa-miR-380, hsa-miR-512, hsa-miR-517, hsa-miR-518c, hsa-miR-519b, and hsa-miR-520a at a detectably higher level than peripheral blood natural killer cells, as determined, e.g., by quantitative real-time PCR (qRT-PCR).

In another specific embodiment of the above methods, said TSNK cells are contacted with an immunomodulatory compound or thalidomide in an amount and for a time sufficient for said natural killer cells to express detectably more granzyme B or perforin than an equivalent number of natural killer cells, e.g., TSNK cells, not contacted with said immunomodulatory compound or thalidomide. In another specific embodiment, said TSNK cells are contacted with an immunomodulatory compound or thalidomide in an amount and for a time sufficient for said cells to exhibit detectably more cytotoxicity towards said tumor cells than an equivalent number of natural killer cells, e.g., TSNK cells, not contacted with said immunomodulatory compound, e.g., lenalidomide or pomalidomide, or with thalidomide. In another specific embodiment, said TSNK cells express one or more of BAX, CCL5, CCR5, CSF2, FAS, GUSB, IL2RA, or TNFRSF18 at a higher level than an equivalent number of natural killer cells, e.g. TSNK cells, not contacted with said immunomodulatory compound or thalidomide. In another specific embodiment, said TSNK cells express one or more of ACTB, BAX, CCL2, CCL3, CCL5, CCR5, CSF1, CSF2, ECE1, FAS, GNLY, GUSB, GZMB, IL1A, IL2RA, IL8, IL10, LTA, PRF1, PTGS2, SKI, and/or TBX21 at a higher level than an equivalent number of natural killer cells, e.g., TSNK cells, not contacted with said immunomodulatory compound or thalidomide.

In certain embodiments of the methods of treatment or tumor suppression above, TSNK cells are combined with other natural killer cells, e.g., natural killer cells isolated from placental perfusate, umbilical cord blood or peripheral blood, or produced from hematopoietic cells by a different method. In specific embodiments, the TSNK cells are combined with natural killer cells from another source, or made by a different method, in a ratio of about 100:1, 95:5, 90:10, 85:15, 80:20, 75:25, 70:30, 65:35, 60:40, 55:45; 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In another aspect, provided herein is a composition comprising isolated TSNK cells. In a specific embodiment, said TSNK cells are produced from hematopoietic cells, e.g., hematopoietic stem or progenitor cells isolated from placental perfusate, umbilical cord blood, and/or peripheral blood. In another specific embodiment, said TSNK cells comprise at least 50% of cells in the composition. In another specific embodiment, said TSNK cells comprise at least 80%, 85%, 90%. 95%, 98% or 99% of cells in the composition. In certain embodiments, greater than 90%, 92%, 94%, 96% or 98% of TSNK cells in said composition are CD56$^+$ and CD16$^-$. In other embodiments, at least 80%, 82%, 84%, 86%, 88% or 90% of TSNK cells in said composition are CD3$^-$ and CD56$^+$. In other embodiments, at least 50%, 52%, 54%, 56%, 58% or 60% of said cells are NKG2D$^+$. In other embodiments, fewer than 10%, 9%, 8%, 7%, 6%, 5%, 4% or 3% of said cells are NKB1$^+$. In certain other embodiments, fewer than 10%, 8%, 6%, 4% or 2% of said TSNK cells are NKAT2$^+$. In certain other embodiments, fewer than 10%, 8%, 6%, 4% or 2% of said TSNK cells are CD56$^+$ and CD16$^+$. In more specific embodiments, at least 50%, 55%, 60%, 65% or 70% of said CD3$^-$, CD56$^+$ TSNK cells are NKp46$^+$. In other more specific embodiments, at least 50%, 55%, 60%, 65%, 70%, 75%, 80% or 85% of said CD3$^-$, CD56$^+$ TSNK cells are CD117$^+$. In other more specific embodiments, at least 20%, 25%, 30%, 35%, 40% or 45% of said CD3$^-$, CD56$^+$ TSNK cells are CD94$^+$. In other more specific embodiments, at least 10%, 12%, 14%, 16%, 18% or 20% of said CD3$^-$, CD56$^+$ TSNK cells are CD226$^+$. In more specific embodiments, at least 20%, 25%, 30%, 35% or 40% of said CD3$^-$, CD56$^+$ TSNK cells are CD7$^+$. In more specific embodiments, at least 30%, 35%, 40%, 45%, 50%, 55% or 60% of said CD3$^-$, CD56$^+$ TSNK cells are CD5$^+$.

In another specific embodiment, said isolated CD56$^+$, CD16$^-$ TSNK cells are from a single individual. In a more specific embodiment, said isolated CD56$^+$, CD16$^-$ natural killer cells comprise natural killer cells from at least two different individuals. In another specific embodiment, said TSNK cells have been contacted with an immunomodulatory compound or thalidomide in an amount and for a time sufficient for said TSNK cells to express detectably more granzyme B or perforin than an equivalent number of natural killer cells, i.e. TSNK cells, not contacted with said immunomodulatory compound or thalidomide. In another specific embodiment, said composition additionally comprises an immunomodulatory compound or thalidomide. In certain embodiments, the immunomodulatory compound is a compound described in Section 6.2.1 below, e.g., an amino-substituted isoindoline compound.

In another specific embodiment, the composition additionally comprises one or more anticancer compounds, e.g., one or more of the anticancer compounds described in Section 6.8.2, below.

In a more specific embodiment, the composition comprises TSNK cells and natural killer cells from another source, or made by another method. In a specific embodiment, said other source is placental blood and/or umbilical cord blood. In another specific embodiment, said other source is peripheral blood. In more specific embodiments, the TSNK cells are combined with natural killer cells from another source, or made by another method in a ratio of about 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In another specific embodiment, the composition comprises TSNK cells and either isolated placental perfusate or isolated placental perfusate cells. In a more specific embodiment, said placental perfusate is from the same individual as said TSNK cells. In another more specific embodiment, said placental perfusate comprises placental perfusate from a different individual than said TSNK cells. In another specific embodiment, all, or substantially all (e.g., greater than 90%, 95%, 98% or 99%) of cells in said placental perfusate are fetal cells. In another specific embodiment, the placental perfusate or placental perfusate cells, comprise fetal and maternal cells. In a more specific embodiment, the fetal cells in said placental perfusate comprise less than about 90%, 80%, 70%, 60% or 50% of the cells in said perfusate. In another specific embodiment, said perfusate is obtained by passage of a 0.9% NaCl solution through the placental vasculature. In another specific embodiment, said perfusate comprises a culture medium. In another specific embodiment, said perfusate has been treated to remove erythrocytes. In another specific embodiment, said composition comprises an immunomodulatory compound, e.g., an immunomodulatory compound described in Section 5.2.1.1 below, e.g., an amino-substituted isoindoline compound. In another specific embodiment, the composition additionally comprises one or more anticancer compounds, e.g., one or more of the anticancer compounds described in Section 6.8.2, below.

In another specific embodiment, the composition comprises TSNK cells and placental perfusate cells. In a more specific embodiment, said placental perfusate cells are from the same individual as said TSNK cells. In another more specific embodiment, said placental perfusate cells are from a different individual than said TSNK cells. In another specific embodiment, the composition comprises isolated placental perfusate and isolated placental perfusate cells, wherein said isolated perfusate and said isolated placental perfusate cells are from different individuals. In another more specific embodiment of any of the above embodiments comprising placental perfusate, said placental perfusate comprises placental perfusate from at least two individuals. In another more specific embodiment of any of the above embodiments comprising placental perfusate cells, said isolated placental perfusate cells are from at least two individuals. In another specific embodiment, said composition comprises an immunomodulatory compound. In another specific embodiment, the composition additionally comprises one or more anticancer compounds, e.g., one or more of the anticancer compounds described in Section 6.8.2, below.

4.1. Definitions

As used herein, the terms "immunomodulatory compound" and "IMiD™" do not encompass thalidomide.

As used herein, "lenalidomide" means 3-(4' aminoisoindoline-1'-one)-1-piperidine-2,6-dione (Chemical Abstracts Service name) or 2,6-Piperidinedione, 3-(4-amino-1,3-dihydro-1-oxo-2H-isoindol-2-yl)-(International Union of Pure and Applied Chemistry (IUPAC) name). As used herein, "pomalidomide" means 4-amino-2-(2,6-dioxopiperidin-3-yl)isoindole-1,3-dione.

As used herein, "multipotent," when referring to a cell, means that the cell has the capacity to differentiate into a cell of another cell type. In certain embodiments, "a multipotent cell" is a cell that has the capacity to grow into any subset of the mammalian body's approximately 260 cell types. Unlike a pluripotent cell, a multipotent cell does not have the capacity to form all of the cell types.

As used herein, "feeder cells" refers to cells of one type that are co-cultured with cells of a second type, to provide an environment in which the cells of the second type can be maintained, and perhaps proliferate. Without being bound by any theory, feeder cells can provide, for example, peptides, polypeptides, electrical signals, organic molecules (e.g., steroids), nucleic acid molecules, growth factors (e.g., bFGF), other factors (e.g., cytokines), and metabolic nutrients to target cells. In certain embodiments, feeder cells grow in a mono-layer.

As used herein, "natural killer cell" or "NK cells" without further modification, includes natural killer cells from any tissue source.

As used herein, "TSNK" and "TSNK cells" refer to natural killer cells produced by the culture/expansion methods (e.g., two-step method) disclosed herein.

As used herein, "placental perfusate" means perfusion solution that has been passed through at least part of a placenta, e.g., a human placenta, e.g., through the placental vasculature, including a plurality of cells collected by the perfusion solution during passage through the placenta.

As used herein, "placental perfusate cells" means nucleated cells, e.g., total nucleated cells, isolated from, or isolatable from, placental perfusate.

As used herein, "tumor cell suppression," "suppression of tumor cell proliferation," and the like, includes slowing the growth of a population of tumor cells, e.g., by killing one or more of the tumor cells in said population of tumor cells, for example, by contacting the population of tumor cells with, e.g., TSNK cells or a population of cells comprising TSNK cells.

As used herein, the term "hematopoietic cells" includes hematopoietic stem cells and hematopoietic progenitor cells.

As used herein, the "undefined component" is a term of art in the culture medium field that refers to components whose constituents are not generally provided or quantified. Examples of an "undefined component" include, without limitation, human serum (e.g., human serum AB) and fetal serum (e.g., fetal bovine serum or fetal calf serum).

As used herein, "+", when used to indicate the presence of a particular cellular marker, means that the cellular marker is detectably present in fluorescence activated cell sorting over an isotype control; or is detectable above background in quantitative or semi-quantitative RT-PCR.

As used herein, "−", when used to indicate the presence of a particular cellular marker, means that the cellular marker is not detectably present in fluorescence activated cell sorting over an isotype control; or is not detectable above background in quantitative or semi-quantitative RT-PCR.

5. BRIEF DESCRIPTION OF THE FIGURES

FIG. 1: Fold expansion of NK cells differentiated from hematopoietic stem cells (HSCs) with various medium formulations. Error bars represent standard derivation from three donors. X axis: day (D) of culture. Y axis: fold-expansion compared to day 0 (start of culture).

Figure 2:
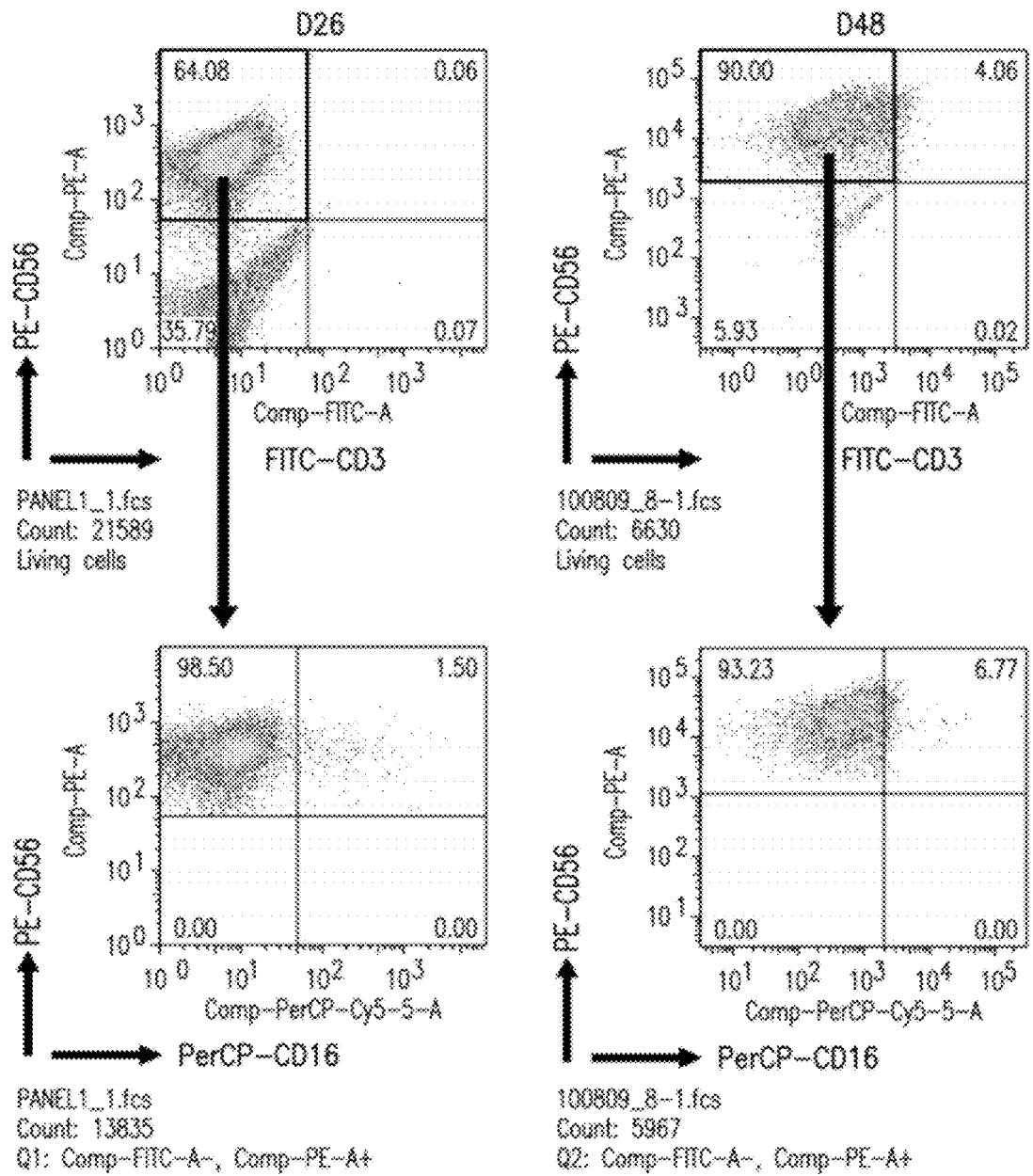

FIG. 2: Phenotypic characterization of cultivated NK cells with NK2A medium. Cells were triple-labeled with PE-antiCD56, FITC-antiCD3, PerCP-antiCD16. Horizontal, vertical lines: level of fluorescent label significantly above background.

Figure 3:
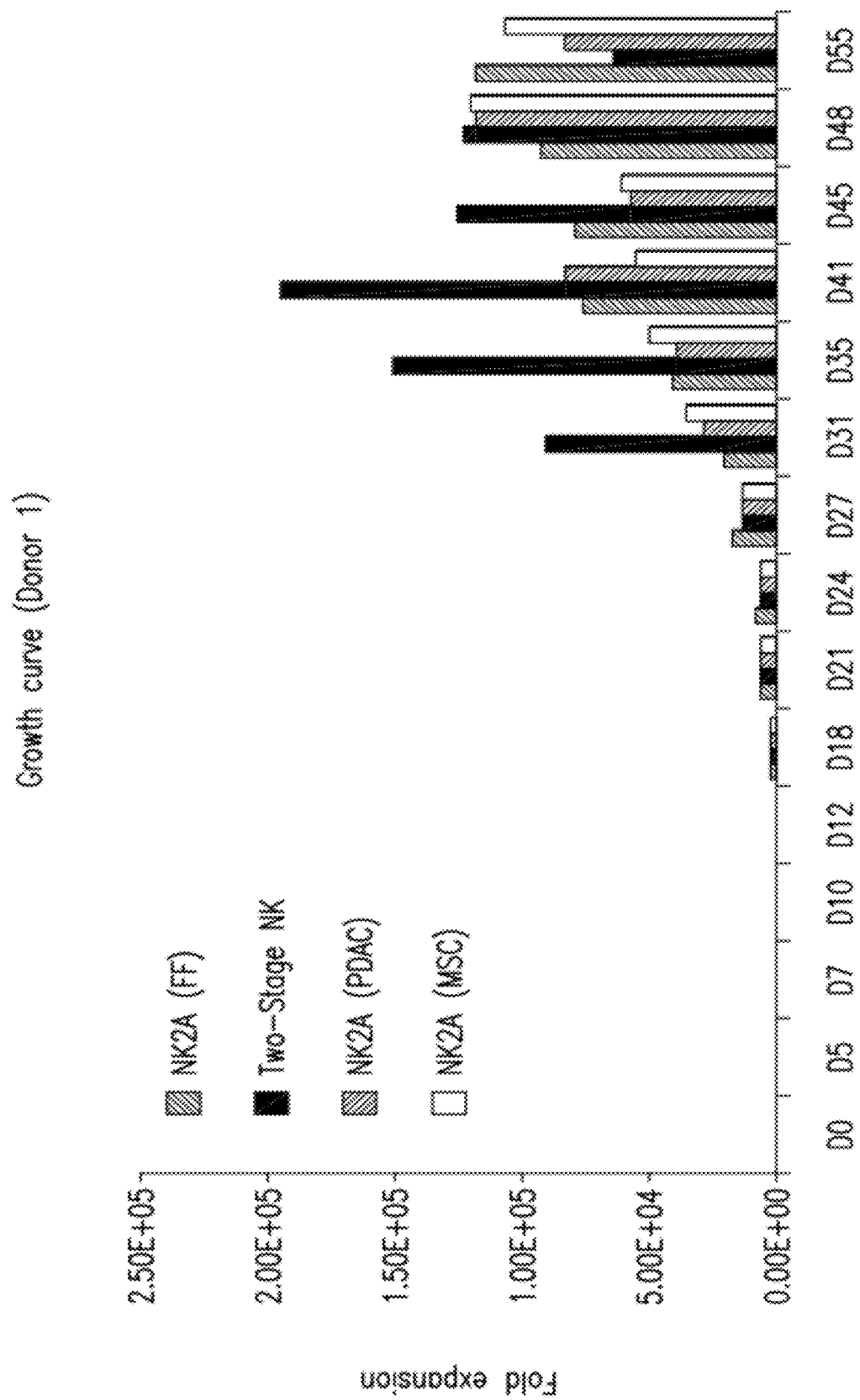

FIG. 3: Fold expansion of NK cells cultivated with NK2A (FF), NK2A (placental stem cells as feeder cells), NK2A (MSC as feeder cells) or Two-stage NK medium. X axis: day (D) of culture. Y axis: fold-expansion compared to day 0 (start of culture).

Figure 4:
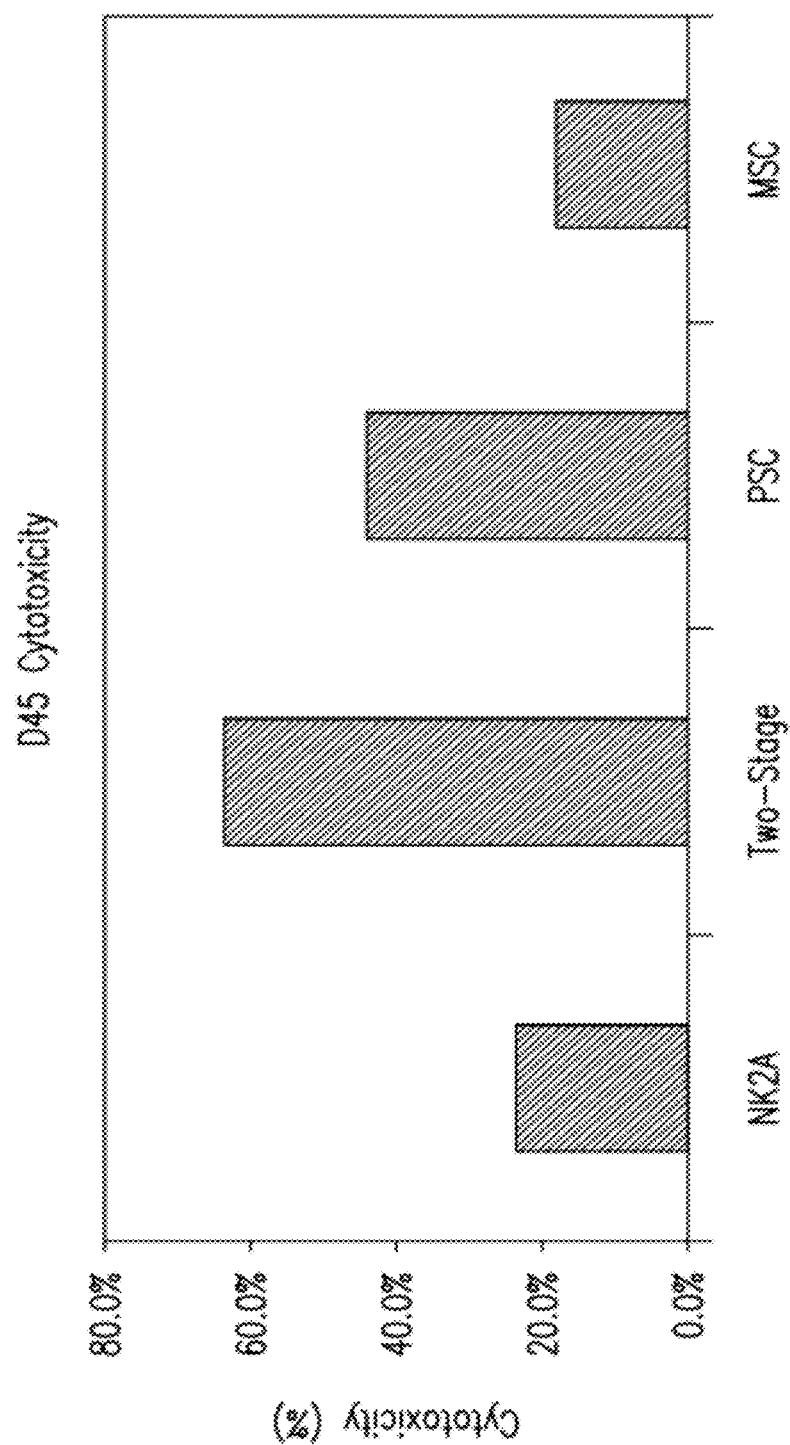

FIG. 4: Cytotoxicity of NK cells cultivated with NK2A (without feeder cells), Two-stage NK medium; NK2A with $CD34^-$, $CD10^+$, $CD105^+$, $CD200^+$ tissue culture plastic-adherent placental stem cells (PSC) as feeder cells, NK2A with bone marrow-derived mesenchymal stem cells (MSC) as feeder cells, at Day 45 post-culture initiation. Representative data from three donors are shown in FIG. 4.

Figure 5:
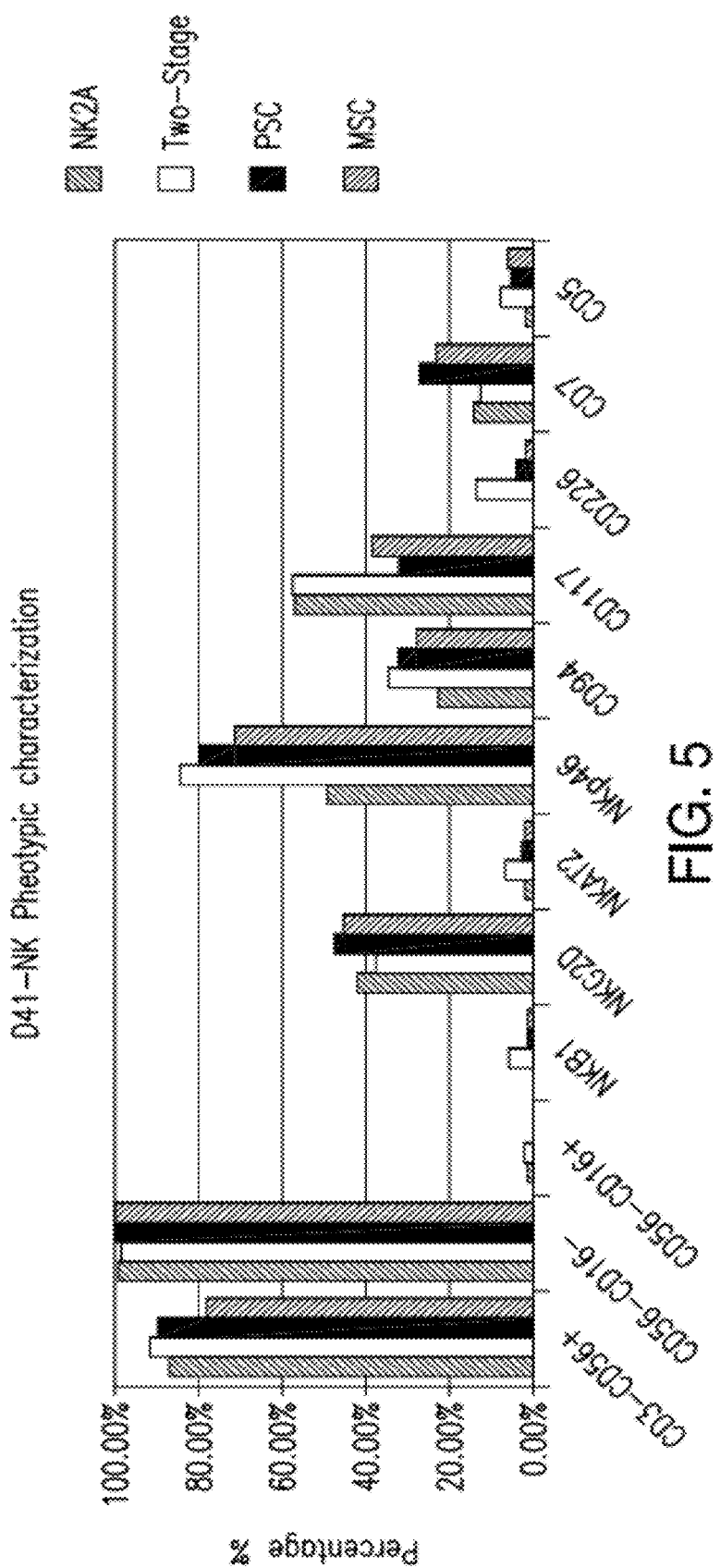

FIG. 5: Phenotypic characterization of NK cells on Day 41 (D41) of culture. Representative data from 3 individual donors are shown. X axis: percentage of NK cells, produced by the two-stage method, that are $CD3^-CD56^+$, $CD16^-CD56^+$, or $CD16^+CD56^+$; or that express NKB1, NKG2D, NKp46, CD94, CD117, CD226, CD7 or CD5. Cells were cultured in NK2A (without feeder cells), Two-stage NK medium; NK2A with $CD34^-$, $CD10^+$, $CD105^+$, $CD200^+$ tissue culture plastic-adherent placental stem cells (PSC) as feeder cells, NK2A with bone marrow-derived mesenchymal stem cells (MSC) as feeder cells, at Day 41 post-culture initiation.

Figure 6:
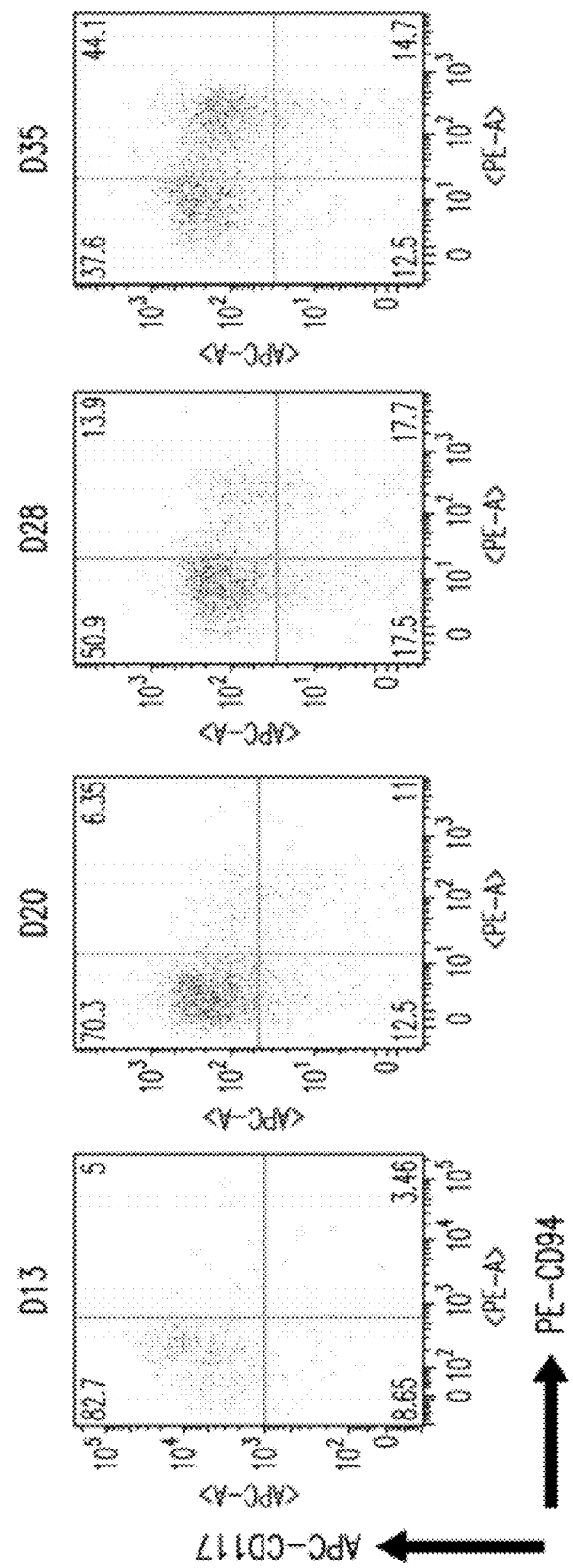

FIG. 6: Expression of CD94 and CD117 in the $CD56^+$ $CD3^-$ NK cell population during NK cultivation in NK2A medium. The dominant population of $CD56^+CD94^+CD117^+$ cells was identified from cultured NK cells in NK2A medium, which is distinguishable from embryonic stem cell (ESC)-derived NK cells ($CD56^+CD94^+CD117^{low/-}$). Representative data from three donors are shown in FIG. 6. X axis: fluorescence from phycoerythrin (PE)-labeled anti-CD94. Y-axis: fluorescence from APC-labeled antiCD117. Horizontal, vertical lines: level of fluorescent label significantly above background. D13, D20, D28, D35: Days 13, 20, 28 and 35 post $CD34^+$ cell culture initiation.

Figure 7:
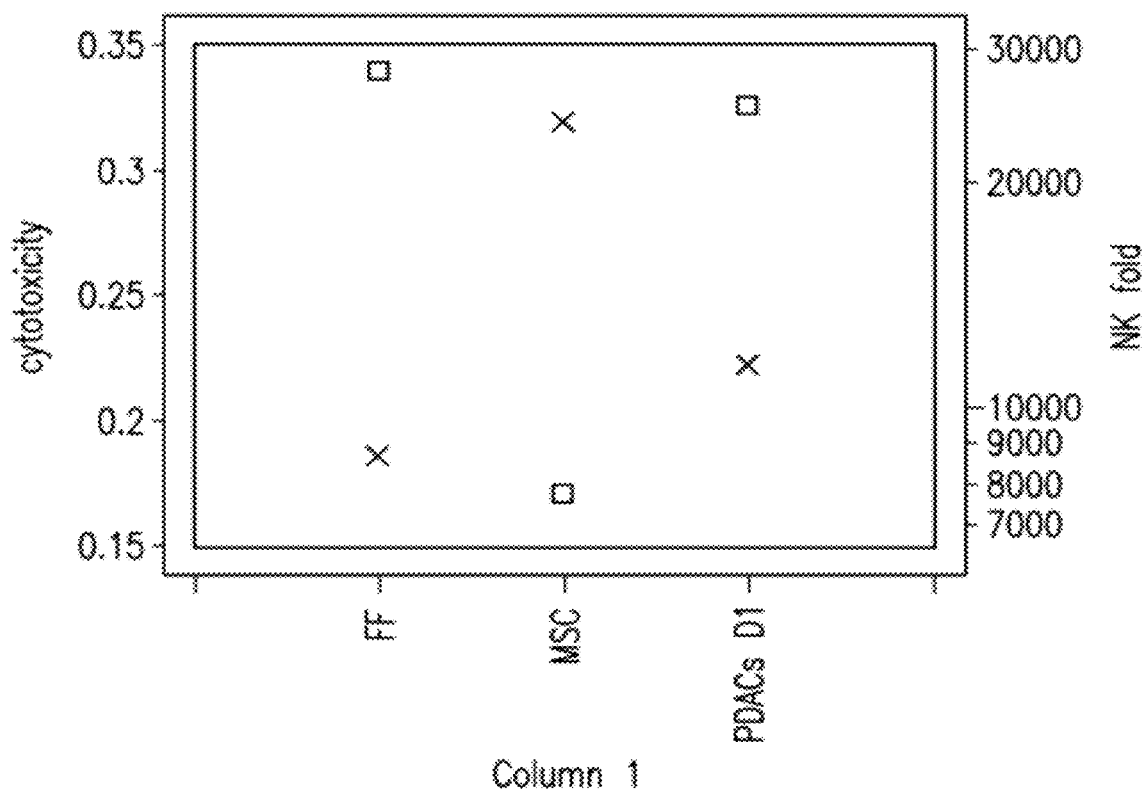

FIG. 7: Effects of placental stem cells on cultured NK cells in comparison with MSC and NK2A medium alone. X axis: NK cells cultured in NK2A medium without a feeder layer (FF); NK cells cultured in NK2A medium with bone marrow-derived mesenchymal stem cells (MCS) as a feeder layer; or NK2A medium with $CD10^+$, $CD34^-$, $CD105^+$, $CD200^+$ tissue culture plastic-adherent placental stem cells (PDACs) as a feeder layer. Y axis (left): cytotoxicity, expressed as a percentage of tumor cells remaining (1.0=100%); cytotoxicity indicated by open squares. Y axis (right): fold expansion of NK cells using the two-step method; fold expansion expressed as asterisks.

Figure 8A:
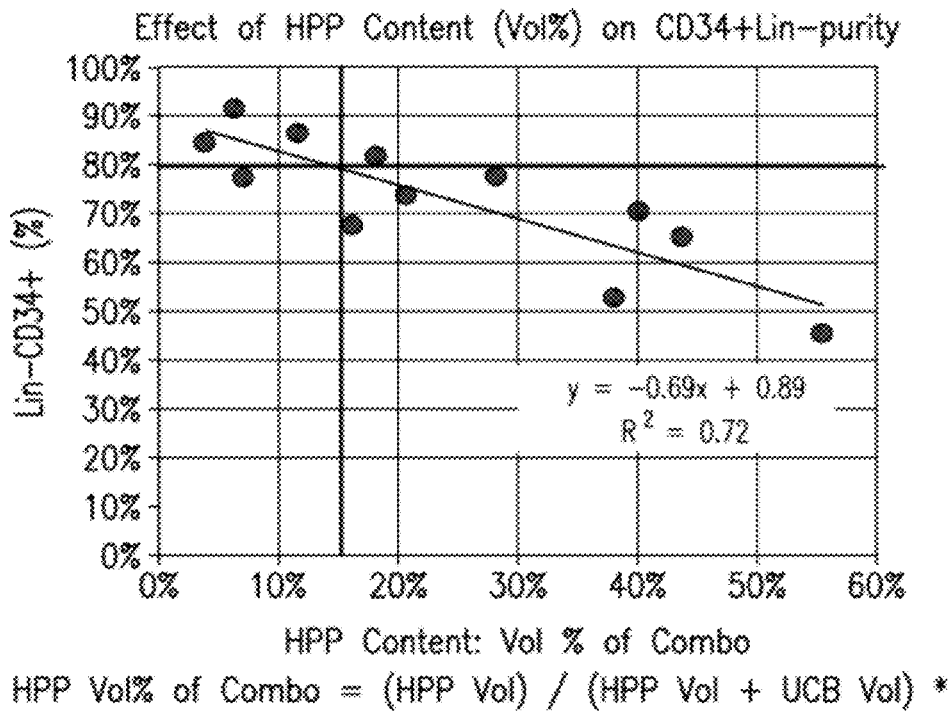
Figure 8B:
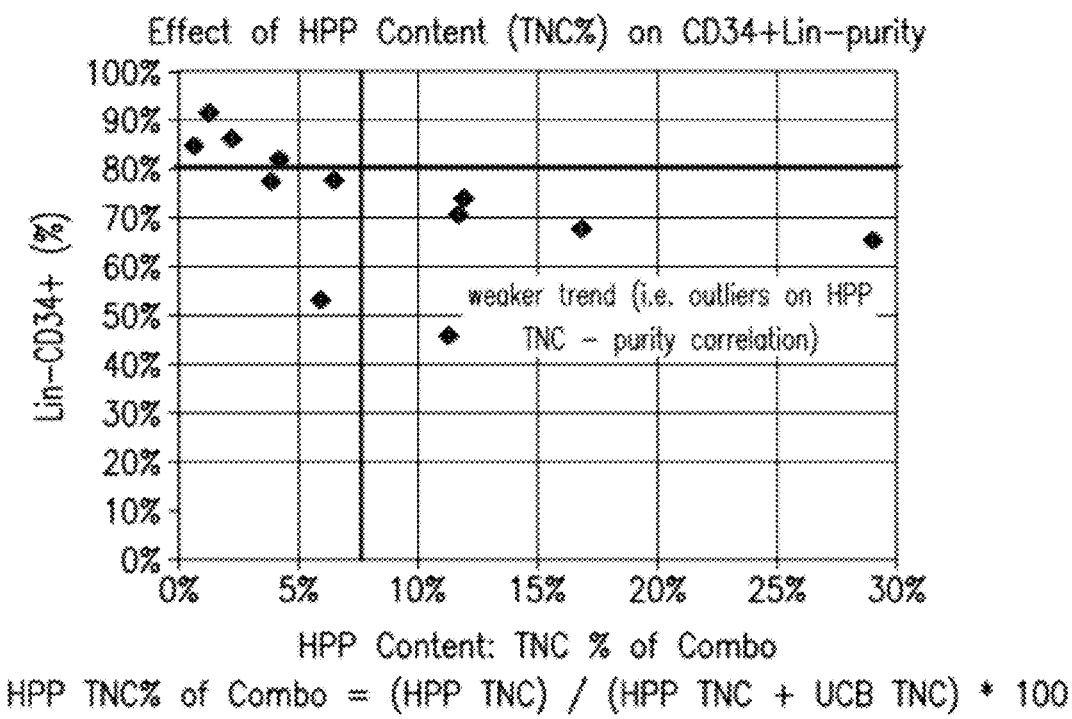

FIGS. 8A-8B: Effects of relative ratios of umbilical cord blood (UCB) and human placentla perfusate (HPP) on the purity of Post-thaw $CD34^+$ cells. FIG. 8A: Effects of HPP volumetric content (vol %) on $CD34^+Lin^-$ purity. X axis: volumetric fraction of HPP in the pooled UCB and HPP (Combo). Y axis: the percentage of $CD34^+Lin^-$ cells. FIG. 8B. Effects of HPP TNC content (TNC %) on $CD34^+Lin^-$ purity. Y axis: the percentage of $CD34^+Lin^-$ cells.

6. DETAILED DESCRIPTION

Provided herein is a novel method of producing and expanding NK cells from hematopoietic cells, e.g., hematopoietic stem cells or progenitor cells. The hematopoietic cells used to produce the NK cells may be isolated from any source, for example, without limitation, placenta, umbilical cord blood, placental blood, peripheral blood, spleen or liver. In certain embodiment, the NK cells are produced from expanded hematopoietic cells, e.g., hematopoietic stem cells and/or hematopoietic progenitor cells. In one embodiment, hematopoietic cells are collected from a source of such cells, e.g., placental perfusate, umbilical cord blood, placental blood, peripheral blood, spleen, liver and/or bone marrow. In a specific embodiment, the hematopoietic cells are expanded and differentiated, continuously, in a first medium without the use of feeder cells. The cells are then cultured in a second medium in the presence of feeder cells. Such isolation, expansion and differentiation can be performed in a central facility, which provides expanded hematopoietic cells for shipment to decentralized expansion and differentiation at points of use, e.g., hospital, military base, military front line, or the like.

6.1. Hematopoietic Cells

Hematopoietic cells useful in the methods disclosed herein can be any hematopoietic cells able to differentiate into NK cells, e.g., precursor cells, hematopoietic progenitor cells, hematopoietic stem cells, or the like. Hematopoietic cells can be obtained from tissue sources such as, e.g., bone marrow, cord blood, placental blood, peripheral blood, liver or the like, or combinations thereof. Hematopoietic cells can be obtained from placenta. In a specific embodiment, the hematopoietic cells are obtained from placental perfusate. Hematopoietic cells from placental perfusate can comprise a mixture of fetal and maternal hematopoietic cells, e.g., a mixture in which maternal cells comprise greater than 5% of the total number of hematopoietic cells. Preferably, hematopoietic cells from placental perfusate comprise at least about 90%, 95%, 98%, 99% or 99.5% fetal cells.

In another specific embodiment, the hematopoietic cells, e.g., hematopoietic stem cells or progenitor cells, from which the TSNK cells are produced, are obtained from placental perfusate, umbilical cord blood or peripheral blood. In another specific embodiment, the hematopoietic cells, e.g., hematopoietic stem cells or progenitor cells, from which the TSNK cells are produced, are combined cells from placental perfusate and cord blood, e.g., cord blood from the same placenta as the perfusate. In another specific embodiment, said umbilical cord blood is isolated from a placenta other than the placenta from which said placental perfusate is obtained. In certain embodiments, the combined cells can be obtained by pooling or combining the cord blood and placental perfusate. In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by volume to obtain the combined cells. In a specific embodiment, the cord blood and placental perfusate are combined at a ratio of from 10:1 to 1:10, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10. In a more specific embodiment, the cord blood and placental perfusate are combined at a ratio of 8.5:1.5 (85%: 15%).

In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by total nucleated cells (TNC) content to obtain the combined cells. In a specific embodiment, the cord blood and placental perfusate are combined at a ratio of from 10:1 to 10:1, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10.

In another specific embodiment, the hematopoietic cells, e.g., hematopoietic stem cells or progenitor cells from which said TSNK cells are produced are from both umbilical cord blood and placental perfusate, but wherein said umbilical cord blood is isolated from a placenta other than the placenta from which said placental perfusate is obtained.

In certain embodiments, the hematopoietic cells are $CD34^+$ cells. In specific embodiments, the hematopoietic cells useful in the methods disclosed herein are $CD34^+CD38^+$ or $CD34^+CD38^-$. In a more specific embodiment, the hematopoietic cells are $CD34^+CD38^-Lin^-$. In another specific embodiment, the hematopoietic cells are one or more of $CD2^-$, $CD3^-$, $CD11b^-$, $CD11c^-$, $CD14^-$, $CD16^-$, $CD19^-$, $CD24^-$, $CD56^-$, $CD66b^-$ and/or glycophorin K. In another specific embodiment, the hematopoietic cells are $CD2^-$, $CD3^-$, $CD11b^-$, $CD11c^-$, $CD14^-$, $CD16^-$, $CD19^-$, $CD24^-$, $CD56^-$, $CD66b^-$ and glycophorin K. In another more specific embodiment, the hematopoietic cells are $CD34^+CD38^-CD33^-CD117^-$. In another more specific embodiment, the hematopoietic cells are $CD34^+CD38^-CD33^-CD117^-CD235^-CD36^-$.

In another embodiment, the hematopoietic cells are $CD45^+$. In another specific embodiment, the hematopoietic cells are $CD34^+CD45^+$. In another embodiment, the hematopoietic cell is $Thy-1^+$. In a specific embodiment, the hematopoietic cell is $CD34^+Thy-1^+$. In another embodiment, the hematopoietic cells are $CD133^+$. In specific embodiments, the hematopoietic cells are $CD34^+CD133^+$ or $CD133^+Thy-1^+$. In another specific embodiment, the $CD34^+$ hematopoietic cells are $CXCR4^+$. In another specific embodiment, the $CD34^+$ hematopoietic cells are $CXCR4^-$. In another embodiment, the hematopoietic cells are positive for KDR (vascular growth factor receptor 2). In specific embodiments, the hematopoietic cells are $CD34^+KDR^+$, $CD133^+KDR^+$ or $Thy-1^+KDR^+$. In certain other embodiments, the hematopoietic cells are positive for aldehyde dehydrogenase ($ALDH^+$), e.g., the cells are $CD34^+ ALDH^+$.

In certain other embodiments, the $CD34^+$ cells are $CD45^-$. In specific embodiments, the $CD34^+$ cells, e.g., $CD34^+$, $CD45^-$ cells express one or more, or all, of the miRNAs hsa-miR-380, hsa-miR-512, hsa-miR-517, hsa-miR-518c, hsa-miR-519b, and/or hsa-miR-520a.

In certain embodiments, the hematopoietic cells are $CD34^-$.

The hematopoietic cells can also lack certain markers that indicate lineage commitment, or a lack of developmental naiveté. For example, in another embodiment, the hematopoietic cells are $HLA-DR^-$. In specific embodiments, the hematopoietic cells are $CD34^+HLA-DR^-$, $CD133^+HLA-DR^-$, $Thy-1^+HLA-DR^-$ or $ALDH^+HLA-DR^-$ In another embodiment, the hematopoietic cells are negative for one or more, preferably all, of lineage markers CD2, CD3, CD11b, CD11c, CD14, CD16, CD19, CD24, CD56, CD66b and glycophorin A.

Thus, hematopoietic cells can be selected for use in the methods disclosed herein on the basis of the presence of markers that indicate an undifferentiated state, or on the basis of the absence of lineage markers indicating that at least some lineage differentiation has taken place. Methods of isolating cells, including hematopoietic cells, on the basis of the presence or absence of specific markers is discussed in detail, e.g., in Section 6.1.2, below.

Hematopoietic cells used in the methods provided herein can be a substantially homogeneous population, e.g., a population comprising at least about 95%, at least about 98% or at least about 99% hematopoietic cells from a single tissue source, or a population comprising hematopoietic cells exhibiting the same hematopoietic cell-associated cellular markers. For example, in various embodiments, the hematopoietic cells can comprise at least about 95%, 98% or 99% hematopoietic cells from bone marrow, cord blood, placental blood, peripheral blood, or placenta, e.g., placenta perfusate.

Hematopoietic cells used in the methods provided herein can be obtained from a single individual, e.g., from a single placenta, or from a plurality of individuals, e.g., can be pooled. Where the hematopoietic cells are obtained from a plurality of individuals and pooled, the hematopoietic cells may be obtained from the same tissue source. Thus, in various embodiments, the pooled hematopoietic cells are all from placenta, e.g., placental perfusate, all from placental blood, all from umbilical cord blood, all from peripheral blood, and the like.

Hematopoietic cells used in the methods disclosed herein can, in certain embodiments, comprise hematopoietic cells from two or more tissue sources. For example, in certain embodiments, when hematopoietic cells from two or more sources are combined for use in the methods herein, a plurality of the hematopoietic cells used to produce TSNK cells comprise hematopoietic cells from placenta, e.g., placenta perfusate. In various embodiments, the hematopoietic cells used to produce TSNK cells comprise hematopoietic cells from placenta and from cord blood; from placenta and peripheral blood; from placenta and placental blood, or placenta and bone marrow. In a preferred embodiment, the hematopoietic cells comprise hematopoietic cells from placental perfusate in combination with hematopoietic cells from cord blood, wherein the cord blood and placenta are from the same individual, i.e., wherein the perfusate and cord blood are matched. In embodiments in which the hematopoietic cells comprise hematopoietic cells from two tissue sources, the hematopoietic cells from the sources can be combined in a ratio of, for example, 1:10, 2:9, 3:8, 4:7: 5:6, 6:5, 7:4, 8:3, 9:2, 1:10, 1:9, 1:8, 1:7, 1:6, 1:5, 1:4, 1:3, 1:2, 1:1, 2:1, 3:1, 4:1, 5:1, 6:1, 7:1, 8:1 or 9:1.

6.1.1. Placental Hematopoietic Stem Cells

In certain embodiments, the hematopoietic cells used in the methods provided herein are placental hematopoietic cells. As used herein, "placental hematopoietic cells" means hematopoietic cells obtained from the placenta itself, and not from placental blood or from umbilical cord blood. In one embodiment, placental hematopoietic cells are $CD34^+$. In a specific embodiment, the placental hematopoietic cells are predominantly (e.g., at least about 50%, 55%, 60%, 65%, 70%, 75%, 80%, 85%, 90%, 95% or 98%) $CD34^+CD38^-$ cells. In another specific embodiment, the placental hematopoietic cells are predominantly (e.g., at least about 50%, 55%, 60%, 65%, 70%, 75%, 80%, 85%, 90%, 95% or 98%) $CD34^+CD38^+$ cells. Placental hematopoietic cells can be obtained from a post-partum mammalian (e.g., human) placenta by any means known to those of skill in the art, e.g., by perfusion.

In another embodiment, the placental hematopoietic cell is $CD45^-$. In a specific embodiment, the hematopoietic cell is $CD34^+CD45^-$. In another specific embodiment, the placental hematopoietic cells are $CD34^+CD45^+$.

6.2. Production of Natural Killer Cells

Production of NK cells by the present method comprises expanding a population of hematopoietic cells. During cell expansion, a plurality of hematopoietic cells within the hematopoietic cell population differentiate into NK cells.

In one embodiment, provided herein is a method of producing a population of activated natural killer (NK) cells, comprising: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; and (b) expanding the cells from step (a) in a second medium comprising interleukin-2 (IL-2), to produce a population of activated NK cells.

In another embodiment, NK cells provided herein are produced by a two-step process of expansion/differentiation and maturation of NK cells. The fist and second steps comprise culturing the cells in media with a unique combination of cellular factors. In certain embodiments, the process involves (a) culturing and expanding a population of hematopoietic cells in a first medium, wherein a plurality of hematopoietic stem or progenitor cells within the hematopoietic cell population differentiate into NK cells; and (b) expanding the NK cells from step (a) in a second medium, wherein the NK cells are further expanded and differentiated, and wherein the NK cells are maturated (e.g., activated or otherwise possessing cytotoxic activity). In certain embodiments, the method includes no intermediary steps between step (a) and (b), no additional culturing steps prior to step (a), and/or no additional steps (e.g., maturation step) after step (b).

6.2.1. First Culturing Step

In certain embodiments, the methods provided herein comprises a first step of culturing and expanding a population of hematopoietic cells in a first medium, wherein a plurality of hematopoietic stem or progenitor cells within the hematopoietic cell population differentiate into NK cells.

Without wishing to be bound by any parameter, mechanism or theory, culture of the hematopoietic cells as provided herein results in continuous expansion of the hematopoietic cells and differentiation of NK cells from said cells. In certain embodiments, hematopoietic cells, e.g., stem cells or progenitor cells, used in the methods provided herein are expanded and differentiated in the first step using a feeder layer. In other embodiments, hematopoietic cells, e.g., stem cells or progenitor cells, are expanded and differentiated in the first step without the use of a feeder layer.

Feeder cell-independent expansion and differentiation of hematopoietic cells can take place in any container compatible with cell culture and expansion, e.g., flask, tube, beaker, dish, multiwell plate, bag or the like. In a specific embodiment, feeder cell-independent expansion of hematopoietic cells takes place in a bag, e.g., a flexible, gas-permeable fluorocarbon culture bag (for example, from American Fluoroseal). In a specific embodiment, the container in which the hematopoietic cells are expanded is suitable for shipping, e.g., to a site such as a hospital or military zone wherein the expanded NK cells are further expanded and differentiated.

In certain embodiments, hematopoietic cells are expanded and differentiated, e.g., in a continuous fashion, in a first culture medium. In one embodiment, the first culture medium is an animal-component free medium. Exemplary animal component-free media useful in the methods provided herein include, but are not limited to, Basal Medium Eagle (BME), Dulbecco's Modified Eagle's Medium (DMEM), Glasgow Minimum Essential Medium (GMEM), Dulbecco's Modified Eagle's Medium/Nutrient Mixture F-12 Ham (DMEM/F-12), Minimum Essential Medium (MEM), Iscove's Modified Dulbecco's Medium (IMDM), Nutrient Mixture F-10 Ham (Ham's F-10), Nutrient Mixture F-12 Ham (Ham's F-12), RPMI-1640 Medium, Williams' Medium E, STEMSPAN® (Cat. No. Stem Cell Technologies, Vancouver, Canada), Glycostem Basal Growth Medium (GBGM®), AIM-V® medium (Invitrogen), X-VIVO™ 10 (Lonza), X-VIVO™ 15 (Lonza), OPTMIZER (Invitrogen), STEMSPAN® H3000 (STEMCELL Technologies), CELLGRO COMPLETE™ (Mediatech), or any modified variants or combinations thereof.

In preferred embodiments, the first culture medium comprises one or more of medium supplements (e.g., nutrients, cytokines and/or factors). Medium supplements suitable for use in the methods provided herein include, for example without limitation, serum such as human serum AB, fetal bovine serum (FBS) or fetal calf serum (FCS), vitamins, bovine serum albumin (BSA), amino acids (e.g., L-glutamine), fatty acids (e.g., oleic acid, linoleic acid or palmitic acid), insulin (e.g., recombinant human insulin), transferrin (iron saturated human transferrin), β-mercaptoethanol, stem cell factor (SCF), Fms-like-tyrosine kinase 3 ligand (Flt3-L), cytokines such as interleukin-2 (IL-2), interleukin-7 (IL-7), interleukin-15 (IL-15), thrombopoietin (Tpo), heparin, or O-acetyl-carnitine (also referred to as acetylcarnitine, O-acetyl-L-carnitine or OAC). In a specific embodiment, the medium used herein comprises human serum AB. In another specific embodiment, the medium used herein comprises FBS.

In another specific embodiment, the medium used herein comprises OAC. In certain embodiments, the first medium does not comprise one or more of, granulocyte colony-stimulating factor (G-CSF), granulocyte/macrophage colony stimulating factor (GM-CSF), interleukin-6 (IL-6), macrophage inflammatory Protein 1α (MIP1α), or leukemia inhibitory factor (LIF).

Thus, in one aspect, provided herein is a two-step method of producing NK cells, wherein said first step comprises expanding and differentiating a population of hematopoietic cells in a first culture medium in the absence of feeder cells, wherein a plurality of hematopoietic cells within said population of hematopoietic cells differentiate into NK cells during said expanding, and wherein the medium comprises SCF at a concentration of about 1 to about 150 ng/mL, IL-2 at a concentration of about 50 to about 1500 IU/mL, IL-7 at a concentration of about 1 to about 150 ng/mL, IL-15 at a concentration 1 to about 150 ng/mL and heparin at a concentration of about 0.1 to about 30 IU/mL, and wherein said SCF, IL-2, IL-7, IL-15 and heparin are not comprised within an undefined component of said medium (e.g., serum). In certain embodiments, said medium comprises one or more of O-acetyl-carnitine (also referred to as acetylcarnitine, O-acetyl-L-carnitine or OAC), or a compound that affects acetyl-CoA cycling in mitodronia, thiazovivin, Y-27632, pyintegrin, Rho kinase (ROCK) inhibitors, caspase inhibitors or other anti-apoptotic compounds/peptides, NOVA-RS (Sheffield Bio-Science) or other small-molecule growth enhancers. In certain embodiments, said medium comprises nicotinamide. In certain embodiments, said medium comprises about 0.5 mM-10 mM OAC. In one embodiment, said medium comprises Stemspan® H3000, and/or DMEM:F12 and about 0.5, 1, 2, 3, 4, 5, 6, 7, 8, 9, or 10 mM OAC. In a specific embodiment of the method, said medium is GBGM®. In another specific embodiment, said medium comprises Stemspan® H3000 and about 5 mM of OAC. In another specific embodiment, said medium comprises DMEM:F12 and about 5 mM of OAC. The OAC can be added anytime during the culturing methods provided herein. In certain embodiments, said OAC is added to the first medium and/or during the first culturing step. In some embodiments, said OAC is added to the first medium on Day 0, 1, 2, 3, 4, 5, 6, 7, 8, 9, 10, 11, 12, 13, 14, 15, 16, 17, 18, 19, 20, 21 of the culture. In a specific embodiment, said OAC is added to the first medium on Day 7 of the first culturing step. In a more specific embodiment, said OAC is added to the first medium on Day 7 of the culture and is present throughout the first and second culturing steps. In certain embodiments, said OAC is added to the second medium and/or during the second culturing step. In some embodiments, said OAC is added to the second medium on Day 22, 23, 24, 25, 26, 27, 28, 29, 30, 31, 32, 33, 34, of the culture.

In another specific embodiment, said medium is IMDM supplemented with about 5-20% BSA, about 1-10 µg/mL recombinant human insulin, about 10-50 µg/mL iron saturated human transferrin and about 10-50 µM β-mercaptoethanol. In another specific embodiment, said medium does not comprise one or more, or any, of IL-11, IL-3, homeobox-B4 (HoxB4), and/or methylcellulose.

In other specific embodiments, said medium comprises SCF at a concentration of about 0.1 to about 500 ng/mL; about 5 to about 100 ng/mL; or about 20 ng/mL. In other specific embodiments, said medium comprises IL-2 at a concentration of about 10 to about 2000 IU/mL; or about 100 to about 500 IU/mL; or about 200 IU/mL. In other specific embodiments, said medium comprises IL-7 at a concentration of about 0.1 to about 500 ng/mL; about 5 to about 100 ng/mL; or about 20 ng/mL. In other specific embodiments, said medium comprises IL-15 at a concentration of about 0.1 to about 500 ng/mL; about 5 to about 100 ng/mL; or about 10 ng/mL. In other specific embodiments, said medium comprises heparin at concentration of about 0.05 to about 100 U/mL; or about 0.5 to about 20 U/ml; or about 1.5 U/mL.

In yet other specific embodiment of the method, said medium further comprises Fms-like-tyrosine kinase 3 ligand (Flt-3L) at a concentration of about 1 to about 150 ng/mL, thrombopoietin (Tpo) at a concentration of about 1 to about 150 ng/mL, or a combination of both. In other specific embodiments, said medium comprises Flt-3L at a concentration of about 0.1 to about 500 ng/mL; about 5 to about 100 ng/mL; or about 20 ng/mL. In other specific embodiments, said medium comprises Tpo at a concentration of about 0.1 to about 500 ng/mL; about 5 to about 100 ng/mL; or about 20 ng/mL.

In a more specific embodiment of the method, the first culture medium is GBGM®, which comprises about 20 ng/mL SCF, about 20 ng/mL IL-7, about 10 ng/mL IL-15. In another more specific embodiment of the method, the first culture medium is GBGM®, which comprises about 20 ng/mL SCF, about 20 ng/mL Flt3-L, about 200 IU/mL IL-2, about 20 ng/mL IL-7, about 10 ng/mL IL-15, about 20 ng/mL Tpo, and about 1.5 U/mL heparin. In another specific embodiment, said first culture medium further comprises 10% human serum (e.g., human serum AB) or fetal serum (e.g., FBS).

In another embodiment, hematopoietic cells are expanded by culturing said cells, e.g., in said first medium, in contact with an immunomodulatory compound, e.g., a TNF-α inhibitory compound, for a time and in an amount sufficient to cause a detectable increase in the proliferation of the hematopoietic cells over a given time, compared to an equivalent number of hematopoietic cells not contacted with the immunomodulatory compound. See, e.g., U.S. Patent Application Publication No. 2003/0235909, the disclosure of which is hereby incorporated by reference in its entirety. In certain embodiments, the immunomodulatory compound is an amino-substituted isoindoline. In a preferred embodiment, the immunomodulatory compound is 3-(4-amino-1-oxo-1,3-dihydroisoindol-2-yl)-piperidine-2,6-dione; 3-(4'aminoisolindoline-1'-one)-1-piperidine-2,6-dione; 4-(amino)-2-(2,6-dioxo(3-piperidyl))-isoindoline-1,3-dione; or 4-Amino-2-(2,6-dioxopiperidin-3-yl)isoindole-1,3-dione. In another preferred embodiment, the immunomodulatory compound is pomalidomide, or lenalidomide. In another embodiment, said immunomodulatory compound is a compound having the structure

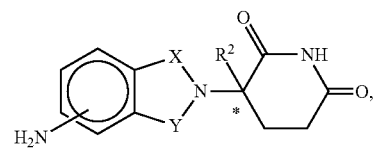

wherein one of X and Y is C=O, the other of X and Y is C=O or $CH_2$, and $R^2$ is hydrogen or lower alkyl, or a pharmaceutically acceptable salt, hydrate, solvate, clathrate, enantiomer, diastereomer, racemate, or mixture of stereoisomers thereof. In another embodiment, said immunomodulatory compound is a compound having the structure

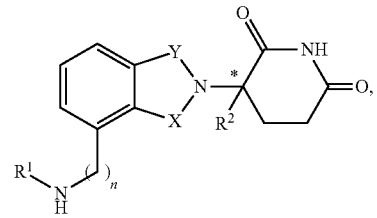

wherein one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$ alkyl-C(O)OR⁵, C(O)NHR³, C(S)NHR³, C(O)NR³R³', C(S)NR³R³' or (C₁-C₈)alkyl-O(CO)R⁵;

R² is H, F, benzyl, (C₁-C₈)alkyl, (C₂-C₈)alkenyl, or (C₂-C₈)alkynyl;

R³ and R³' are independently (C₁-C₈)alkyl, (C₃-C₇)cycloalkyl, (C₂-C₈)alkenyl, (C₂-C₈)alkynyl, benzyl, aryl, (C₀-C₄)alkyl-(C₁-C₆)heterocycloalkyl, (C₀-C₄)alkyl-(C₂-C₅)heteroaryl, (C₀-C₈)alkyl-N(R⁶)₂, (C₁-C₈)alkyl-OR⁵, (C₁-C₈)alkyl-C(O)OR⁵, (C₁-C₈)alkyl-O(CO)R⁵, or C(O)OR⁵;

R⁴ is (C₁-C₈)alkyl, (C₂-C₈)alkenyl, (C₂-C₈)alkynyl, (C₁-C₄)alkyl-OR⁵, benzyl, aryl, (C₀-C₄)alkyl-(C₁-C₆)heterocycloalkyl, or (C₀-C₄)alkyl-(C₂-C₅)heteroaryl;

R⁵ is (C₁-C₈)alkyl, (C₂-C₈)alkenyl, (C₂-C₈)alkynyl, benzyl, aryl, or (C₂-C₅)heteroaryl;

each occurrence of R⁶ is independently H, (C₁-C₈)alkyl, (C₂-C₈)alkenyl, (C₂-C₈)alkynyl, benzyl, aryl, (C₂-C₅)heteroaryl, or (C₀-C₈)alkyl-C(O)O—R⁵ or the R⁶ groups can join to form a heterocycloalkyl group;

n is 0 or 1; and

* represents a chiral-carbon center;

or a pharmaceutically acceptable salt, hydrate, solvate, clathrate, enantiomer, diastereomer, racemate, or mixture of stereoisomers thereof. In another embodiment, said immunomodulatory compound is a compound having the structure

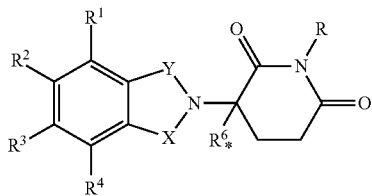

wherein:
one of X and Y is C=O and the other is CH₂ or C=O;
R is H or CH₂OCOR';
(i) each of R¹, R², R³, or R⁴, independently of the others, is halo, alkyl of 1 to 4 carbon atoms, or alkoxy of 1 to 4 carbon atoms or (ii) one of R¹, R², R³, or R⁴ is nitro or —NHR⁵ and the remaining of R¹, R², R³, or R⁴ are hydrogen;
R⁵ is hydrogen or alkyl of 1 to 8 carbons
R⁶ hydrogen, alkyl of 1 to 8 carbon atoms, benzo, chloro, or fluoro;
R' is R⁷—CHR¹⁰—N(R⁸R⁹);
R⁷ is m-phenylene or p-phenylene or —(CₙH₂ₙ)— in which n has a value of 0 to 4;
each of R⁸ and R⁹ taken independently of the other is hydrogen or alkyl of 1 to 8 carbon atoms, or R⁸ and R⁹ taken together are tetramethylene, pentamethylene, hexamethylene, or —CH₂CH₂X₁CH₂CH₂— in which X₁ is —O—, —S—, or —NH—;
R¹⁰ is hydrogen, alkyl of to 8 carbon atoms, or phenyl; and
* represents a chiral-carbon center;
or a pharmaceutically acceptable salt, hydrate, solvate, clathrate, enantiomer, diastereomer, racemate, or mixture of stereoisomers thereof.

In a specific embodiment, expansion of the hematopoietic cells is performed in IMDM supplemented with 20% BITS (bovine serum albumin, recombinant human insulin and transferrin), SCF, Flt-3 ligand, IL-3, and 4-(Amino)-2-(2,6-dioxo(3-piperidyl))-isoindoline-1,3-dione (10 μM in 0.05% DMSO). In a more specific embodiment, about 5×10⁷ hematopoietic cells, e.g., CD34⁺ cells, are expanded in the medium to from about 5×10¹⁰ cells to about 5×10¹² cells, which are resuspended in 100 mL of IMDM to produce a population of expanded hematopoietic cells. The population of expanded hematopoietic cells is preferably cryopreserved to facilitate shipping.

In various specific embodiments, at least 50%, 55%, 60%, 65%, 70%. 75%, 80%, 85%, 90%, 95%, 97%, 98%, or 99% of the hematopoietic cells are differentiated to NK cells.

In certain embodiments, the method of expansion and differentiation of the hematopoietic cells, as described herein, comprises maintaining the cell population comprising said hematopoietic cells at between about 2×10⁴ and about 2×10⁵ cells per milliliter during expansion and differentiation. In certain other embodiments, the method of expansion and differentiation of the hematopoietic cells, as described herein, comprises maintaining the cell population comprising said hematopoietic cells at no more than about 1×10⁵ cells per milliliter.

The time for expansion and differentiation of hematopoietic cells into NK cells can be, for example, from about 3 days to about 120 days. In one embodiment, the differentiation time is about 7 days to about 75 days. In another embodiment, the differentiation time is about 14 days to about 50 days. In a specific embodiment, the differentiation time is about 21 days to about 28 days.

6.2.2. Second Step

In the method provided herein, the hematopoietic cells, e.g., stem cells or progenitor cells, and natural killer cells, resulting from the first step, are further expanded and differentiated in a second step, e.g., without the use of feeder layer or in the presence of feeder cells. Culture of the cells as provided herein results in continuous expansion, differentiation as well as maturation of the NK cells from the first step. In the second step, the NK cells are expanded, differentiated and maturated, in a continuous fashion, in a second culture medium, e.g., comprising different cytokines and/or bioactive molecules than said first medium. In certain embodiments, the second culture medium is an animal component-free medium. Exemplary animal component-free cell culture media are described in Section 6.2.1, above.

Thus, in one aspect, provided herein is a method of producing NK cells, comprising expanding the NK cells from the first step, described above, in a second medium in the presence of feeder cells and in contact with interleukin-2 (IL-2). In specific embodiments, said second medium comprises cell growth medium comprising IL-2, e.g., 10 IU/mL to 1000 IU/mL, and one or more of: human serum (e.g., human serum AB), fetal bovine serum (FBS) or fetal calf serum (FCS), e.g., 5%-15% FCS v/v; transferrin, e.g., 10 μg/mL to 50 μg/mL; insulin, e.g., 5 μg/mL to 20 μg/mL; ethanolamine, e.g., 5×10⁻⁴ to 5×10⁻⁵ M; oleic acid, e.g., 0.1 μg/mL to 5 μg/mL; linoleic acid, e.g., 0.1 μg/mL to 5 μg/mL; palmitic acid, e.g., 0.05 μg/mL to 2 μg/mL; bovine serum albumin (BSA), e.g., 1 μg/mL to 5 μg/mL; and/or phytohemagglutinin, e.g., 0.01 μg/mL to 1 μg/mL. In a more specific embodiment, said second medium comprises cell growth medium comprising FBS or FCS, e.g., 10% FCS v/v, IL-2, transferrin, insulin, ethanolamine, oleic acid, linoleic acid, palmitic acid, bovine serum albumin (BSA) and phytohemagglutinin. In a more specific embodiment, said second medium comprises Iscove's Modified Dulbecco's Medium (IMDM), 10% FBS or FCS, 400 IU IL-2, 35 μg/mL transferrin, 5 μg/mL insulin, 2×10⁻⁵ M ethanolamine, 1 μg/mL oleic acid, 1 μg/mL linoleic acid (Sigma-Aldrich), 0.2 μg/mL palmitic acid (Sigma-Aldrich), 2.5 μg/mL BSA (Sigma-Aldrich) and 0.1 μg/mL phytohemagglutinin.

In certain embodiments, the second medium does not comprise one or more of, granulocyte colony-stimulating factor (G-CSF), granulocyte/macrophage colony stimulating factor (GM-CSF), interleukin-6 (IL-6), macrophage inflammatory Protein 1α (MIP1α), or leukemia inhibitory factor (LIF).

In addition to the method, provided herein are any of the media described above as compositions.

Feeder cells, when used, can be established from various cell types. Examples of these cell types include, without limitation, fibroblasts, stem cells (e.g., tissue culture-adherent placental stem cells), blood cells (e.g., peripheral blood mononuclear cells (PBMC)), and cancerous cells (e.g., chronic myelogenous leukemia (CML) cells such as K562). In a specific embodiment, said culturing in said second medium comprises culturing using feeder cells, e.g., K562 cells and/or peripheral blood mononuclear cells (PBMCs), e.g., at the time the cells are started in said second medium, 1, 2, 3, 4, 5, 6, 7, 8, 9 or 10 days thereafter. In certain embodiments, feeder cells are optionally from a different species as the cells they are supporting. For example, human NK cells can be supported by mouse embryonic fibroblasts (from primary culture or a telomerized line).

In certain embodiments, feeder cells are optionally inactivated by irradiation (e.g., γ-irradiation) or treatment with an anti-mitotic agent such as mitomycin C, to prevent them from outgrowing the cells they are supporting, but permit synthesis of important factors that support the NK cells. For example, cells can be irradiated at a dose to inhibit proliferation but permit synthesis of important factors that support human embryonic stem (hES) cells (about 4000 rads gamma irradiation).

Culture of NK cells for the second step can take place in any container compatible with cell culture and expansion, e.g., flask, tube, beaker, dish, multiwell plate, bag or the like. In a specific embodiment, feeder cell-dependent culture of NK cells takes place in a bag, e.g., a flexible, gas-permeable fluorocarbon culture bag (for example, from American Fluoroseal). In a specific embodiment, the container in which the NK cells are cultured is suitable for shipping, e.g., to a site such as a hospital or military zone wherein the expanded NK cells are further expanded, differentiated and matured.

Differentiation of the cells from step 1 into TSNK cells can be assessed by detecting NK cell-specific markers, e.g., by flow cytometry. NK cell-specific markers include, but are not limited to, CD56, CD94, CD117 and NKp46. Differentiation can also be assessed by the morphological characteristics of NK cells, e.g., large size, high protein synthesis activity in the abundant endoplasmic reticulum (ER), and/or preformed granules.

The time for expansion and differentiation of cells from step 1 into TSNK cells can be, for example, from about 3 days to about 120 days. In one embodiment, the differentiation time is about 7 days to about 75 days. In another embodiment, the differentiation time is about 14 days to about 50 days. In a specific embodiment, the differentiation time is about 10 days to about 21 days.

Differentiation of hematopoietic cells into NK cells can be assessed by detecting markers, e.g., CD56, CD94, CD117, NKG2D, DNAM-1 and NKp46, by, for example, flow cytometry. Differentiation can also be assessed by the morphological characteristics of NK cells, e.g., large size, high protein synthesis activity in the abundant endoplasmic reticulum (ER), and/or preformed granules. Maturation of NK cells (e.g., TSNK cells) can be assessed by detecting one or more functionally relevant makers, for example, CD94, CD161, NKp44, DNAM-1, 2B4, NKp46, CD94, KIR, and the NKG2 family of activating receptors (e.g., NKG2D). Maturation of NK cells (e.g., TSNK cells) can also be assessed by detecting specific markers during different developmental stages. For example, in one embodiment, pro-NK cells are $CD34^+$, $CD45RA^+$, $CD10^+$, $CD117^-$ and/or $CD161^-$. In another embodiment, pre-NK cells are $CD34^+$, $CD45RA^+$, $CD10^-$, $CD117^+$, and/or $CD161^-$. In another embodiment, immature NK cells are $CD34^-$, $CD117^+$, $CD161^+$, $NKp46^-$ and/or $CD94/NKG2A^-$. In another embodiment, $CD56^{bright}$NK cells are $CD117^+$, $NKp46^+$, $CD94/NKG2A^+$, $CD16^-$, and/or $KIR^{+/-}$. In another embodiment, $CD56^{dim}$NK cells are $CD117^-$, $NKp46^+$, $CD94/NKG2A^{+/-}$, $CD16+$, and/or $KIR^+$. In a specific embodiment, maturation of NK cells (e.g., TSNK cells) is determined by the percentage of NK cells (e.g., TSNK cells) that are $CD161^-$, $CD94^+$ and/or $NKp46^+$. In a more specific embodiment, at least 10%, 20%, 25%, 30%, 35%, 40%, 50%, 55%, 60%, 65% or 70% of mature NK cells (e.g., TSNK cells) are $NKp46^+$. In another more specific embodiments, at least 10%, 20%, 25%, 30%, 35%, 40%, 45% or 50% of mature NK cells (e.g., TSNK cells) are $CD94^+$. In another more specific embodiments, at least 10%, 20%, 25%, 30%, 35%, 40%, 45% or 50% of mature NK cells (e.g., TSNK cells) are $CD161^-$.

In certain embodiments, the differentiation of hematopoietic cells into NK cells are assessed by detecting the expression level of, e.g., CD3, CD7 or CD127, CD10, CD14, CD15, CD16, CD33, CD34, CD56, CD94, CD117, CD161, NKp44, NKp46, NKG2D, DNAM-1, 2B4 or TO-PRO-3, using, e.g., antibodies to one or more of these cell markers. Such antibodies can be conjugated to a detectable label, for example, as fluorescent label, e.g., FITC, R-PE, PerCP, PerCP-Cy5.5, APC, APC-Cy7 or APC-H7.

6.3. Isolation of TSNK Cells

Methods of isolating natural killer cells are known in the art and can be used to isolate the TSNK cells. Natural killer cells can be isolated or enriched by staining cells from a tissue source, e.g., peripheral blood, with antibodies to CD56 and CD3, and selecting for $CD56^+CD3^-$ cells. TSNK cells can be isolated using a commercially available kit, for example, the NK Cell Isolation Kit (Miltenyi Biotec). TSNK cells can also be isolated or enriched by removal of cells other than NK cells in a population of cells that comprise the TSNK cells. For example, TSNK cells may be isolated or enriched by depletion of cells displaying non-NK cell markers using, e.g., antibodies to one or more of CD3, CD4, CD14, CD19, CD20, CD36, CD66b, CD123, HLA DR and/or CD235a (glycophorin A). Negative isolation can be carried out using a commercially available kit, e.g., the NK Cell Negative Isolation Kit (Dynal Biotech). Cells isolated by these methods may be additionally sorted, e.g., to separate $CD16^+$ and $CD16^-$ cells.

Cell separation can be accomplished by, e.g., flow cytometry, fluorescence-activated cell sorting (FACS), or, preferably, magnetic cell sorting using microbeads conjugated with specific antibodies. The cells may be isolated, e.g., using a magnetic activated cell sorting (MACS) technique, a method for separating particles based on their ability to bind magnetic beads (e.g., about 0.5-100 μm diameter) that comprise one or more specific antibodies, e.g., anti-CD56 antibodies. Magnetic cell separation can be performed and automated using, e.g, an AUTOMACST™ Separator (Miltenyi). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

6.4. Placental Perfusate

TSNK cells may be produced from hematopoietic cells, e.g., hematopoietic stem or progenitors from any source, e.g., placental tissue, placental perfusate, umbilical cord blood, placental blood, peripheral blood, spleen, liver, or the like. In certain embodiments, the hematopoietic stem cells are combined hematopoietic stem cells from placental perfusate and from cord blood from the same placenta used to generate the placental perfusate. Placental perfusate comprising placental perfusate cells that can be obtained, for example, by the methods disclosed in U.S. Pat. Nos. 7,045,148 and 7,468,276, the disclosures of which are hereby incorporated in their entireties.

6.4.1. Cell Collection Composition

The placental perfusate and perfusate cells, from which hematopoietic stem or progenitors may be isolated, or useful in tumor suppression or the treatment of an individual having tumor cells, cancer or a viral infection, e.g., in combination with the TSNK cells, as provided herein, can be collected by perfusion of a mammalian, e.g., human post-partum placenta using a placental cell collection composition. Perfusate can be collected from the placenta by perfusion of the placenta with any physiologically-acceptable solution, e.g., a saline solution, culture medium, or a more complex cell collection composition. A cell collection composition suitable for perfusing a placenta, and for the collection and preservation of perfusate cells is described in detail in related U.S. Application Publication No. 2007/0190042, which is incorporated herein by reference in its entirety.

The cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve placental cells, that is, prevent the placental cells from dying, or delay the death of the placental cells, reduce the number of placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, a hyaluronidase, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like.

The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/1 to about 100,000 units/1); or an amiloride containing compound (e.g., amiloride, ethyl isopropyl amiloride, hexamethylene amiloride, dimethyl amiloride or isobutyl amiloride present at about 1.0 μM to about 5 μM).

6.4.2. Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery.

Prior to recovery of perfusate, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415, 665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and CryoCell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of perfusate. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to collection of the perfusate, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5° C. to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental perfusate is collected.

6.4.3. Placental Perfusion

Methods of perfusing mammalian placentae and obtaining placental perfusate are disclosed, e.g., in Hariri, U.S. Pat. Nos. 7,045,148 and 7,255,879, and in U.S. Application Publication Nos. 2007/0190042 and 20070275362, the disclosures of which are hereby incorporated by reference herein in their entireties.

Perfusate can be obtained by passage of perfusion solution, e.g., saline solution, culture medium or cell collection compositions described above, through the placental vasculature. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented in such a manner that the umbilical artery and umbilical vein are located at the highest point of the placenta. The placenta can be perfused by passage of a perfusion solution through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins, that is, is passed through only the placental vasculature (fetal tissue).

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 mL of perfusion fluid is adequate to initially flush blood from the placenta, but more or less perfusion fluid may be used depending on the observed results.

The volume of perfusion liquid used to perfuse the placenta may vary depending upon the number of placental cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with a cell collection composition, or a standard perfusion solution (e.g., a normal saline solution such as phosphate buffered saline ("PBS") with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., placental cell collection composition, is repeated until the number of recovered nucleated cells falls below 100 cells/ml. The perfusates at different time points can be further processed individually to recover time-dependent populations of cells, e.g., total nucleated cells. Perfusates from different time points can also be pooled.

6.4.4. Placental Perfusate and Placental Perfusate Cells

Typically, placental perfusate from a single placental perfusion comprises about 100 million to about 500 million nucleated cells, including hematopoietic cells from which TSNK cells may be produced by the method disclosed herein. In certain embodiments, the placental perfusate or perfusate cells comprise $CD34^+$ cells, e.g., hematopoietic stem or progenitor cells. Such cells can, in a more specific embodiment, comprise $CD34^+CD45^-$ stem or progenitor cells, $CD34^+CD45^+$ stem or progenitor cells, or the like. In certain embodiments, the perfusate or perfusate cells are cryopreserved prior to isolation of hematopoietic cells therefrom. In certain other embodiments, the placental perfusate comprises, or the perfusate cells comprise, only fetal cells, or a combination of fetal cells and maternal cells.

6.5. TSNK Cells

In one aspect, provided herein are TSNK cells, the NK cells produced by the methods described herein (e.g., two-step method). Further provided herein is a population of cells comprising the TSNK cells produced by the methods described herein (e.g., two-step method). In a specific embodiment, said NK cells (e.g., TSNK cells) are $CD3^-CD56^+$. In a specific embodiment, said NK cells (e.g., TSNK cells) are $CD3^-CD56^+CD16^-$. In another specific embodiment, said NK cells (e.g., TSNK cells) are additionally $CD94^+CD117^+$. In another specific embodiment, said NK cells (e.g., TSNK cells) are additionally $CD161^-$. In another specific embodiment, said NK cells (e.g., TSNK cells) are additionally $NKG2D^-$. In another specific embodiment, said NK cells are additionally $NKp46^+$. In another specific embodiment, said said NK cells are additionally $CD226^+$.

In certain embodiments, greater than 50%, 60%, 70%, 80%, 90%, 92%, 94%, 96%, 98% of said TSNK cells are $CD56^+$ and $CD16^-$. In other embodiments, at least 50%, 60%, 70%, 80%, 82%, 84%, 86%, 88% or 90% of said TSNK cells are $CD3^-$ and $CD56^+$. In other embodiments, at least 50%, 52%, 54%, 56%, 58% or 60% of said TSNK cells are $NKG2D^+$. In other embodiments, fewer than 30%, 20%, 10%, 9%, 8%, 7%, 6%, 5%, 4% or 3% of said cells are $NKB1^+$. In certain other embodiments, fewer than 30%, 20%, 10%, 8%, 6%, 4% or 2% of said TSNK cells are $NKAT2^+$. In certain other embodiments, fewer than 30%, 20%, 10%, 8%, 6%, 4% or 2% of said TSNK cells are $CD56^+$ and $CD16^+$. In more specific embodiments, at least 10%, 20%, 25%, 30%, 35%, 40%, 50%, 55%, 60%, 65% or 70% of said $CD3^-$, $CD56^+$ TSNK cells are $NKp46^+$. In other more specific embodiments, at least 10%, 20%, 25%, 30%, 35%, 40%, 50%, 55%, 60%, 65%, 70%, 75%, 80% or 85% of said $CD3^-$, $CD56^+$ TSNK cells are $CD117^+$. In other more specific embodiments, at least 10%, 20%, 25%, 30%, 35%, 40%, 45% or 50% of said $CD3^-$, $CD56^+$ TSNK cells are $CD94^+$. In other more specific embodiments, at least 10%, 20%, 25%, 30%, 35%, 40%, 45% or 50% of said $CD3^-$, $CD56^+$ TSNK cells are $CD161^-$. In other more specific embodiments, at least 10%, 12%, 14%, 16%, 18% or 20% of said $CD3^-$, $CD56^+$ TSNK cells are $CD226^+$. In more specific embodiments, at least 20%, 25%, 30%, 35% or 40% of said $CD3^-$, $CD56^+$ TSNK cells are $CD7^+$. In more specific embodiments, at least 30%, 35%, 40%, 45%, 50%, 55% or 60% of said $CD3^-$, $CD56^+$ TSNK cells are $CD5^+$.

In various other embodiments, TSNK cells can be combined with, e.g., NK cells, wherein said NK cells have been isolated from a tissue source and have not been expanded; NK cells isolated from a tissue source and expanded, or NK cells produced by a different method, e.g., $CD56^+CD16^+$ natural killer cells, e.g., in ratios of, for example, about 1:10, 2:9, 3:8, 4:7: 5:6, 6:5, 7:4, 8:3, 9:2, 1:10, 1:9, 1:8, 1:7, 1:6, 1:5, 1:4, 1:3, 1:2, 1:1, 2:1, 3:1, 4:1, 5:1, 6:1, 7:1, 8:1 or about 9:1. As used in this context, "isolated" means that the cells have been removed from their normal tissue environment.

TSNK cells can have a fetal genotype or a maternal genotype. For example, because the post-partum placenta, as a source of hematopoietic cells suitable for producing TSNK cells, comprises tissue and cells from the fetus and from the mother, placental perfusate can comprise fetal cells only, or a substantial majority of fetal cells (e.g., greater than about 90%, 95%, 98% or 99%), or can comprise a mixture of fetal and maternal cells (e.g., the fetal cells comprise less than about 90%, 80%, 70%, 60%, or 50% of the total nucleated cells of the perfusate). In one embodiment, the TSNK cells are derived only from fetal placental hematopoietic cells, e.g., cells obtained from closed-circuit perfusion of the placenta wherein the perfusion produces perfusate comprising a substantial majority, or only, fetal placental hematopoietic cells. In another embodiment, the TSNK cells are derived from fetal and maternal cells, e.g., cells obtained by perfusion by the pan method (see above), wherein the perfusion produced perfusate comprising a mix of fetal and maternal placental cells. Thus, in one embodiment, provided herein is a population of placenta-derived intermediate natural killer cells, the substantial majority of which have the fetal genotype. In another embodiment, provided herein is a population of placenta-derived intermediate natural killer cells that comprise natural killer cells having the fetal genotype and natural killer cells having the maternal phenotype.

Also provided herein are populations of TSNK cells that comprise natural killer cells not produced by the methods described herein. For example, in one embodiment, provided herein is a population of TSNK cells that also comprises natural killer cells isolated from, e.g., umbilical cord blood, peripheral blood, bone marrow, or a combination of two or more of the foregoing, or NK cells expanded by a method other than the methods described herein. Such populations of TSNK cells can comprise the TSNK cells and other NK cells in, e.g., a ratio of about 1:10, 2:9, 3:8, 4:7: 5:6, 6:5, 7:4, 8:3, 9:2, 10:1, 1:9, 1:8, 1:7, 1:6, 1:5, 1:4, 1:3, 1:2, 1:1, 2:1, 3:1, 4:1, 5:1, 6:1, 7:1, 8:1, 9:1, 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or about 1:100, or the like.

In certain embodiments, the isolated natural killer cells (e.g., TSNK cells) or populations enriched for natural killer cells (e.g., TSNK cells) can be assessed by detecting one or more functionally relevant markers, for example, CD94, CD161, NKp44, DNAM-1, 2B4, NKp46, CD94, KIR, and the NKG2 family of activating receptors (e.g., NKG2D). In some embodiments, the purity of the isolated or enriched natural killer cells can be confirmed by detecting one or more of CD56, CD3 and CD16.

Optionally, the cytotoxic activity isolated or enriched natural killer cells can be assessed, e.g., in a cytotoxicity assay using tumor cells, e.g., cultured K562, LN-18, U937, WERI-RB-1, U-118MG, HT-29, HCC2218, KG-1, or U266 tumor cells, or the like as target cells.

6.6. TSNK Cells in Combination with Placental Perfusate

Further provided herein are compositions comprising TSNK cells in combination with placental perfusate, placental perfusate cells and/or adherent placental cells, e.g., for use in suppressing the proliferation of a tumor cell or plurality of tumor cells.

6.6.1. Combinations of TSNK Cells and Perfusate or Perfusate Cells

Further provided herein are compositions comprising combinations of the TSNK cells and placental perfusate and/or placental perfusate cells. In one embodiment, for example, provided herein is a volume of placental perfusate supplemented with TSNK cells. In specific embodiments, for example, each milliliter of placental perfusate is supplemented with about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more TSNK cells. In another embodiment, placental perfusate cells are supplemented with TSNK cells. In certain other embodiments, when placental perfusate cells are combined with TSNK cells, the placental perfusate cells generally comprise about, greater than about, or fewer than about, 50%, 45%, 40%, 35%, 30%, 25%, 20%, 15%, 10%, 8%, 6%, 4%, 2% or 1% of the total number of cells. In certain other embodiments, when TSNK cells are combined with a plurality of placental perfusate cells and/or combined natural killer cells, the NK cells generally comprise about, greater than about, or fewer than about, 50%, 45%, 40%, 35%, 30%, 25%, 20%, 15%, 10%, 8%, 6%, 4%, 2% or 1% of the total number of cells. In certain other embodiments, when TSNK cells are used to supplement placental perfusate, the volume of solution (e.g., saline solution, culture medium or the like) in which the cells are suspended comprises about, greater than about, or less than about, 50%, 45%, 40%, 35%, 30%, 25%, 20%, 15%, 10%, 8%, 6%, 4%, 2% or 1% of the total volume of perfusate plus cells, where the TSNK cells are suspended to about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter prior to supplementation.

In other embodiments, any of the above combinations of cells is, in turn, combined with umbilical cord blood or nucleated cells from umbilical cord blood.

Further provided herein is pooled placental perfusate that is obtained from two or more sources, e.g., two or more placentas, and combined, e.g., pooled. Such pooled perfusate can comprise approximately equal volumes of perfusate from each source, or can comprise different volumes from each source. The relative volumes from each source can be randomly selected, or can be based upon, e.g., a concentration or amount of one or more cellular factors, e.g., cytokines, growth factors, hormones, or the like; the number of placental cells in perfusate from each source; or other characteristics of the perfusate from each source. Perfusate from multiple perfusions of the same placenta can similarly be pooled.

Similarly, provided herein are placental perfusate cells, and placenta-derived intermediate natural killer cells, that are obtained from two or more sources, e.g., two or more placentas, and pooled. Such pooled cells can comprise approximately equal numbers of cells from the two or more sources, or different numbers of cells from one or more of the pooled sources. The relative numbers of cells from each source can be selected based on, e.g., the number of one or more specific cell types in the cells to be pooled, e.g., the number of CD34$^+$ cells, etc.

Further provided herein are TSNK cells, and combinations of TSNK cells with placental perfusate and/or placental perfusate cells, that have been assayed to determine the degree or amount of tumor suppression (that is, the potency) to be expected from, e.g., a given number of TSNK cells, or a given volume of perfusate. For example, an aliquot or sample number of cells is contacted with a known number of tumor cells under conditions in which the tumor cells would otherwise proliferate, and the rate of proliferation of the tumor cells in the presence of placental perfusate, perfusate cells, placental natural killer cells, or combinations thereof, over time (e.g., 1, 2, 3, 4, 5, 6, 7, 8, 9, or 10 weeks, or longer) is compared to the proliferation of an equivalent number of the tumor cells in the absence of perfusate, perfusate cells, placental natural killer cells, or combinations thereof. The potency of the cells can be expressed, e.g., as the number of cells or volume of solution required to suppress tumor cell growth, e.g., by about 10%, 15%, 20%, 25%, 30%, 35%, 40%, 45%, 50%, or the like.

In certain embodiments, TSNK cells are provided as pharmaceutical grade administrable units. Such units can be provided in discrete volumes, e.g., 15 mL, 20 mL, 25 mL, 30 nL. 35 mL, 40 mL, 45 mL, 50 mL, 55 mL, 60 mL, 65 mL, 70 mL, 75 mL, 80 mL, 85 mL, 90 mL, 95 mL, 100 mL, 150 mL, 200 mL, 250 mL, 300 mL, 350 mL, 400 mL, 450 mL, 500 mL, or the like. Such units can be provided so as to contain a specified number of cells, e.g., TSNK cells alone, or TSNK cells in combination with other NK cells or perfusate cells, e.g., $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more cells per unit. In specific embodiments, the units can comprise about, at least about, or at most about $1\times10^4$, $5\times10^4$, $1\times10^5$, $5\times10^5$, $1\times10^6$, $5\times10^6$ or more TSNK cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more cells per unit. Such units can be provided to contain specified numbers of TSNK cells, and/or any of the other cells.

In the above embodiments, the TSNK cells or combinations of TSNK cells with other NK cells, perfusate cells or perfusate can be autologous to a recipient (that is, obtained from the recipient), or allogeneic to a recipient (that is, obtained from at last one other individual from said recipient).

In certain embodiments, each unit of cells is labeled to specify one or more of volume, number of cells, type of cells, whether the unit has been enriched for a particular type of cell, and/or potency of a given number of cells in the unit, or a given number of milliliters of the unit, that is, whether the cells in the unit cause a measurable suppression of proliferation of a particular type or types of tumor cell.

6.6.2. Combinations of TSNK Cells and Adherent Placental Stem Cells

In other embodiments, the TSNK cells, either alone or in combination with placental perfusate or placental perfusate cells, is supplemented with isolated adherent placental cells, e.g., placental stem cells and placental multipotent cells as described, e.g, in Hariri U.S. Pat. Nos. 7,045,148 and 7,255,879, and in U.S. Patent Application Publication No. 2007/0275362, the disclosures of which are incorporated herein by reference in their entireties. "Adherent placental cells" means that the cells are adherent to a tissue culture surface, e.g., tissue culture plastic. The adherent placental cells useful in the compositions and methods disclosed herein are not trophoblasts, embryonic germ cells or embryonic stem cells. In certain embodiments, adherent placental stem cells are used as feeder cells during the processes (e.g., two-step method) as described above.

The TSNK cells, either alone or in combination with placental perfusate or placental perfusate cells can be supplemented with, e.g., $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$ or more adherent placental cells per milliliter, or $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more adherent placental cells. The adherent placental cells in the combinations can be, e.g., adherent placental cells that have been cultured for, e.g., 1, 2, 3, 4, 5, 6, 7, 8, 9, 10, 12, 14, 16, 18, 20, 22, 24, 26, 28, 30, 32, 34, 36, 38, or 40 population doublings, or more.

Isolated adherent placental cells, when cultured in primary cultures or expanded in cell culture, adhere to the tissue culture substrate, e.g., tissue culture container surface (e.g., tissue culture plastic). Adherent placental cells in culture assume a generally fibroblastoid, stellate appearance, with a number of cytoplasmic processes extending from the central cell body. Adherent placental cells are, however, morphologically distinguishable from fibroblasts cultured under the same conditions, as the adherent placental cells exhibit a greater number of such processes than do fibroblasts. Morphologically, adherent placental cells are also distinguishable from hematopoietic stem cells, which generally assume a more rounded, or cobblestone, morphology in culture.

The isolated adherent placental cells, and populations of adherent placental cells, useful in the compositions and methods provided herein, express a plurality of markers that can be used to identify and/or isolate the cells, or populations of cells that comprise the adherent placental cells. The adherent placental cells, and adherent placental cell populations useful in the compositions and methods provided herein include adherent placental cells and adherent placental cell-containing cell populations obtained directly from the placenta, or any part thereof (e.g., amnion, chorion, amnion-chorion plate, placental cotyledons, umbilical cord, and the like). The adherent placental stem cell population, in one embodiment, is a population (that is, two or more) of adherent placental stem cells in culture, e.g., a population in a container, e.g., a bag.

The adherent placental cells generally express the markers CD73, CD105, and CD200, and/or OCT-4, and do not express CD34, CD38, or CD45. Adherent placental stem cells can also express HLA-ABC (MHC-1) and HLA-DR. These markers can be used to identify adherent placental cells, and to distinguish the adherent placental cells from other cell types. Because the adherent placental cells can express CD73 and CD105, they can have mesenchymal stem cell-like characteristics. Lack of expression of CD34, CD38 and/or CD45 identifies the adherent placental stem cells as non-hematopoietic stem cells.

In certain embodiments, the isolated adherent placental cells described herein detectably suppress cancer cell proliferation or tumor growth.

In certain embodiments, the isolated adherent placental cells are isolated placental stem cells. In certain other embodiments, the isolated adherent placental cells are isolated placental multipotent cells. In a specific embodiment, the isolated adherent placental cells are CD34$^-$, CD10$^+$ and CD105$^+$ as detected by flow cytometry. In a more specific embodiment, the isolated CD34$^-$, CD10$^+$, CD105$^+$ adherent placental cells are placental stem cells. In another more specific embodiment, the isolated CD34$^-$, CD10$^+$, CD105$^+$ placental cells are multipotent adherent placental cells. In another specific embodiment, the isolated CD34$^-$, CD10$^+$, CD105$^+$ placental cells have the potential to differentiate into cells of a neural phenotype, cells of an osteogenic phenotype, or cells of a chondrogenic phenotype. In a more specific embodiment, the isolated CD34$^-$, CD10$^+$, CD105$^+$ adherent placental cells are additionally CD200$^+$. In another more specific embodiment, the isolated CD34$^-$, CD10$^+$, CD105$^+$ adherent placental cells are additionally CD90$^+$ or CD45$^-$, as detected by flow cytometry. In another more specific embodiment, the isolated CD34$^-$, CD10$^+$, CD105$^+$ adherent placental cells are additionally CD90$^+$ or CD45$^-$, as detected by flow cytometry. In a more specific embodiment, the CD34$^-$, CD10$^+$, CD105$^+$, CD200$^+$ adherent placental cells are additionally CD90$^+$ or CD45$^-$, as detected by flow cytometry. In another more specific embodiment, the CD34$^-$, CD10$^+$, CD105$^+$, CD200$^+$ adherent placental cells are additionally CD90$^+$ and CD45$^-$, as detected by flow cytometry. In another more specific embodiment, the CD34$^-$, CD10$^+$, CD105$^+$, CD200$^+$, CD90$^+$, CD45$^-$ adherent placental cells are additionally CD80$^-$ and CD86$^-$, as detected by flow cytometry.

In one embodiment, the isolated adherent placental cells are CD200$^+$, HLA-G$^+$. In a specific embodiment, said isolated adherent placental cells are also CD73$^+$ and CD105$^+$. In another specific embodiment, said isolated adherent placental cells are also CD34$^-$, CD38$^-$ or CD45$^-$. In a more specific embodiment, said isolated adherent placental cells are also CD34$^-$, CD38$^-$, CD45$^-$, CD73$^+$ and CD105$^+$. In another embodiment, said isolated adherent placental cells produce one or more embryoid-like bodies when cultured under conditions that allow the formation of embryoid-like bodies.

In another embodiment, the isolated adherent placental cells are CD73$^+$, CD105$^+$, CD200$^+$. In a specific embodiment of said populations, said isolated adherent placental cells are also HLA-G$^+$. In another specific embodiment, said isolated adherent placental cells are also CD34$^-$, CD38$^-$ or CD45$^-$. In another specific embodiment, said isolated adherent placental cells are also CD34$^-$, CD38$^-$ and CD45$^-$. In a more specific embodiment, said isolated adherent placental cells are also CD34$^-$, CD38$^-$, CD45$^-$, and HLA-G$^+$. In another specific embodiment, said isolated adherent placental cells produce one or more embryoid-like bodies when cultured under conditions that allow the formation of embryoid-like bodies.

In another embodiment, the isolated adherent placental cells are CD200$^+$, OCT-4$^+$. In a specific embodiment, said isolated adherent placental cells are also CD73$^+$ and CD105$^+$. In another specific embodiment, said isolated adherent placental cells are also HLA-G$^+$. In another specific embodiment, said isolated adherent placental cells are also CD34$^-$, CD38$^-$ and CD45$^-$. In a more specific embodiment, said isolated adherent placental cells are also CD34$^-$, CD38$^-$, CD45$^-$, CD73$^+$, CD105$^+$ and HLA-G$^+$. In another specific embodiment, the isolated adherent placental cells also produce one or more embryoid-like bodies when cultured under conditions that allow the formation of embryoid-like bodies.

In another embodiment, the isolated adherent placental cells are CD73$^+$, CD105$^+$ and HLA-G$^+$. In a specific embodiment, said isolated adherent placental cells are also CD34$^-$, CD38$^-$ or CD45$^-$. In another specific embodiment, said isolated adherent placental cells also CD34$^-$, CD38$^-$ and CD45$^-$. In another specific embodiment, said adherent stem cells are also OCT-4$^+$. In another specific embodiment, said adherent stem cells are also CD200$^+$. In a more specific embodiment, said adherent stem cells are also CD34$^-$, CD38$^-$, CD45$^-$, OCT-4$^+$ and CD200$^+$.

In another embodiment, the isolated adherent placental cells are CD73$^+$, CD105$^+$ stem cells, wherein said cells produce one or more embryoid-like bodies under conditions that allow formation of embryoid-like bodies. In a specific embodiment, said isolated adherent placental cells are also CD34$^-$, CD38$^-$ or CD45$^-$. In another specific embodiment, isolated adherent placental cells are also CD34$^-$, CD38$^-$ and CD45$^-$. In another specific embodiment, isolated adherent placental cells are also OCT-4$^+$. In a more specific embodiment, said isolated adherent placental cells are also OCT-4$^+$, CD34$^-$, CD38$^-$ and CD45$^-$.

In another embodiment, the adherent placental stem cells are OCT-4$^+$ stem cells, wherein said adherent placental stem cells produce one or more embryoid-like bodies when cultured under conditions that allow the formation of embryoid-like bodies, and wherein said stem cells have been identified as detectably suppressing cancer cell proliferation or tumor growth.

In various embodiments, at least 10%, at least 20%, at least 30%, at least 40%, at least 50% at least 60%, at least 70%, at least 80%, at least 90%, or at least 95% of said isolated adherent placental cells are OCT-4$^+$. In a specific embodiment of the above populations, said isolated adherent placental cells are also CD73$^+$ and CD105$^+$. In another specific embodiment, said isolated adherent placental cells are also CD34$^-$, CD38$^-$, or CD45$^-$. In another specific embodiment, said stem cells are CD200$^+$. In a more specific embodiment, said isolated adherent placental cells are also CD73$^+$, CD105$^+$, CD200$^+$, CD34$^-$, CD38$^-$, and CD45$^-$. In another specific embodiment, said isolated adherent placental cells have been expanded, for example, passaged at least once, at least three times, at least five times, at least 10 times, at least 15 times, or at least 20 times.

In a more specific embodiment of any of the above embodiments, the isolated adherent placental cells express ABC-p (a placenta-specific ABC transporter protein; see, e.g., Allikmets et al., *Cancer Res.* 58(23):5337-9 (1998)).

In another embodiment, the isolated adherent placental cells CD29$^+$, CD44$^+$, CD73$^+$, CD90$^+$, CD105$^+$, CD200$^+$, CD34$^-$ and CD133$^-$. In another embodiment, the isolated adherent placental cells constitutively secrete IL-6, IL-8 and monocyte chemoattractant protein (MCP-1).

Each of the above-referenced isolated adherent placental cells can comprise cells obtained and isolated directly from a mammalian placenta, or cells that have been cultured and passaged at least 1, 2, 3, 4, 5, 6, 7, 8, 9, 10, 12, 14, 16, 18, 20, 25, 30 or more times, or a combination thereof. Tumor cell suppressive pluralities of the isolated adherent placental cells described above can comprise about, at least, or no more than, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more isolated adherent placental cells.

6.6.3. Compositions Comprising Adherent Placental Cell Conditioned Media

Also provided herein is the use of a composition comprising TSNK cells and additionally conditioned medium, wherein said composition is tumor suppressive, or is effective in the treatment of cancer or viral infection. Adherent placental cells as described in Section 6.6.2, above can be used to produce conditioned medium that is tumor cell suppressive, anti-cancer or anti-viral that is, medium comprising one or more biomolecules secreted or excreted by the cells that have a detectable tumor cell suppressive effect, anti-cancer effect or antiviral effect. In various embodiments, the conditioned medium comprises medium in which the cells have proliferated (that is, have been cultured) for at least 1, 2, 3, 4, 5, 6, 7, 8, 9, 10, 11, 12, 13, 14 or more days. In other embodiments, the conditioned medium comprises medium in which such cells have grown to at least 30%, 40%, 50%, 60%, 70%, 80%, 90% confluence, or up to 100% confluence. Such conditioned medium can be used to support the culture of a separate population of cells, e.g., placental cells, or cells of another kind. In another embodiment, the conditioned medium provided herein comprises medium in which isolated adherent placental cells, e.g., isolated adherent placental stem cells or isolated adherent placental multipotent cells, and cells other than isolated adherent placental cells, e.g., non-placental stem cells or multipotent cells, have been cultured.

Such conditioned medium can be combined with any of, or any combination of TSNK cells, placental perfusate, placental perfusate cells to form a composition that is tumor cell suppressive, anticancer or antiviral. In certain embodiments, the composition comprises less than half conditioned medium by volume, e.g., about, or less than about, 50%, 45%, 40%, 35%, 30%, 25%, 20%, 15%, 10%, 5%, 4%, 3%, 2%, or 1% by volume.

Thus, in one embodiment, provided herein is a composition comprising TSNK cells and culture medium from a culture of isolated adherent placental cells, wherein said isolated adherent placental cells (a) adhere to a substrate; and (b) are CD34$^-$, CD10$^+$ and CD105$^+$; wherein said composition detectably suppresses the growth or proliferation of tumor cells, or is anti-cancer or antiviral. In a specific embodiment, the isolated adherent placental cells are CD34$^-$, CD10$^+$ and CD105$^+$ as detected by flow cytometry. In a more specific embodiment, the isolated CD34$^-$, CD10$^+$, CD105$^+$ adherent placental cells are placental stem cells. In another more specific embodiment, the isolated CD34$^-$, CD10$^+$, CD105$^+$ placental cells are multipotent adherent placental cells. In another specific embodiment, the isolated CD34$^-$, CD10$^+$, CD105$^+$ placental cells have the potential to differentiate into cells of a neural phenotype, cells of an osteogenic phenotype, or cells of a chondrogenic phenotype. In a more specific embodiment, the isolated CD34$^-$, CD10$^+$, CD105$^+$ adherent placental cells are additionally CD200$^+$. In another more specific embodiment, the isolated CD34$^-$, CD10$^+$, CD105$^+$ adherent placental cells are additionally CD90$^+$ or CD45$^-$, as detected by flow cytometry. In another more specific embodiment, the isolated CD34$^-$, CD10$^+$, CD105$^+$ adherent placental cells are additionally CD90$^+$ or CD45$^-$, as detected by flow cytometry. In a more specific embodiment, the CD34$^-$, CD10$^+$, CD105$^+$, CD200$^+$ adherent placental cells are additionally CD90$^+$ or CD45$^-$, as detected by flow cytometry. In another more specific embodiment, the CD34$^-$, CD10$^+$, CD105$^+$, CD200$^+$ adherent placental cells are additionally CD90$^+$ and CD45$^-$, as detected by flow cytometry. In another more specific embodiment, the CD34$^-$, CD10$^+$, CD105$^+$, CD200$^+$, CD90$^+$, CD45$^-$ adherent placental cells are additionally CD80$^-$ and CD86$^-$, as detected by flow cytometry.

In another embodiment, provided herein is a composition comprising TSNK cells and culture medium from a culture of isolated adherent placental cells, wherein said isolated adherent placental cells (a) adhere to a substrate; and (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the placental stem cells when said population is cultured under conditions that allow formation of embryoid-like bodies, or express OCT-4 and facilitate the formation of one or more embryoid-like bodies in a population of placental cells that comprise the placental stem cells when said population is cultured under conditions that allow formation of embryoid-like bodies; wherein said composition detectably suppresses the growth or proliferation of tumor cells, or is anti-cancer or antiviral. In a specific embodiment, the composition further comprises a plurality of said isolated placental adherent cells. In another specific embodiment, the composition comprises a plurality of non-placental cells. In a more specific embodiment, said non-placental cells comprise $CD34^+$ cells, e.g., hematopoietic progenitor cells, such as peripheral blood hematopoietic progenitor cells, cord blood hematopoietic progenitor cells, or placental blood hematopoietic progenitor cells. The non-placental cells can also comprise stem cells, such as mesenchymal stem cells, e.g., bone marrow-derived mesenchymal stem cells. The non-placental cells can also be one or more types of adult cells or cell lines. In another specific embodiment, the composition comprises an anti-proliferative agent, e.g., an anti-MIP-1α or anti-MIP-1β antibody.

In a specific embodiment, culture medium conditioned by one of the cells or cell combinations described above is obtained from a plurality of isolated adherent placental cells co-cultured with a plurality of tumor cells at a ratio of about 1:1, about 2:1, about 3:1, about 4:1, or about 5:1 isolated adherent placental cells to tumor cells. For example, the conditioned culture medium or supernatant can be obtained from a culture comprising about $1 \times 10^5$ isolated adherent placental cells, about $1 \times 10^6$ isolated adherent placental cells, about $1 \times 10^7$ isolated adherent placental cells, or about $1 \times 10^8$ isolated adherent placental cells, or more. In another specific embodiment, the conditioned culture medium or supernatant is obtained from a co-culture comprising about $1 \times 10^5$ to about $5 \times 10^5$ isolated adherent placental cells and about $1 \times 10^5$ tumor cells; about $1 \times 10^6$ to about $5 \times 10^6$ isolated adherent placental cells and about $1 \times 10^6$ tumor cells; about $1 \times 10^7$ to about $5 \times 10^7$ isolated adherent placental cells and about $1 \times 10^7$ tumor cells; or about $1 \times 10^8$ to about $5 \times 10^8$ isolated adherent placental cells and about $1 \times 10^8$ tumor cells.

6.7. Preservation of Cells

Cells, e.g., TSNK cells or placental perfusate cells comprising hematopoietic stem cells or progenitor cells, can be preserved, that is, placed under conditions that allow for long-term storage, or under conditions that inhibit cell death by, e.g., apoptosis or necrosis.

Placental perfusate can be produced by passage of a cell collection composition through at least a part of the placenta, e.g., through the placental vasculature. The cell collection composition comprises one or more compounds that act to preserve cells contained within the perfusate. Such a placental cell collection composition can comprise an apoptosis inhibitor, necrosis inhibitor and/or an oxygen-carrying perfluorocarbon, as described in related U.S. Application Publication No. 20070190042, the disclosure of which is hereby incorporated by reference in its entirety.

In one embodiment, perfusate or a population of placental cells are collected from a mammalian, e.g., human, postpartum placenta by contacting the perfusate or population of cells with a cell collection composition comprising an inhibitor of apoptosis and an oxygen-carrying perfluorocarbon, wherein said inhibitor of apoptosis is present in an amount and for a time sufficient to reduce or prevent apoptosis in the population of placental cells, e.g., adherent placental cells, for example, placental stem cells or placental multipotent cells, as compared to a population of cells not contacted with the inhibitor of apoptosis. For example, the placenta can be perfused with the cell collection composition, and placental cells, e.g., total nucleated placental cells, are isolated therefrom. In a specific embodiment, the inhibitor of apoptosis is a caspase inhibitor. In another specific embodiment, said inhibitor of apoptosis is a JNK inhibitor. In a more specific embodiment, said JNK inhibitor does not modulate differentiation or proliferation of adherent placental cells, e.g., adherent placental stem cells or adherent placental multipotent cells. In another embodiment, the cell collection composition comprises said inhibitor of apoptosis and said oxygen-carrying perfluorocarbon in separate phases. In another embodiment, the cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the placental cells. In another more specific embodiment, said apoptosis inhibitor and said perfluorocarbon are between about 2° C. and 10° C., or between about 2° C. and about 5° C., at the time of contacting the placental cells. In another more specific embodiment, said contacting is performed during transport of said population of cells. In another more specific embodiment, said contacting is performed during freezing and thawing of said population of cells.

In another embodiment, placental perfusate and/or placental cells can be collected and preserved by contacting the perfusate and/or cells with an inhibitor of apoptosis and an organ-preserving compound, wherein said inhibitor of apoptosis is present in an amount and for a time sufficient to reduce or prevent apoptosis of the cells, as compared to perfusate or placental cells not contacted with the inhibitor of apoptosis. In a specific embodiment, the organ-preserving compound is UW solution (described in U.S. Pat. No. 4,798,824; also known as VIASPAN™; see also Southard et al., *Transplantation* 49(2):251-257 (1990) or a solution described in Stern et al., U.S. Pat. No. 5,552,267, the disclosures of which are hereby incorporated by reference in their entireties. In another embodiment, said organ-preserving composition is hydroxyethyl starch, lactobionic acid, raffinose, or a combination thereof. In another embodiment, the placental cell collection composition additionally comprises an oxygen-carrying perfluorocarbon, either in two phases or as an emulsion.

In another embodiment of the method, placental cells are contacted with a cell collection composition comprising an apoptosis inhibitor and oxygen-carrying perfluorocarbon, organ-preserving compound, or combination thereof, during perfusion. In another embodiment, placental cells are contacted with said cell collection compound after collection by perfusion.

Typically, during placental cell collection, enrichment and isolation, it is preferable to minimize or eliminate cell stress due to hypoxia and mechanical stress. In another embodiment of the method, therefore, placental perfusate or a population of placental cells is exposed to a hypoxic condition during collection, enrichment or isolation for less than six hours during said preservation, wherein a hypoxic condition is a concentration of oxygen that is less than normal blood oxygen concentration. In a more specific embodiment, said perfusate or population of placental cells is exposed to said hypoxic condition for less than two hours during said preservation. In another more specific embodiment, said population of placental cells is exposed to said hypoxic condition for less than one hour, or less than thirty minutes, or is not exposed to a hypoxic condition, during collection, enrichment or isolation. In another specific embodiment, said population of placental cells is not exposed to shear stress during collection, enrichment or isolation.

Cells, e.g., placental perfusate cells, hematopoietic cells, e.g., $CD34^+$ hematopoietic stem cells; NK cells, e.g., TSNK cells; isolated adherent placental cells provided herein can be cryopreserved, e.g., in cryopreservation medium in small containers, e.g., ampoules or septum vials. In certain embodiments, cells provided herein are cryopreserved at a concentration of about $1 \times 10^4$-$5 \times 10^8$ cells per mL. In specific embodiments, cells provided herein are cryopreserved at a concentration of about $1 \times 10^6$-$1.5 \times 10^7$ cells per mL. In more specific embodiments, cells provided herein are cryopreserved at a concentration of about $1 \times 10^4$, $5 \times 10^4$, $1 \times 10^5$, $5 \times 10^5$, $1 \times 10^6$, $5 \times 10^6$, $1 \times 10^7$, $1.5 \times 10^7$ cells per mL.

Suitable cryopreservation medium includes, but is not limited to, normal saline, culture medium including, e.g., growth medium, or cell freezing medium, for example commercially available cell freezing medium, e.g., C2695, C2639 or C6039 (Sigma); CryoStor® CS2, CryoStor® CS5 or CryoStor®CS10 (BioLife Solutions). Cryopreservation medium preferably comprises DMSO (dimethylsulfoxide), at a concentration of, e.g., about 1, 2, 3, 4, 5, 6, 7, 8, 9 or 10% (v/v). Cryopreservation medium may comprise additional agents, for example, methylcellulose, dextran, albumin (e.g., human serum albumin), trehalose, and/or glycerol. In certain embodiments, the cryopreservation medium comprises about 1%-10% DMSO, about 25%-75% dextran and/or about 20-60% human serum albumin (HSA). In certain embodiments, the cryopreservation medium comprises about 1%-10% DMSO, about 25%-75% trehalose and/or about 20-60% human HSA. In a specific embodiment, the cryopreservation medium comprises 5% DMSO, 55% dextran and 40% HSA. In a more specific embodiment, the cryopreservation medium comprises 5% DMSO, 55% dextran (10% w/v in normal saline) and 40% HSA. In another specific embodiment, the cryopreservation medium comprises 5% DMSO, 55% trehalose and 40% HSA. In a more specific embodiment, the cryopreservation medium comprises 5% DMSO, 55% trehalose (10% w/v in normal saline) and 40% HSA. In another specific embodiment, the cryopreservation medium comprises CryoStor® CS5. In another specific embodiment, the cryopreservation medium comprises CryoStor® CS10.

Cells provided herein can be cryopreserved by any of a variety of methods, and at any stage of cell culturing, expansion or differentiation. For example, cells provided herein can be cryopreserved right after isolation from the origin tissues or organs, e.g., placental perfusate or umbilical cord blood, or during, or after either the first or second step of the methods outlined above. In certain embodiments, the hematopoietic cells, e.g., hematopoietic stem or progenitor cells are cryopreserved within about 1, 5, 10, 15, 20, 30, 45 minutes or within about 1, 2, 4, 6, 10, 12, 18, 20 or 24 hours after isolation from the origin tissues or organs. In certain embodiments, said cells are cryopreserved within 1, 2 or 3 days after isolation from the origin tissues or organs. In certain embodiments, said cells are cryopreserved after being cultured in a first medium as described in Section 6.2.1, above, for about 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, said cells are cryopreserved after being cultured in a first medium as described in Section 6.2.1, above, for about 1, 2, 3, 4, 5, 6, 7, 8, 9, 10, 11, 12, 13, 14, 15, 16, 17, 18, 19, 20, 21, 22, 23, 24, 25, 26, 27 or 28, and in a second medium for about 1, 2, 3, 4, 5, 6, 7, 8, 9, 10, 11, 12, 13, 14, 15, 16, 17, 18, 19, 20, 21, 22, 23, 24, 25, 26, 27 or 28 days as described in Section 6.2.1, above.

In one aspect, provided herein is a method of cryopreserving a population of NK cells, e.g., TSNK cells. In one embodiment, said method comprises: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; (b) expanding the cells from step (a) in a second medium comprising interleukin-2 (IL-2), to produce a population of activated NK cells, and (c) cryopreserving the NK cells from step (b) in a cryopreservation medium. In a specific embodiment, said step (c) further comprises (1) preparing a cell suspension solution; (2) adding cryopreservation medium to the cell suspension solution from step (1) to obtain cryopreserved cell suspension; (3) cooling the cryopreserved cell suspension from step (3) to obtain a cryopreserved sample; and (4) storing the cryopreserved sample below −80° C. In certain embodiments, the method includes no intermediary steps between step (a) and (b), and between step (b) and (c), and/or no additional culturing steps prior to step (a).

In another embodiment, said method of cryopreserving a population of NK cells, e.g., TSNK cells comprises: (a) expanding a population of hematopoietic stem or progenitor cells in a first medium comprising one or more of stem cell factor (SCF), IL-2, interleukin-7 (IL-7), interleukin-15 (IL-15) and heparin, and wherein said SCF, IL-2, IL-7 and IL-15 are not comprised within an undefined component of said medium, and wherein a plurality of hematopoietic stem or progenitor cells within said population of hematopoietic stem or progenitor cells differentiate into NK cells during said expanding; (b) expanding the cells from step (a) in a second medium comprising interleukin-2 (IL-2), to produce activated NK cells; and (c) cryopreserving the NK cells from step (b) in a cryopreservation medium. In a specific embodiment, said step (c) further comprises (1) preparing a cell suspension solution; (2) adding cryopreservation medium to the cell suspension solution from step (1) to obtain cryopreserved cell suspension; (3) cooling the cryopreserved cell suspension from step (3) to obtain a cryopreserved sample; and (4) storing the cryopreserved sample below −80° C. In certain embodiments, the method includes no intermediary steps between step (a) and (b), and between step (b) and (c).

Cells provided herein are preferably cooled in a controlled-rate freezer, e.g., at about 0.1, 0.3, 0.5, or 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C. In certain embodiments, the cryopreserved cells are thawed after being cryopreserved for about 1, 2, 4, 6, 10, 12, 18, 20 or 24 hours, or for about 1, 2, 3, 4, 5, 6, 7, 8, 9, 10, 11, 12, 13, 14, 15, 16, 17, 18, 19, 20, 21, 22, 23, 24, 25, 26, 27 or 28 days. In certain embodiments, the cryopreserved cells are thawed after being cryopreserved for about 1, 2, 3, 4, 5, 6, 7, 8, 9, 10, 11, 12, 13, 14, 15, 16, 17, 18, 19, 20, 21, 22, 23, 24, 25, 26, 27 or 28 months. In certain embodiments, the cryopreserved cells are thawed after being cryopreserved for about 1, 2, 3, 4, 5, 6, 7, 8, 9 or 10 years.

Suitable thawing medium includes, but is not limited to, normal saline, plasmalyte culture medium including, for example, growth medium, e.g., RPMI medium. In preferred embodiments, the thawing medium comprises one or more of medium supplements (e.g., nutrients, cytokines and/or factors). Medium supplements suitable for thawing cells provided herein include, for example without limitation, serum such as human serum AB, fetal bovine serum (FBS) or fetal calf serum (FCS), vitamins, human serum albumin (HSA), bovine serum albumin (BSA), amino acids (e.g., L-glutamine), fatty acids (e.g., oleic acid, linoleic acid or palmitic acid), insulin (e.g., recombinant human insulin), transferrin (iron saturated human transferrin), β-mercaptoethanol, stem cell factor (SCF), Fms-like-tyrosine kinase 3 ligand (Flt3-L), cytokines such as interleukin-2 (IL-2), interleukin-7 (IL-7), interleukin-15 (IL-15), thrombopoietin (Tpo) or heparin. In a specific embodiment, the thawing medium useful in the methods provided herein comprises RPMI. In another specific embodiment, said thawing medium comprises plasmalyte. In another specific embodiment, said thawing medium comprises about 0.5-20% FBS. In another specific embodiment, said thawing medium comprises about 1, 2, 5, 10, 15 or 20% FBS. In another specific embodiment, said thawing medium comprises about 0.5%-20% HSA. In another specific embodiment, said thawing medium comprises about 1, 2.5, 5, 10, 15, or 20% HSA. In a more specific embodiment, said thawing medium comoprises RPMI and about 10% FBS. In another more specific embodiment, said thawing medium comprises plasmalyte and about 5% HSA.

The cryopreservation methods provided herein can be optimized to allow for long-term storage, or under conditions that inhibit cell death by, e.g., apoptosis or necrosis. In one embodiments, the post-thaw cells comprise greater than 60%, 65%, 70%, 75%, 80%, 85%, 90%, 95% or 98% of viable cells, as determined by, e.g., automatic cell counter or trypan blue method. In another embodiment, the post-thaw cells comprise about 0.5, 1, 5, 10, 15, 20 or 25% of dead cells. In another embodiment, the post-thaw cells comprise about 0.5, 1, 5, 10, 15, 20 or 25% of early apoptotic cells. In another embodiment, about 0.5, 1, 5, 10, 15 or 20% of post-thaw cells undergo apoptosis after 1, 2, 3, 4, 5, 6, 7, 8, 9, 10, 11, 12, 13, 14, 15, 16, 17, 18, 19, 20, 21, 22, 23, 24, 25, 26, 27 or 28 days after being thawed, e.g., as determined by an apoptosis assay (e.g., TO-PRO3 or AnnV/PI Apoptosis assay kit). In certain embodiments, the post-thaw cells are re-cryopreserved after being cultured, expanded or differentiated using methods provided herein.

6.8. Uses of TSNK Cells

The TSNK cells provided herein can be used in methods of treating individuals having cancer, e.g., individuals having solid tumor cells and/or blood cancer cells, or persons having a viral infection. The TSNK cells provided herein can also be used in methods of suppressing proliferation of tumor cells.

6.8.1. Treatment of Individuals Having Cancer

In one embodiment, provided herein is a method of treating an individual having a cancer, for example, a blood cancer or a solid tumor, comprising administering to said individual a therapeutically effective amount of TSNK cells. In certain embodiments, the individual has a deficiency of natural killer cells, e.g., a deficiency of NK cells active against the individual's cancer. In a specific embodiment, the method additionally comprises administering to said individual isolated placental perfusate or isolated placental perfusate cells, e.g., a therapeutically effective amount of placental perfusate or isolated placental perfusate cells. In another specific embodiment, the method comprises additionally administering to said individual an effective amount of an immunomodulatory compound, e.g., an immunomodulatory compound described in Section 6.2.1, above, or thalidomide. As used herein, an "effective amount" is an amount that, e.g., results in a detectable improvement of, lessening of the progression of, or elimination of, one or more symptoms of a cancer from which the individual suffers.

In a specific embodiment, the cancer is a blood cancer, e.g., a leukemia or a lymphoma. In more specific embodiments, the cancer is an acute leukemia, e.g., acute T cell leukemia, acute myelogenous leukemia (AML), acute promyelocytic leukemia, acute myeloblastic leukemia, acute megakaryoblastic leukemia, precursor B acute lymphoblastic leukemia, precursor T acute lymphoblastic leukemia, Burkitt's leukemia (Burkitt's lymphoma), or acute biphenotypic leukemia; a chronic leukemia, e.g., chronic myeloid lymphoma, chronic myelogenous leukemia (CML), chronic monocytic leukemia, chronic lymphocytic leukemia (CLL)/Small lymphocytic lymphoma, or B-cell prolymphocytic leukemia; hairy cell lymphoma; T-cell prolymphocytic leukemia; or a lymphoma, e.g, histiocytic lymphoma, lymphoplasmacytic lymphoma (e.g., Waldenström macroglobulinemia), splenic marginal zone lymphoma, plasma cell neoplasm (e.g., plasma cell myeloma, plasmacytoma, a monoclonal immunoglobulin deposition disease, or a heavy chain disease), extranodal marginal zone B cell lymphoma (MALT lymphoma), nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides (Sezary syndrome), a primary cutaneous CD30-positive T cell lymphoproliferative disorder (e.g., primary cutaneous anaplastic large cell lymphoma or lymphomatoid papulosis), angioimmunoblastic T cell lymphoma, peripheral T cell lymphoma, unspecified, anaplastic large cell lymphoma, a Hodgkin's lymphoma or a nodular lymphocyte-predominant Hodgkin's lymphoma. In another specific embodiment, the cancer is multiple myeloma or myelodysplastic syndrome.

In certain other specific embodiments, the cancer is a solid tumor, e.g., a carcinoma, such as an adenocarcinoma, an adrenocortical carcinoma, a colon adenocarcinoma, a colorectal adenocarcinoma, a colorectal carcinoma, a ductal cell carcinoma, a lung carcinoma, a thyroid carcinoma, a nasopharyngeal carcinoma, a melanoma (e.g., a malignant melanoma), a non-melanoma skin carcinoma, or an unspecified carcinoma; a desmoid tumor; a desmoplastic small round cell tumor; an endocrine tumor; an Ewing sarcoma; a germ cell tumor (e.g., testicular cancer, ovarian cancer, choriocarcinoma, endodermal sinus tumor, germinoma, etc.); a hepatosblastoma; a hepatocellular carcinoma; a neuroblastoma; a non-rhabdomyosarcoma soft tissue sarcoma; an osteosarcoma; a retinoblastoma; a rhabdomyosarcoma; or a Wilms tumor. In another embodiment, the solid tumor is pancreatic cancer or breast cancer. In other embodiments, the solid tumor is an acoustic neuroma; an astrocytoma (e.g., a grade I pilocytic astrocytoma, a grade II low-grade astrocytoma; a grade III anaplastic astrocytoma; or a grade IV glioblastoma multiforme); a chordoma; a craniopharyngioma; a glioma (e.g., a brain stem glioma; an ependymoma; a mixed glioma; an optic nerve glioma; or a subependymoma); a glioblastoma; a medulloblastoma; a meningioma; a metastatic brain tumor; an oligodendroglioma; a pineoblastoma; a pituitary tumor; a primitive neuroectodermal tumor; or a schwannoma. In another rembodiment, the cancer is prostate cancer.

In certain embodiments, the individual having a cancer, for example, a blood cancer or a solid tumor, e.g., an individual having a deficiency of natural killer cells, is an individual that has received a bone marrow transplant before said administering. In certain embodiments, the bone marrow transplant was in treatment of said cancer. In certain other embodiments, the bone marrow transplant was in treatment of a condition other than said cancer. In certain embodiments, the individual received an immunosuppressant in addition to said bone marrow transplant. In certain embodiments, the individual who has had a bone marrow transplant exhibits one or more symptoms of graft-versus-host disease (GVHD) at the time of said administration. In certain other embodiments, the individual who has had a bone marrow transplant is administered said cells before a symptom of graft-versus-host disease (GVHD) has manifested.

In certain specific embodiments, the individual having a cancer, for example, a blood cancer, has received at least one dose of a TNFα inhibitor, e.g., ETANERCEPT® (Enbrel), prior to said administering. In specific embodiments, said individual received said dose of a TNFα inhibitor within 1, 2, 3, 4, 5, 6, 7, 8, 9, 10, 11 or 12 months of diagnosis of said cancer. In a specific embodiment, the individual who has received a dose of a TNFα inhibitor exhibits acute myeloid leukemia. In a more specific embodiment, the individual who has received a dose of a TNFα inhibitor and exhibits acute myeloid leukemia further exhibits deletion of the long arm of chromosome 5 in blood cells. In another embodiment, the individual having a cancer, for example, a blood cancer, exhibits a Philadelphia chromosome.

In certain other embodiments, the cancer, for example, a blood cancer or a solid tumor, in said individual is refractory to one or more anticancer drugs. In a specific embodiment, the cancer is refractory to GLEEVEC® (imatinib mesylate).

In certain embodiments, the cancer, for example, a blood cancer, in said individual responds to at least one anticancer drug; in this embodiment, placental perfusate, isolated placental perfusate cells, isolated natural killer cells, e.g., placental natural killer cells, e.g., placenta-derived intermediate natural killer cells, isolated combined natural killer cells, and/or combinations thereof, and optionally an immunomodulatory compound, are added as adjunct treatments or as a combination therapy with said anticancer drug. In certain other embodiments, the individual having a cancer, for example, a blood cancer, has been treated with at least one anticancer drug, and has relapsed, prior to said administering.

In one aspect, provided herein is a method of treating an individual having multiple myeloma, comprising administering to the individual (1) lenalidomide; (2) melphalan; and (3) expanded NK cells, wherein said NK cells are effective to treat multiple myeloma in said individual. In a specific embodiment, said NK cells are cord blood NK cells, or NK cells produced from cord blood hematopoietic cells, e.g., hematopoietic stem cells. In another embodiment, said NK cells have been produced by any of the methods described herein for producing NK cells, e.g., for producing TSNK cells. In another embodiment, said NK cells have been expanded prior to said administering. In another embodiment, said lenalidomide, melphalan, and/or NK cells are administered separately from each other. In certain specific embodiments of the method of treating an individual with multiple myeloma, said NK cells are produced by a method comprising: expanding a population of hematopoietic stem or progenitor cells in a first medium comprising one or more of stem cell factor (SCF), IL-2, interleukin-7 (IL-7), interleukin-15 (IL-15) and heparin, and wherein said SCF, IL-2, IL-7 and IL-15 are not comprised within an undefined component of said medium, and wherein a plurality of hematopoietic stem or progenitor cells within said population of hematopoietic stem or progenitor cells differentiate into NK cells during said expanding; and expanding the cells from step (a) in a second medium comprising interleukin-2 (IL-2).

In another aspect, provided herein is a method of treating an individual having chronic lymphocytic leukemia (CLL), comprising administering to the individual a therapeutically effective dose of (1) lenalidomide; (2) melphalan; (3) fludarabine; and (4) expanded NK cells, e.g., TSNK cells, wherein said NK cells are effective to treat said CLL in said individual. In a specific embodiment, said NK cells are cord blood NK cells, or NK cells produced from cord blood hematopoietic stem cells. In another embodiment, said NK cells have been produced by any of the methods described herein for producing NK cells, e.g., for producing TSNK cells. In a specific embodiment of any of the above methods, said NK cells have been expanded for at least 10 days prior to said administering. In a specific embodiment of any of the above methods, said lenalidomide, melphalan, fludarabine, and expanded NK cells are administered to said individual separately. In certain specific embodiments of the method of treating an individual with CLL, said NK cells are produced by a method comprising: expanding a population of hematopoietic stem or progenitor cells in a first medium comprising one or more of stem cell factor (SCF), IL-2, interleukin-7 (IL-7), interleukin-15 (IL-15) and heparin, and wherein said SCF, IL-2, IL-7 and IL-15 are not comprised within an undefined component of said medium, and wherein a plurality of hematopoietic stem or progenitor cells within said population of hematopoietic stem or progenitor cells differentiate into NK cells during said expanding; and expanding the cells from step (a) in a second medium comprising interleukin-2 (IL-2), to produce activated NK cells.

6.8.2. Suppression of Tumor Cell Proliferation

Further provided herein is a method of suppressing the proliferation of tumor cells, comprising contacting the tumor cells with TSNK cells. Optionally, the tumor cells and/or TSNK cells are contacted with isolated placental perfusate or isolated placental perfusate cells. In another specific embodiment, the tumor cells and/or TSNK cells are additionally contacted with an immunomodulatory compound, e.g., an immunomodulatory compound described in Section 6.2.1, above, or thalidomide, such that proliferation of the tumor cells is detectably reduced compared to tumor cells of the same type not contacted with TSNK cells. Optionally, the tumor cells and/or TSNK cells contacted with an immunomodulatory compound are contacted with isolated placental perfusate or isolated placental perfusate cells.

As used herein, "contacting," with respect to cells, in one embodiment encompasses direct physical, e.g., cell-cell, contact between placental perfusate, placental perfusate cells, natural killer cells, e.g., TSNK cells, and/or isolated combined natural killer cells and the tumor cells. In another embodiment, "contacting" encompasses presence in the same physical space, e.g., placental perfusate, placental perfusate cells, natural killer cells, e.g., placental intermediate natural killer cells, and/or isolated combined natural killer cells are placed in the same container e.g., culture dish, multiwell plate) as tumor cells. In another embodiment, "contacting" placental perfusate, placental perfusate cells, combined natural killer cells or placental intermediate natural killer cells, and tumor cells is accomplished, e.g., by injecting or infusing the placental perfusate or cells, e.g., placental perfusate cells, combined natural killer cells or natural killer cells, e.g., placental intermediate natural killer cells into an individual, e.g., a human comprising tumor cells, e.g., a cancer patient. "Contacting," in the context of immunomodulatory compounds and/or thalidomide, means, e.g., that the cells and the immunomodulatory compound and/or thalidomide are directly physically contacted with each other, or are placed within the same physical volume (e.g., a cell culture container or an individual).

In a specific embodiment, the tumor cells are blood cancer cells, e.g., leukemia cells or lymphoma cells. In more specific embodiments, the cancer is an acute leukemia, e.g., acute T cell leukemia cells, acute myelogenous leukemia (AML) cells, acute promyelocytic leukemia cells, acute myeloblastic leukemia cells, acute megakaryoblastic leukemia cells, precursor B acute lymphoblastic leukemia cells, precursor T acute lymphoblastic leukemia cells, Burkitt's leukemia (Burkitt's lymphoma) cells, or acute biphenotypic leukemia cells; chronic leukemia cells, e.g., chronic myeloid lymphoma cells, chronic myelogenous leukemia (CML) cells, chronic monocytic leukemia cells, chronic lymphocytic leukemia (CLL)/Small lymphocytic lymphoma cells, or B-cell prolymphocytic leukemia cells; hairy cell lymphoma cells; T-cell prolymphocytic leukemia cells; or lymphoma cells, e,g, histiocytic lymphoma cells, lymphoplasmacytic lymphoma cells (e.g., Waldenström macroglobulinemia cells), splenic marginal zone lymphoma cells, plasma cell neoplasm cells (e.g., plasma cell myeloma cells, plasmacytoma cells, monoclonal immunoglobulin deposition disease, or a heavy chain disease), extranodal marginal zone B cell lymphoma (MALT lymphoma) cells, nodal marginal zone B cell lymphoma (NMZL) cells, follicular lymphoma cells, mantle cell lymphoma cells, diffuse large B cell lymphoma cells, mediastinal (thymic) large B cell lymphoma cells, intravascular large B cell lymphoma cells, primary effusion lymphoma cells, T cell large granular lymphocytic leukemia cells, aggressive NK cell leukemia cells, adult T cell leukemia/lymphoma cells, extranodal NK/T cell lymphoma—nasal type cells, enteropathy-type T cell lymphoma cells, hepatosplenic T cell lymphoma cells, blastic NK cell lymphoma cells, mycosis fungoides (Sezary syndrome), primary cutaneous CD30-positive T cell lymphoproliferative disorder (e.g., primary cutaneous anaplastic large cell lymphoma or lymphomatoid papulosis) cells, angioimmunoblastic T cell lymphoma cells, peripheral T cell lymphoma—unspecified cells, anaplastic large cell lymphoma cells, Hodgkin lymphoma cells or nodular lymphocyte-predominant Hodgkin lymphoma cells. In another specific embodiment, the tumor cells are multiple myeloma cells or myelodysplastic syndrome cells.

In specific embodiments, the tumor cells are solid tumor cells, e.g., carcinoma cells, for example, adenocarcinoma cells, adrenocortical carcinoma cells, colon adenocarcinoma cells, colorectal adenocarcinoma cells, colorectal carcinoma cells, ductal cell carcinoma cells, lung carcinoma cells, thyroid carcinoma cells, nasopharyngeal carcinoma cells, melanoma cells (e.g., malignant melanoma cells), non-melanoma skin carcinoma cells, or unspecified carcinoma cells; desmoid tumor cells; desmoplastic small round cell tumor cells; endocrine tumor cells; Ewing sarcoma cells; germ cell tumor cells (e.g., testicular cancer cells, ovarian cancer cells, choriocarcinoma cells, endodermal sinus tumor cells, germinoma cells, etc.); hepatoblastoma cells; hepatocellular carcinoma cells; neuroblastoma cells; non-rhabdomyosarcoma soft tissue sarcoma cells; osteosarcoma cells; retinoblastoma cells; rhabdomyosarcoma cells; or Wilms tumor cells. In another embodiment, the tumor cells are pancreatic cancer cells or breast cancer cells. In other embodiments, the solid tumor cells are acoustic neuroma cells; astrocytoma cells (e.g., grade I pilocytic astrocytoma cells, grade II low-grade astrocytoma cells; grade III anaplastic astrocytoma cells; or grade IV glioblastoma multiforme cells); chordoma cells; craniopharyngioma cells; glioma cells (e.g., brain stem glioma cells; ependymoma cells; mixed glioma cells; optic nerve glioma cells; or subependymoma cells); glioblastoma cells; medulloblastoma cells; meningioma cells; metastatic brain tumor cells; oligodendroglioma cells; pineoblastoma cells; pituitary tumor cells; primitive neuroectodermal tumor cells; or schwannoma cells. In another embodiment, the tumor cells are prostate cancer cells.

As used herein, "therapeutically beneficial" and "therapeutic benefits" include, but are not limited to, e.g., reduction in the size of a tumor; lessening or cessation of expansion of a tumor; reduction in the number of cancer cells in a tissue sample, e.g., a blood sample, per unit volume; the clinical improvement in any symptom of the particular cancer or tumor said individual has, the lessening or cessation of worsening of any symptom of the particular cancer the individual has, etc.

6.8.3. Treatment of Cancers Using TSNK Cells and Other Anticancer Agents

Treatment of an individual having cancer using the TSNK cells described herein can be part of an anticancer therapy regimen that includes one or more other anticancer agents. Such anticancer agents are well-known in the art. Specific anticancer agents that may be administered to an individual having cancer, e.g., an individual having tumor cells, in addition to the TSNK cells, and optionally perfusate, perfusate cells, natural killer cells other than TSNK cells, include, but are not limited to: acivicin; aclarubicin; acodazole hydrochloride; acronine; adozelesin; adrucil; aldesleukin; altretamine; ambomycin; ametantrone acetate; amsacrine; anastrozole; anthramycin; asparaginase; asperlin; avastin (bevacizumab); azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptosar (also called Campto; irinotecan) camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux (cetuximab), human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin (e.g., Floxatin); oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine;

stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; Vectibix (panitumumab) velaresol; veramine; verdins; verteporfin; vinorelbine; vinxaltine; vitaxin; vorozole; Welcovorin (leucovorin); Xeloda (capecitabine); zanoterone; zeniplatin; zilascorb; and zinostatin stimalamer.

6.8.4. Treatment of Viral Infection

In another embodiment, provided herein is a method of treating an individual having a viral infection, comprising administering to said individual a therapeutically effective amount of TSNK cells. In certain embodiments, the individual has a deficiency of natural killer cells, e.g., a deficiency of NK cells active against the individual's viral infection. In certain specific embodiments, said administering additionally comprises administering to the individual one or more of isolated placental perfusate, isolated placental perfusate cells, isolated natural killer cells, e.g., placental natural killer cells, e.g., placenta-derived intermediate natural killer cells, isolated combined natural killer cells, and/or combinations thereof. In certain specific embodiments, the TSNK cells are contacted with an immunomodulatory compound, e.g., an immunomodulatory compound described in 6.2.1, above, or thalidomide, prior to said administration. In certain other specific embodiments, said administering comprises administering an immunomodulatory compound, e.g., an immunomodulatory compound described in Section 6.2.1, above, or thalidomide, to said individual in addition to said TSNK cells, wherein said amount is an amount that, e.g., results in a detectable improvement of, lessening of the progression of, or elimination of, one or more symptoms of said viral infection. In specific embodiments, the viral infection is an infection by a virus of the Adenoviridae, Picornaviridae, Herpesviridae, Hepadnaviridae, Flaviviridae, Retroviridae, Orthomyxoviridae, Paramyxoviridae, Papilommaviridae, Rhabdoviridae, or Togaviridae family. In more specific embodiments, said virus is human immunodeficiency virus (HIV).coxsackievirus, hepatitis A virus (HAV), poliovirus, Epstein-Barr virus (EBV), herpes simplex type 1 (HSV1), herpes simplex type 2 (HSV2), human cytomegalovirus (CMV), human herpesvirus type 8 (HHV8), herpes zoster virus (varicella zoster virus (VZV) or shingles virus), hepatitis B virus (HBV), hepatitis C virus (HCV), hepatitis D virus (HDV), hepatitis E virus (HEV), influenza virus (e.g., influenza A virus, influenza B virus, influenza C virus, or thogotovirus), measles virus, mumps virus, parainfluenza virus, papillomavirus, rabies virus, or rubella virus.

In other more specific embodiments, said virus is adenovirus species A, serotype 12, 18, or 31; adenovirus species B, serotype 3, 7, 11, 14, 16, 34, 35, or 50; adenovirus species C, serotype 1, 2, 5, or 6; species D, serotype 8, 9, 10, 13, 15, 17, 19, 20, 22, 23, 24, 25, 26, 27, 28, 29, 30, 32, 33, 36, 37, 38, 39, 42, 43, 44, 45, 46, 47, 48, 49, or 51; species E, serotype 4; or species F, serotype 40 or 41.

In certain other more specific embodiments, the virus is Apoi virus (APOIV), Aroa virus (AROAV), bagaza virus (BAGV), Banzi virus (BANV), Bouboui virus (BOUV), Cacipacore virus (CPCV), Carey Island virus (CIV), Cowbone Ridge virus (CRV), Dengue virus (DENV), Edge Hill virus (EHV), Gadgets Gully virus (GGYV), Ilheus virus (ILHV), Israel turkey meningoencephalomyelitis virus (ITV), Japanese encephalitis virus (JEV), Jugra virus (JUGV), Jutiapa virus (JUTV), kadam virus (KADV), Kedougou virus (KEDV), Kokobera virus (KOKV), Koutango virus (KOUV), Kyasanur Forest disease virus (KFDV), Langat virus (LGTV), Meaban virus (MEAV), Modoc virus (MODV), Montana myotis leukoencephalitis virus (MMLV), Murray Valley encephalitis virus (MVEV), Ntaya virus (NTAV), Omsk hemorrhagic fever virus (OHFV), Powassan virus (POWV), Rio Bravo virus (RBV), Royal Farm virus (RFV), Saboya virus (SABV), St. Louis encephalitis virus (SLEV), Sal Vieja virus (SVV), San Perlita virus (SPV), Saumarez Reef virus (SREV), Sepik virus (SEPV), Tembusu virus (TMUV), tick-borne encephalitis virus (TBEV), Tyuleniy virus (TYUV), Uganda S virus (UGSV), Usutu virus (USUV), Wesselsbron virus (WESSV), West Nile virus (WNV), Yaounde virus (YAOV), Yellow fever virus (YFV), Yokose virus (YOKV), or Zika virus (ZIKV).

In other embodiments, the TSNK cells, and optionally placental perfusate and/or perfusate cells, are administered to an individual having a viral infection as part of an antiviral therapy regimen that includes one or more other antiviral agents. Specific antiviral agents that may be administered to an individual having a viral infection include, but are not limited to: imiquimod, podofilox, podophyllin, interferon alpha (IFNα), reticolos, nonoxynol-9, acyclovir, famciclovir, valaciclovir, ganciclovir, cidofovir; amantadine, rimantadine; ribavirin; zanamavir and oseltaumavir; protease inhibitors such as indinavir, nelfinavir, ritonavir, or saquinavir; nucleoside reverse transcriptase inhibitors such as didanosine, lamivudine, stavudine, zalcitabine, or zidovudine; and non-nucleoside reverse transcriptase inhibitors such as nevirapine, or efavirenz.

6.8.5. Administration

Determination of the number of cells, e.g., placental perfusate cells, e.g., nucleated cells from placental perfusate, combined natural killer cells, and/or isolated natural killer cells, e.g., TSNK cells, and determination of the amount of an immunomodulatory compound, e.g., an immunomodulatory compound in Section 6.2.1, above, or thalidomide, can be performed independently of each other.

6.8.5.1. Administration of Cells

In certain embodiments, TSNK cells are used, e.g., administered to an individual, in any amount or number that results in a detectable therapeutic benefit to the individual, e.g., an effective amount, wherein the individual has a viral infection, cancer, or tumor cells, for example, an individual having tumor cells, a solid tumor or a blood cancer, e.g., a cancer patient. Such cells can be administered to such an individual by absolute numbers of cells, e.g., said individual can be administered at about, at least about, or at most about, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, or $1 \times 10^{11}$ TSNK cells. In other embodiments, TSNK cells can be administered to such an individual by relative numbers of cells, e.g., said individual can be administered at about, at least about, or at most about, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, or $1 \times 10^{11}$ TSNK cells per kilogram of the individual. TSNK cells can be administered to such an individual according to an approximate ratio between a number of TSNK cells, and optionally placental perfusate cells and/or natural killer cells other than TSNK cells, and a number of tumor cells in said individual (e.g., an estimated number). For example, TSNK cells can be administered to said individual in a ratio of about, at least about or at most about 1:1, 1:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1 to the number of tumor cells in the individual. The number of tumor cells in such an individual can be estimated, e.g., by counting the number of tumor cells in a sample of tissue from the individual, e.g., blood sample, biopsy, or the like. In specific embodiments, e.g., for solid tumors, said counting is performed in combination with imaging of the tumor or tumors to obtain an approximate tumor volume. In a specific embodiment, an immunomodulatory compound or thalidomide, e.g., an effective amount of an immunomodulatory compound or thalidomide, are administered to the individual in addition to the TSNK cells, optionally placental perfusate cells and/or natural killer cells other than TSNK cells.

In certain embodiments, the method of suppressing the proliferation of tumor cells, e.g., in an individual; treatment of an individual having a deficiency in the individual's natural killer cells; or treatment of an individual having a viral infection; or treatment of an individual having cancer, e.g., an individual having tumor cells, a blood cancer or a solid tumor, comprises contacting the tumor cells, or administering to said individual, a combination of TSNK cells and one or more of placental perfusate and/or placental perfusate cells. In specific embodiments, the method additionally comprises contacting the tumor cells, or administering to the individual, an immunomodulatory compound or thalidomide.

In a specific embodiment, for example, treatment of an individual having a deficiency in the individual's natural killer cells (e.g., a deficiency in the number of NK cells or in the NK ells' reactivity to a cancer, tumor or virally-infected cells); or treatment of an individual having a cancer or a viral infection, or suppression of tumor cell proliferation, comprises contacting said tumor cells, or administering to said individual, TSNK cells supplemented with isolated placental perfusate cells or placental perfusate. In specific embodiments, about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more TSNK cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{10}$ or more TSNK cells, are supplemented with about, or at least about, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more isolated placental perfusate cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more isolated placental perfusate cells. In other more specific embodiments, about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more TSNK cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more TSNK cells are supplemented with about, or at least about, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mL of perfusate, or about 1 unit of perfusate.

In another specific embodiment, treatment of an individual having a deficiency in the individual's natural killer cells; treatment of an individual having cancer; treatment of an individual having a viral infection; or suppression of tumor cell proliferation, comprises contacting the tumor cells, or administering to the individual, TSNK cells, wherein said cells are supplemented with adherent placental cells, e.g., adherent placental stem cells or multipotent cells, e.g., CD34$^-$, CD10$^+$, CD105$^+$, CD200$^+$ tissue culture plastic-adherent placental cells. In specific embodiments, the TSNK cells are supplemented with about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more adherent placental stem cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more adherent placental cells, e.g., adherent placental stem cells or multipotent cells.

In another specific embodiment, treatment of an individual having a deficiency in the individual's natural killer cells; treatment of an individual having cancer; treatment of an individual having a viral infection; or suppression of tumor cell proliferation, is performed using an immunomodulatory compound or thalidomide in combination with TSNK cells, wherein said cells are supplemented with conditioned medium, e.g., medium conditioned by CD34$^-$, CD10$^+$, CD105$^+$, CD200$^+$ tissue culture plastic-adherent placental cells, e.g., 0.1, 0.2, 0.3, 0.4, 0.5, 0.6, 0.1, 0.8, 0.9, 1, 2, 3, 4, 5, 6, 7, 8, 9, 10 mL of stem cell-conditioned culture medium per unit of perfusate, or per $10^4$, $10^5$, $10^6$, $10^7$, $10^8$, $10^9$, $10^{10}$, or $10^{11}$ TSNK cells. In certain embodiments, the tissue culture plastic-adherent placental cells are the multipotent adherent placental cells described in U.S. Pat. No. 7,468,276 and U.S. Patent Application Publication No. 2007/0275362, the disclosures of which are incorporated herein by reference in their entireties. In another specific embodiment, the method additionally comprises contacting the tumor cells, or administering to the individual, an immunomodulatory compound or thalidomide.

In another specific embodiment, treatment of an individual having a deficiency in the individual's natural killer cells; treatment of an individual having cancer; treatment of an individual having a viral infection; or suppression of tumor cell proliferation, in which said TSNK cells are supplemented with placental perfusate cells, the perfusate cells are contacted with interleukin-2 (IL-2) for a period of time prior to said contacting. In certain embodiments, said period of time is about, at least, or at most 1, 2, 3, 4, 5, 6, 7, 8, 9, 10, 12, 14, 16, 18, 20, 22, 24, 26, 28, 30, 32, 34, 36, 38, 40, 42, 44, 46 or 48 hours prior to said contacting.

The TSNK cells, and optionally perfusate or perfusate cells, can be administered once to an individual having a viral infection, an individual having cancer, or an individual having tumor cells, during a course of anticancer therapy; or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10, 24, 36 or more weeks during therapy. In embodiments in which cells and an immunomodulatory compound or thalidomide are used, the immunomodulatory compound or thalidomide, and cells or perfusate, can be administered to the individual together, e.g., in the same formulation; separately, e.g., in separate formulations, at approximately the same time; or can be administered separately, e.g., on different dosing schedules or at different times of the day. Similarly, in embodiments in which cells and an antiviral compound or anticancer compound are used, the antiviral compound or anticancer compound, and cells or perfusate, can be administered to the individual together, e.g., in the same formulation; separately, e.g., in separate formulations, at approximately the same time; or can be administered separately, e.g., on different dosing schedules or at different times of the day. The TSNK cells, and perfusate or perfusate cells, can be administered without regard to whether TSNK cells, perfusate, or perfusate cells have been administered to the individual in the past.

7. EXAMPLES

7.1. Example 1: Recovery of Hematopoietic Stem Cells from Human Placental Perfusate and Umbilical Cord Blood Human placental perfusate (HPP) and umbilical cord blood (UCB) cells were generally purified using either Ficoll or ammonium chloride to obtain total nucleated cells (TNCs). TNCs were then used in a positive selection procedure to isolate $CD34^+$ cells using anti-CD34 beads and RoboSep according to the manufacturer's protocol (StemCell Technologies, Inc.). In this experiment, $CD34^+$ cells were isolated with greater than 90% purity. Alternatively, EasySep® Human Progenitor Cell Enrichment Kit (StemCell Technologies, Inc.) was used in a negative selection procedure to deplete the lineage committed cells by using Human Progenitor Cell Enrichment Cocktail with monoclonal antibodies to the following human cell surface antigens: CD2, CD3, CD11b, CD11c, CD14, CD16, CD19, CD24, CD56, CD66b and Glycophorin A. Using the negative selection, 90% $CD34^+$ cells were recovered from the raw materials. The cell composition of the recovered HSCs was summarized in Table 1.

TABLE 1

Cell composition of enriched Hematopoietic Stem Cells (HSCs). Standard deviation was calculated for population means for 3 donors.

|  | Mean % | STDEV |
|---|---|---|
| Lin-CD34$^+$ | 75.1 | 6.2 |
| Lin-CD34$^-$CD38$^-$ | 9.8 | 2.4 |
| Lin-CD34$^-$CD133$^+$ | 0.9 | 0.2 |
| Lin-CD34$^-$CD117$^+$ | 7.2 | 0.5 |

7.2. Example 2: Feeder Cell-Free Expansion and Differentiation of Hematopoietic Stem Cells into Natural Killer Cells $CD34^+$ cells were cultured in the following medium formulations for up to 48 days, and aliquots of cells were taken for assessment of cell count, cell viability, characterization of natural killer cell differentiation and functional evaluation.

NK1 medium: GBGM (Glycostem Based Growth Medium, Glycostem Cat# CCT-SCB500, Clear cell technology) supplemented with pen/strep (Cat#15140, Gibco), 20 ng/mL SCF (Cat#255-SC, R&D Systems), 10 ng/mL Flt-3 ligand (Cat#308-FK, R&D system), 20 ng/mL TPO (Cat#288-TP, R&D system), 20 ng/mL IL-7 (Cat#207-IL, R&D Systems), 200 IU/mL IL-2 (Cat#202-IL, R&D Systems) and 10 ng/mL IL-15 (Cat#247-IL, R&D Systems).

NK2 medium: DMEM (Cat# MT-10-013-CV, Fisher): Ham's F12 (Cat# BW12-615F, Fisher) as 1:2 supplemented with 2 mM L-Glutamine (Cat#25030, Invitrogen), 1% pen/strep, 20% human serum AB (Cat#100-512, Gemcell), 5 ng/mL sodium selenite (Cat#59133, Sigma), 50 µM ethanolamine (Cat# E0135, Sigma), 25 µM β-mercaptoethanol (Cat#21985, Invitrogen), 20 mg/mL ascorbic acid (Cat#47863, Sigma), 5 ng/mL IL-3 (Cat#203-IL, R&D Systems), 20 ng/mL SCF, 10 ng/mL Flt-3 ligand, 20 ng/mL IL-7 and 10 ng/mL IL-15.

NK3 medium: X-vivo 20 (Cat# BW04-448Q, Fisher) supplemented with pen/strep, 10% human serum AB (Cat#100-512, Gemcell) and 500 IU/mL IL-2.

NK2A medium: GBGM supplemented with 10% human serum AB, 1% pen/strep, 20 ng/mL SCF, 10 ng/mL Flt-3 ligand, 20 ng/mL TPO, 20 ng/mL IL-7, 200 IU/mL IL-2, 10 ng/mL IL-15 and 1.5 IU/mL heparin (Cat# H3149, Sigma).

NK2B1 medium: DMEM:Ham's F12 as 1:2 supplemented with 2 mM L-glutamine, 1% pen/strep, 20% human serum AB, 5 ng/mL sodium selenite, 50 µM ethanolamine, 25 µM β-mercaptoethanol, 20 µg/mL ascorbic acid, 5 ng/mL IL-3, 20 ng/mL SCF, 10 ng/mL Flt-3 ligand, 20 ng/mL IL-7 and 10 ng/mL IL-15.

NK2B2 medium: DMEM:Ham's F12 as 1:2 supplemented with 2 mM L-glutamine, 1% pen/strep, 20% human serum AB, 5 ng/mL sodium selenite, 50 µM ethanolamine, 25 µM β-mercaptoethanol, 20 µg/mL ascorbic acid, 200 IU/mL IL-2, 20 ng/mL SCF, 10 ng/mL Flt-3 ligand, 20 ng/mL IL-7 and 10 ng/mL IL-15.

NK2C medium: RPMI 1640 (Cat#22400105, Invitrogen) supplemented with 10% FBS (Cat# SH30070.03, Hyclone), 2 mM L-glutamine, 1% pen/strep, 50 ng/mL SCF, 50 ng/mL Flt-3 ligand, 100 IU/mL IL-2, 20 ng/mL IL-7 and 20 ng/mL IL-15.

NK2D medium: serum-free medium (StemSpan, Cat#09650, Stem Cell Technologies, Vancouver, Canada) supplemented with 1 µM synthetic glucocorticoid dexamethosone (Dex, Cat# D4902, Sigma, St Louis, Mo.), 40 ng/mL insulin-like growth factor 1 (IGF-1, Cat#291-G1-250, R&D Systems, Minneapolis, Minn.), 100 ng/mL SCF, 40 µg/mL lipids (cholesterol-rich lipid mix; Cat# C7305-1G, Sigma, St Louis, Mo.), 5 ng/mL IL-3, 200 IU/mL IL-2, 20 ng/mL IL-7 and 20 ng/mL IL-15.

Cells collected at different time points were washed two times with RPMI1640 (phenol free) and 5% FBS, labeled with fluorescence-conjugated antibodies (Tables 2 and 3) for 15 min at 4° C., and analyzed by flow cytometry (FACSCanto, BD) and FlowJo cytometry software (Tree Star).

TABLE 2

Antibodies used for cell labeling

| HSC-NK FACS antibody Item | Vendor | Cat No. |
|---|---|---|
| FITC anti-hu CD3 | BD | 555332 |
| APC-Cy7 anti-hu CD3 | BD | 557832 |
| APC abti-hu CD5 | BD | 555355 |
| PE anti-hu CD7 | BD | 555361 |
| FITC anti-hu CD16 | BD | 555406 |
| PE-Cy5 anti-hu CD16 | BD | 555408 |
| PE anti-hu CD56 | BD | 555516 |
| PE-CY5 CD56 (N-CAM) | BD | 555517 |
| PE CD94 | R&D | FAB-1058P |
| APC anti-hu CD117 | BD | 550412 |
| PE anti-hu CD226 | BD | 559789 |
| Isotype FITC mouse IgG1 | BD | 340755 |
| Isotype PE mouse IgG1 | BD | 340761 |
| Isotype PerCP mouse IgG1 | BD | 340762 |
| Isotype PE-CY7 mouse IgG1 | BD | 348798 |
| Isotype APC mouse IgG1 | BD | 340754 |
| Isotype APC-CY7 mouse IgG1 | BD | 348802 |
| Isotype APC mouse IgG2a | BD | 555576 |
| PE anti-hu KIR-NKAT2 (2DL3) | BD | 556071 |
| PE NKB1(3DL1) | BD | 555967 |
| APC NKG2D | BD | 558071 |
| APC NKp46 | BD | 558051 |
| Simply Cellular Compensation beads | Bangs Labs | 550 |

TABLE 3

Panel of flow cytometric characterization of NK surface receptors

|  | FITC | PE | PerCP | APC | APC-Cy7 |
|---|---|---|---|---|---|
| Blank |  |  |  |  |  |
| Isotype |  |  |  |  |  |
| Panel 1 | CD3 | CD56 |  | CD16 |  |
| Panel 2 | CD16 | NKB1 | CD56 | NKG2D | CD3 |
| Panel 3 | CD16 | NKAT2 | CD56 | NKp46 | CD3 |
| Panel 4 | CD16 | CD94 | CD56 | CD117 | CD3 |

TABLE 3-continued

Panel of flow cytometric characterization of NK surface receptors

|  | FITC | PE | PerCP | APC | APC-Cy7 |
|---|---|---|---|---|---|
| Panel 5 | CD16 | CD226 | CD56 |  | CD3 |
| Panel 6 | CD16 | CD7 | CD56 | CD5 | CD3 |

Cytotoxicity assay using PKH26/TO-PRO-3 labeling. The target tumor cells were labeled with PKH26 (Cat#PKH26GL, Sigma-Aldrich), a dye that inserts into cell plasma membrane via its lipophilic aliphatic residue, then placed in 96-well U-bottom tissue culture plates and incubated with expanded NK cells at various effector-target (E:T) ratios in 200 µl RPMI 1640 supplemented with 10% FBS. Cultures were incubated for 4 hours at 37° C. in 5% $CO_2$. After incubation, cells were harvested and TO-PRO-3 (Invitrogen Cat# T3605), a membrane-impermeable DNA stain, was added to cultures (1 µM final concentration) followed by FACS analysis. Cytotoxicity was expressed as the percentage of dead cells (PKH26+TO-PRO-3+) within the total PKH26+ target tumor cells.

Optimization of $CD34^+$ cell expansion and differentiation into NK cells. Among the medium formulations tested, NK1, NK2 and NK3, NK1 medium showed a 500-fold expansion on Day 21 (D21). Neither NK2 nor NK3 medium maintained either cell proliferation or differentiation. Further medium optimization was performed for NK1 medium and the subsequent media were named NK2A, NK2B, NK2C and NK2D. $CD34^+$ cells cultured with NK2A medium showed a $10^5$-fold expansion on Day 55 (D55). Based on the results from fold expansion, differentiation, and cytotoxicity from NK1, 2 and 3 medium, the second batch of NK2A, NK2B, NK2C and NK2D medium formulations were performed and on D55, a $10^5$-fold expansion was achieved (as shown in FIG. 1). NK2B medium showed an approximately $3 \times 10^4$-fold expansion. Culture in NK2C medium resulted in $3 \times 10^2$-fold expansion in 21 days, followed by declined cell viability. NK2D medium did not maintain cells through the duration of the experiment.

On Day 48 (D48), around 90% of the NK cells in NK2A medium were $CD56^+CD3^-$. Within the $CD56^+CD3^-$ population, over 98% of cells were $CD56^+CD16^-$ (as shown in FIG. 2), while 58% expressed the activating receptor NKG2D, 68% were $NKp46^+$ and 17% were $CD226^+$ (as shown in Tables 4A and 4B).

Additionally, 97.8% of cells cultured in NK2A medium and 93.1% of cells cultured in NK2B medium were $CD56^+CD16^-$ at day 21 of cultivation.

7.3. Example 3: Culture of NK Cells in CNK Medium Enhances Expansion and Cytotoxicity of NK Cells On Day 27 (D27), $CD34^+$ cells cultured in NK2A medium were further cultured in one of the following media:

Two-stage Medium, which comprises CNK Medium and Maintenance Medium. CNK Medium is IMDM (Invitrogen) supplemented with 10% FCS (Hyclone), 200 IU/mL IL-2 (R&D Systems), 35 µg/mL transferrin (Sigma-Aldrich), 5 µg/mL insulin (Sigma-Aldrich), $2 \times 10^{-5}$ M ethanolamine (Sigma-Aldrich), 1 µg/mL oleic acid (Sigma-Aldrich), 1 µg/mL linoleic acid (Sigma-Aldrich), 0.2 µg/mL palmitic acid (Sigma-Aldrich), 2.5 µg/mL BSA (Sigma-Aldrich) and 0.1 µg/mL phytohemagglutinin (PHA-P, Sigma-Aldrich). $CD56^+CD3^-$ NK cells cultured in NK2A medium were resuspended at $2.5 \times 10^5$ live cells/mL in CNK Medium in cell culture treated 24-well plates or T flasks. Mitomycin C-treated allogeneic PBMC and K562 cells (chronic myelogenous leukemia cell line) were both added to the CNK Medium as feeder cells, to a final concentration of $1 \times 10^6$ per mL. NK cells were cultured for 5-6 days at 37° C. in 5% $CO_2$. After 5-6 days and then every 3-4 days an equal volume of Maintenance Medium (IMDM with 10% FCS, 2% Human AB serum, antibiotics, L-glutamine and 400 units of IL-2 per mL) was added to the culture.

NK2A (PDAC) medium with mitomycin C treated $CD34^-$, $CD10^+$, $CD105^+$, $CD200^+$ tissue culture plastic-adherent placental stem cells as feeder cells;

NK2A (MSC) medium with mitomycin C treated mesenchymal stem cell (MSC) as feeder cells; or Feeder-free NK2A (FF) medium as the control.

Two-stage medium enhanced the fold-expansion of the $CD34^+$ cells compared to NK2A (FF), NK2A (PDAC) and NK2A (MSC), particularly between Day 27 (D27) and Day 48 (D48). See FIG. 3.

By Day 35, the proportion of $CD34^+$ cells had already decreased to approximately 4% while the proportion of $CD56^+CD3^-$ had increased to approximately 80% in the Two-stage medium. On Day 45 (D45), cells cultured in Two-stage medium showed highest cytotoxicity as compared to NK cells cultured in NK2A (FF), NK2A (PDAC) and NK2A (MSC) (as shown in FIG. 3). Phenotypic characterization at Day 41

TABLE 4A, 4B

Phenotypic characterization of expanded NK cells on D48

4A: D48 Phenotype

| NK2A | | CD56+ CD3− | CD56+ CD16− | CD56+ CD16+ | NKB1 | NKG2D | NKAT2 |
|---|---|---|---|---|---|---|---|
| | Ave. | 86.84% | 98.44% | 1.56% | 3.38% | 58.41% | 1.69% |
| | STD | 4.50% | 0.30% | 0.30% | 1.42% | 5.88% | 0.22% |

4B: D48 Phenotype: CD56+CD3−

| NKp46 | CD94 | CD117 | CD226 | CD7 | CD5 |
|---|---|---|---|---|---|
| 67.92% | 38.08% | 80.53% | 17.32% | 34.43% | 53.53% |
| 5.43% | 21.14% | 14.27% | 14.26% | 8.48% | 3.00% |

(as shown in FIG. 5) showed increased expression of NKp46 and CD226 in the cells, indicating a possible explanation for the enhancement of cytotoxicity. At D41 the proportion of $CD226^+$ cells increased from 0.9%±0.8% in NK2A medium to 13%±4% in Two-stage medium; the proportion of $NKp46^+$ cells increased from 55.4%±8.7% in NK2A medium to 80%±7.85% in Two-Stage medium. At D48 the proportion of CD226+ cells increased from 17.3%±14.3% in NK2A medium to 52.3%±11.64% in Two-Stage medium; the proportion of $NKp46^+$ cells increased from 67.9%±5.4% in NK2A medium to 86%±4% in Two-Stage medium. There was no significant difference of NKG2D expression among the conditions tested. Changes in expression of CD226 and NKp46 are shown in Table 5, below.

TABLE 5

Expression of CD226 and NKp46 on NK cells cultured in NK2A (FF) and Two-Stage medium at day 41 (D41) and day 48 (D48). Standard deviation was calculated for 3 donors.

|  |  | NK2A (FF) | Two-Stage |
|---|---|---|---|
| D41 |  |  |  |
| CD226% | Average | 0.9% | 13% |
|  | STDEV | 0.8% | 4% |
| NKp46% | Average | 55.4% | 80% |
|  | STDEV | 8.7% | 7.85% |
| D48 |  |  |  |
| CD226% | Average | 17.3% | 52.3% |
|  | STDEV | 14.3% | 11.6% |
| NKp46% | Average | 67.9% | 86% |
|  | STDEV | 5.4% | 4% |

7.4. Example 4: Comparison of Two-Stage Medium-Cultivated Natural Killer Cells and Natural Killer Cells Derived from Embryonic Stem Cells (ESCs)

NK cells cultured in the Two-stage medium were compared with NK cells derived from embryonic stem cells (ESCs), which were produced by the method of Woll et al., Blood 113(4):6094-6101 (2009). Specifically, a difference in expression levels of CD94 and CD117 was observed during the process of cultivation of both of the cell types. FIG. 6 shows that the expression of CD117 was high in the Two-stage NK cells, or "+", from Day 7 (D7) to Day 35 (D35), while the expression of CD94 gradually increased. On Day 35 (D35), about 44% of the $CD56^+CD3^-$ (Two-step) cells were $CD94^+CD117^+$ cells, 37.6% of the $CD56^+CD3^-$ cells were $CD94^-CD117^+$ and 14.7% of the $CD56^+CD3^-$ cells were $CD94^+CD117^-$. As such, the NK cells produced by the Two-step method are distinguishable from the NK cells derived from ESCs, 78% of which remained $CD117^{low/-}$ from Day 14 to Day 35 of the cultivation. This difference in CD117 expression is useful because $CD117^+$ NK cells are cytotoxic towards tumor cell lines from various tissues, as described in Example 6, below.

These results suggest that the differentiation progression of TSNK cells is different from ESC-derived NK cells, and that TSNK cells are distinguishable from ESC derived NK cells.

7.5. Example 5: PDACs Enhance Fold Expansion of Cultured Natural Killer Cells in NK2A Medium To assess the effect of $CD10^+$, $CD34^-$, $CD105^+$, $CD200^+$ tissue culture plastic-adherent placental stem cells (referred to in this Example as PDACs) on hematopoietic stem cell (HSC) differentiation to natural killer cells, HSCs were stimulated with mitomycin C-treated PDACs or bone marrow-derived mesenchymal stem cells (MSC) at a ratio of 10:1 PDACs/MSC:HSC on Day 0 and Day 21, while a feeder-free culture was used as the control. NK2A medium was used as culture medium. PDACs were found to enhance the fold expansion of cultured NK cells compared to medium alone. However, no significant difference in cytotoxicity between cells grown with or without the feeder layer was found. Cells treated with MSC showed the highest fold expansion, but the lowest cytotoxicity, as shown in FIG. 7.

7.6. Example 6: Cytotoxic Activity of NK Cells Expanded Using Two-Stage Medium

This Example demonstrates that NK cells produced from $CD34^+$ cells expanded and differentiated using the Two-stage process described above are cytotoxic to tumor cell lines.

Lactate Dehydrogenase (LDH) release assay. The LDH release assay was performed using CYTOTOX 96® non-radioactive cytotoxicity assay kit (Promega, Cat# G1780). In this assay, cultured NK cells derived from donor-matched human placental perfusate (HPP) and cord blood units (Combos units) were used as effector cells, while certain tumor cell line cells were used as target cells. From three units used in this study, the percentage of HPP cells was 56.6%±28.3%. Effector cells and target cells were placed in 96-well U-bottom tissue culture plates and incubated at various effector-target (E:T) ratios in 100 µl RPMI 1640 without phenol red (Invitrogen, Cat#11835-030) supplemented with 2% human AB serum (Gemini, Cat#100-512). Cultures were incubated for 4 hours at 37° C. in 5% $CO_2$. After incubation, 50 µl supernatant was transferred to enzymatic assay plate, LDH activity was detected as provided by the manufacturer, and absorption was measured at 490 nm in an ELISA reader (Synergy HT, Biotek). The cytotoxicity was calculated according to the following equation: % Cytotoxicity=(Sample−Effector Spontaneous−Target Spontaneous)/(Target maximum−Target Spontaneous)*100, where "Effector Spontaneous" is a control for the spontaneous release of LDH from effector cells; "Target Spontaneous" is a control for the spontaneous release of LDH from target cells; and "Target Maximum" is a control for the maximum LDH release when essentially 100% of cells are lysed.

Isolation of Human Placental Perfusate (HPP) CD34+ Cells and Umbilical Cord Blood (UCB) CD34+ Cells. HPP and UCB cells were purified using either Ficoll or ammonium chloride to obtain total nucleated cells (TNCs). TNCs were then used in a positive selection procedure to isolate $CD34^+$ cells using anti-CD34 beads and RoboSep following the protocol provided by the manufacturer (StemCell Technologies, Inc.) In this experiment, $CD34^+$ cells were isolated with greater than 90% purity.

Study of tumor cell susceptibility to cultured two-stage NK cells. Tumor cell lines (Table 1), including human breast cancer (HCC2218), human colorectal adenocarcinoma (HT-29), human chronic myelogenous leukemia (CML), human acute myeloid leukemia (AML), human glioblastoma (LN-18 and U-118MG), human multiple myeloma (U266), human histiocytic lymphoma (U937), and human retinoblastoma (WERI-RB-1) were co-cultured with two-stage NK cells. The two-stage cultured NK cells included those cultured in NK2A medium for 21 days, then cultured in CNK Medium for 21 days, and those cultured in NK2A medium for 28 days and then CNK Medium for 14 days. The NK cell cytotoxicity was measured by the lactate dehydrogenase (LDH) release assay after 4-hour co-culture. At effector to target (E:T) ratio of 10:1 the latter generally showed higher cytotoxicity than the former (Table 6). Of the tumor cell lines, LN-18 was the most susceptible to NK-mediated killing, followed by K562, U937, WERI-RB-1, U-118MG, HT-29, HCC2218, KG-1 and U266.

TSNK cells therefore showed significant cytotoxicity toward various cancer cell lines. It further appears that the NK cytotoxicity can be improved by prolonging the culture period in NK2A medium from 21 days to 28 days.

TABLE 6

Cytotoxicity of cultured TSNK cells targeting on tumor cell lines

| Tumor Lines | 21-Day NK2A Medium + 21-Day CCT NK Medium | | 28-Day NK2A Medium + 14-Day CCT NK Medium | |
|---|---|---|---|---|
| | % Average Cytotoxicity | STDEV | % Average Cytotoxicity | STDEV |
| HCC2218 | 15.65 (n = 1) | | 11.89 (n = 3) | 10.2 |
| HT-29 | 20.52 (n = 3) | 9.3 | 33.42 (n = 3) | 20.2 |
| K562 | 69.63 (n = 3) | 27.6 | 80.04 (n = 3) | 25.4 |
| KG-1 | 5.67 (n = 3) | 3.4 | 15.41 (n = 3) | 9.2 |
| LN-18 | 99.00 (n = 3) | 0.0 | 99.00 (n = 3) | 0.0 |
| U-118MG | 23.12 (n = 3) | 6.9 | 49.16 (n = 2) | 15.8 |
| U266 | 2.21 (n = 1) | | 5.07 (n = 2) | 3.3 |
| U937 | 46.44 (n = 2) | 19.3 | 51.58 (n = 2) | 23.2 |
| WERI-RB-1 | 25.30 (n = 2) | 4.7 | 36.79 (n = 2) | 11.3 |

*n: number of donors

MicroRNA Profiling of Human Placental Perfusate (HPP) CD34+ Cells and Umbilical Cord Blood (UCB) CD34+ Cells. Purified donor-matched HPP and UCB CD34+ cells were subjected to microRNA (miRNA) preparation using a MIRVANA™ miRNA Isolation Kit (Ambion, Cat#1560). CD34+ cells (0.5 to 1.5×10$^6$ cells) were disrupted in a denaturing lysis buffer. The samples were then subjected to acid-phenol+chloroform extraction to isolate RNA highly enriched for small RNA species. 100% ethanol was added to bring the samples to 25% ethanol. When this lysate/ethanol mixture was passed through a glass fiber filter, large RNA species were immobilized, and the small RNA species were collected in the filtrate. The ethanol concentration of the filtrate was then increased to 55%, and the mixture was passed through a second glass fiber filter where the small RNAs became immobilized. This RNA was washed a few times, and eluted in a low ionic strength solution. The concentration and purity of the recovered small RNA was determined by measuring its absorbance at 260 and 280 nm. miRNAs found to be unique for HPP CD34+ cells in all donors tested (n=3) included hsa-miR-380, hsa-miR-512, hsa-miR-517, hsa-miR-518c, hsa-miR-519b, and hsa-miR-520a.

7.7. Example 7: Isolation of CD34+ Cells from Pooled UCB and HPP

This example demonstrates the isolation of CD34+ cells from pooled umbilical cord blood (UCB) and human placental perfusate (HPP) (Combo). To evaluate the UCB:HPP pooling ratio, side-by-side comparisons of 3 different pooling ratios were performed as as follows: (1) Full pooling: 1×UCB (full volume)+1×HPP (full volume); (2) Partial pooling of HPP (33%): 1×UCB (full volume)+0.33×HPP (⅓ of HPP volume); and (3) Partial pooling of HPP (10%): 1×UCB (full volume)+0.10×HPP (¹⁄₁₀ of HPP volume). A total of N=3 experimental replicates were executed. The initial TNC and volumes were recorded. The pooled samples were then purified for CD34+ cells and CD34+ purity was determined post-thaw. The optimal pooling ratio was then determined graphically from the post-thaw CD34+ purity vs. volumetric or cell count (TNC) fractions (as a % of Combo) plots. As shown in FIG. 8, the end-point CD34+ purity correlates well with the HPP volume content, but not as much with the HPP TNC content. Overall, UCB 85% v/v, HPP 15% v/v was found to to be the optimal pooling ratio to obtain CD34+ cells with purity of 80% and above.

7.8. Example 8: Comparison of NK Cell Cultivation Using GBGM®-based Media

This example desmonstrates the comparison of NK cell cultivation processes using two GBGM-based media (the three-stage process and two-stage process). The two processes are summaried in Table 10. Both processes utilized GBGM as the basal medium for the differentiation of NK cells and CD34+ cells of placenta in origin.

TABLE 7

Summary of the three-stage and two-stage processes

| | Three-Stage Process | Two-Stage Process |
|---|---|---|
| Cultivation Process | 3-Stage, GBGM based, feeder-free, 35 days<br>Stage 1 (9 days): GBGM with 10% human serum AB (HS), LWH heparin, TPO, SCF, IL-7, Flt3L (25-27 ng/mL)<br>Stage 2 (5 days): GBGM with 10% HS, LWH heparin, SCF, IL-7, Flt3L, IL-15 (20-27 ng/mL)<br>Stage 3 (21 days): GBGM with 10% HS, SCF, IL-7, Flt3L, IL-15 (20-27 ng/mL), IL-2 (1000 U/mL)<br>Use of low-dose cytokines (IL-6, LIF, G-CSF, GM-CSF, MIP-1a) throughout, at 50-250 pg/mL | 2-Stage, GBGM in 1$^{st}$ Stage, with K562/PBMC feeders, 35 days<br>Stage 1 (21 days): GBGM with 10% human serum, heparin, TPO, SCF, IL-7, Flt3L, IL-15, (10-20 ng/mL), IL-2 (200 U/mL).<br>Stage 2 (14 days): CCT NK Expansion Process in CCT NK Medium, IMDM with 10% FBS, K562 + PBMC feeders, IL-2 (200 U/mL).<br>Media replenishment in Stage-2 with CCT NK Maintenance Medium, IMDM with 10% FBS, 2% HS, IL-2 (200 U/mL) |

The experimental parameters are outlined as follows:
Donor Lots:
(1) CD34+ cells from fresh UCB: N=6
(2) CD34+ cells from fresh "Combo": N=2
(3) CD34+ from cryopreserved "Combo": N=8
Scale: Multiwell dishes to T-25, up to multiple T-75 flasks, 1 to 80 mL in culture volume
Process METHODS:
(1) Two-Stage process
(2) Three-Stage process
Use of Feeders:
(1) Without feeders
(2) With inactivated K562 & PBMC feeders, added to culture at Day 21
Seeding density: 20000-50000 cells/mL
CD34+ cells from either fresh UCB or fresh combo were generated and cryopreserved with methods described in Examples 7, 10 and 11. Cultures were maintained in a 37° C., >90% humidity, and 5% $CO_2$ incubator. Cell growth was monitored throughout (cell count) and medium exchanges were performed twice per week to maintain cell concentrations within the range of $5\times10^4$-$1\times10^6$ per mL. Differentiation was monitored by phenotypic analysis at Day 21 and 35. When feeders were used, at Day 21 of NK cultivation, fresh 3-day cultured K562 and post-thaw allo-PBMC were inactivated with mitomycin-C (16 μg/mL, 2 hrs, 37° C.) and were added to the two-stage process conditions at $1\times10^6$ per mL. The differentiating NKs were normalized to $0.5\times10^6$ per mL. At Day 35, after final cell counts were performed, a flow cytometry-based cytotoxicity assay using freshly cultured and PKH labeled K562 cells (10:1 E:T ratio, 4 hr, 37° C.) was performed to evaluate NK functionality.

Results

The median of the TNC expansion fold for $CD34^+$ cells derived from fresh UCB using the two processes were comparable at Day 35. The two-stage process appeared to yield higher TNC expansion fold than the three-stage process for fresh combo-derived $CD34^+$ cells. The overall TNC expansion folds were comparable for the $CD34^+$ cells derived from post-thaw combo using both processes, but were significantly lower than those derived from fresh UCB or fresh combo. In all, both the three-stage and two-stage processes yielded similar cell yield at end of cultivation.

At Day 21, there were no noticeable differences of phenotype on cells originated from UCB or Combo. The two-stage process resulted in a higher percentage of $CD56^+CD3^-$ NK cells (avg. 14.7%) than the three-stage process (avg. 6.1%). The extent of differentiation (e.g., $CD56^+CD3^-$ level) appeared to be donor-dependent. The percentage of both $CD3^+CD56^-$ (T-cells) and $CD3^+CD56^+$ (NKT-like cells) populations were minimal in all cases.

At Day 35, both processes were found to be effective for differentiating NK cells, as evidenced by the high end-point $CD56^+CD3^-$ purity levels (87.2% and 90.1% for the two-stage and three-stage processes, respectively). The addition of feeders in the two-stage process appeared to enhance NK phenotypic purity (75.3% without feeders; 87.2% with feeders), while no observable benefit of feeders on NK purity was found (90.1% without feeders; 84.7% with feeders) with the three-stage process.

Cultivated NK cells maintained their $CD16^-$ phenotype throughout. The two-stage process appeared to yield slightly more $CD56^+CD3^+$ cells in the absence of feeders (avg. 11.2%) than the other conditions (<2%). The presence of PBMC and K562 feeders in both processes significantly upregulated/activated certain NK functional markers (NKp46, DNAM-1, CD94) on the NK cell population. Overall, the NK purity and functional marker expression profiles were found to be comparable between the two processes, when the feeder conditions are identical.

The functionality of cultivated NK cells, as determined by the 4 hour in vitro K562 cytotoxicity assay, was found to be comparable between the two processes when feeder conditions are identical. Feeder-activated NK cells were highly effective in killing K562 cells in vitro, with average specifc lysis of 93.2% and 93.6% specific lysis for the two-stage and three-stage processes, respectively.

In summary, the two-stage and three-stage processes were found to yield comparable growth, phenotype (purity and activation markers), and in vitro functionality for NK cells when the same feeder condition was used. The two-stage process offers the ease and convenience of culturing NK cells compared to the three-stage process.

7.9. Example 9: Comparison of NK Cell Cultivation Using Various Basal Media

This study is aimed to evaluate the differentiation and expansion of $CD34^+$-derived NK cells using different basal media.

The experimental conditions are summarized in Table 11. The cells were cultured as described in Example 11. All experiments were setup in the scale of multiwell dishes/T-flasks and were maintained in a 37° C., >90% humidity, and 5% $CO_2$ incubator. Cell growth was monitored throughout (cell count) and medium exchanges were performed twice per week to maintain cell concentrations within the range of $5\times10^4$-$1\times10^6$ per mL. Differentiation was monitored by phenotypic analysis at Day 21 and 35. At Day 21, fresh 3-day cultured K562 and post-thaw allo-PBMC were inactivated and were added to developing NK cell culture at $1\times10^6$ per mL. The NK cells were normalized to $0.5\times10^6$ per mL. At Day 35, after final cell counts were performed, a flow cytometry-based cytotoxicity assay using freshly cultured and PKH labeled K562 cells (10:1 E:T ratio, 4 hr, 37° C.) was carried out to evaluate NK functionality.

TABLE 8

Summary of experimental conditions for evaluation of various basal media

| | |
|---|---|
| CD34+ donors | 1 UCB donor |
| Cultivation Process Method | Three-Stage Process |
| K562 & PBMC feeders | With feeders @ day21 |
| Basal media screened | GBGM (control) |
| | AIM-V |
| | X-VIVO 10 |
| | X-VIVO 15 |
| | OpTmizer |
| | Stemspan H3000 |
| | Cellgro |
| | DMEM:F12 |
| | DMEM:F12 w/5 mM OAC (added to culture from Day 7 to Day35) |
| Seeding density (day0) | 50000/mL |

Growth Yield

Stemspan H3000 and OpTmizer showed comparable growth yield (TNC expansion fold) to GBGM at Day 35. Cellgro, X-VIVO 15, AIM-V, X-VIVO 10, DMEM:F12, DMEM:F12 w/5 mM OAC showed lower growth yield than GBGM.

Phenotypic Analysis

At Day 35 (end-point), GBGM yielded about 80% purity of $CD56^+CD3^-$ cells. OpTmizer and Stemspan H3000 yielded about 50% purity of $CD56^+CD3^-$ cells. DMEM:F12 produced about 35% purity of $CD56^+CD3^-$ cells. AIM-V, X-VIVO 10, X-VIVO 15, and Cellgro media produced about <30% purity of $CD56^+CD3^-$ cells. The addition of OAC to DMEM:F12 basal medium during culture was found to greatly enhance the end-point NK purity; the percentage of $CD56^+CD3^-$ at Day 35 of culture increased from 35% to 72%.

Cytotoxicity/Functionality

The addition of 5 mM OAC to DMEM:F12 basal medium during culture was found to greatly enhance the activation status and in vitro functionality of NK cells. The addition of OAC also significantly increased the level of NK activation markers NKp46, NKG2D, DNAM-1, and CD94. The in vitro functionality (K562 cytotoxicity) of Day-35 NK cells increased substantially as well, from 21.4% to 97.1% %.

Overall, the NK cell properties were significantly enhanced from the addition of 5 mM OAC.

7.10. Example 10: Storage and Cryopreservation of NK Cells

This Example demonstrates the methods of storing and cryopreserving NK cells. CD34+ hematopoietic stem cells isolated from human placental perfusate (HPP) and umbilical cord blood cells were expanded and differentiated into NK cells using the protocols described in the previous examples. Cells were cryoprevered right after being isolated from HPP and umbilical cord blood (at Day 0) or during the first growth phase of the NK cells (at Day 9, Day 14, Day 21 or Day 35 post isolation).

The cells were cryopreserved in the following cryopreservation formulations: Formulation 1-dextran cryo medium: 5% DMSO (Sigma Aldrich, D2650), 55% dextran (10% w/v in normal saline) (10% LMD in 0.9% sodium chloride injection, Hospira), 40% HAS (Octapharma); Formulation 2—Trehalose cryo medium: 5% DMSO, 55% trehalose (10% w/v in normal saline), 40% HSA; Formulation 3—CryoStor® CS2 (BioLife Solutions); Formulation 4—CryoStor® CS5 (BioLife Solutions); Formulation 5—CryoStor® CS10 (BioLife Solutions); Formulation 6-Serum-free freezing media (Sigma-Aldrich, Cat#6295); Formulation 7—Glycerol freezing media (Sigma-Aldrich, CAT# C6039); or Formulation 8—DMSO and serum-free freezing media (Sigma-Aldrich, CAT#2639).

Cells collected at different ime points were washed several times with culture media or saline solution. The cells were then centrifuged to obtain cell pellets. The supernatants were removed, and the cells pellets were suspended with cryopreservation media to about $1\times10^6$-$1.5\times10^7$ or more cells per milliliter. The cell suspension was aliquoted to 1 mL or 2 mL septum vials and incubated at 2-8° C. for approximately 10 minutes. Subsequently, the cells were frozen in a control rate freezer (Thermo) at 0.5° C./min. Frozen vials were transferred to a cryogenic freezer for storage in liquid nitrogen vapor. Cryopreserved NK cells can be thawed quickly in a 37° C. water bath with gentle swirling of the samples until all visible ice melted. The cell samples can be diluted with pre-warmed culture media.

7.11. Example 11: Storage and Cryopreservation of NK Cells

This Example demonstrates another method of storing and cryopreserving NK cells. CD34+ hematopoietic stem cells isolated from human placental perfusate (HPP) and umbilical cord blood cells were expanded and differentiated into NK cells using the protocols described above. Cells were cryoprevered right after being isolated from HPP and umbilical cord blood (at Day 0) or during the first growth phase of the NK cells (at Day 9, Day 14, Day 21 or Day 35 post isolation).

A Cell Suspension Solution was prepared by combining Dextran-40 and HSA in the ration of 60% Dextran-40 v/v, 40% HSA (from a 25% solution) v/v).

A 2× Freezing Solution was prepared with 50% Dextran-40 v/v, 40% HSA (25% solution) v/v, 10% DMSO v/v. DMSO was first slowly added to the Dextran-40 and mixed well. Subsequently 25% solution of HSA was added to the solution slowly with mixing. The resulting solution was mixed well and brought to room temperature prior to use.

Cryopreservation Procedure

The cell number was estimated and normalized as a cell suspension to $15\times10^6$ in Cell Suspension Solution. The volume of the cell suspension was determined and an equal volume of freshly prepared 2× Freezing Solution was slowly added and mixed. The final cell suspension volume in Freezing Solution was recorded and the distributed to a number of vials. MycoAlert testing was performed on saved culture supernants to detect mycoplasma contamination. A post-thaw test was conducted on one retain vial to determine the post-thaw viability, cell recovery and cell characterization.

7.12. Example 12: Analysis of Cryopreserved/Thawed NK Cells

Viability assay. NK cells cryopreserved in various formulations as in Example 10 or 11 were thawed. Cells were frozen at the density of $2\times10^6$-$3\times10^7$ cells/mL. Thawed NK cells were evaluated for cell viability using the Countess® Automated Cell Counter (Invitrogen) at Day 0, Day 3 and Day 18 post thawing compared to fresh cells or prefreeze cells. Briefly, 10 μl of cell samples were mixed with 10 μl of trypan blue. The cell mixtures were pipeted into the Countess® chamber slide. The slide was inserted into the instrument and the cells were counted. Post-freeze-thaw cells showed cell viability about 80% to >90% of viability, depending on different cryopreservation formulations.

Apoptosis assay. Thawed NK cells were also evaluated for apoptosis using BD AnnV/PI Apoptosis assay kit at Day 0, Day 3 and Day 18 post thawing. Briefly, cells were washed twice with 1× cold PBS and re-suspended in 1× binding buffer (BD Annexin V/PI Apoptosis Kit part number 556547 Composition of Binding buffer part number 51-66121E 0.1M Hepes/NaOH (pH7.4), 1.4M NaCl, 25 mM CaCl2. For 1× dilute 1part 10× buffer to 9 parts of distilled water). 100 μL of cell suspension containing approximagely 100,000 cells was transferred into a FACS tube. 100 μL of 1× binding buffer, 5 μL of AnnV-FITC, and 5 μL of PI-PE were added to the tube. The tube was then gently vortexed and incubated in the dark for 15 minutes. Subsequently, 400 μL of 1× binding buffer was added. The samples were analyzed within 1 hour. Controls used to set up quadrants and gates were unstained cells, cells stained with AnnV-FITC only and not PI, cells stained with PI only and not AnnV The apoptotic cells were quantified as a % of the population of events gated as "cells" on the size scatter (FSC vs SSC) plot. The post-freeze-thaw cells showed about 5-25% of dead/late apoptotic cells and 10-25% of early apoptotic cells, depending on different cryopreservation formulations. Overall, formulation 1 (5% DMSO, 55% dextran (10% w/v in normal saline), 40% HAS), formulation 2 (5% DMSO, 55% trehalose (10% w/v in normal saline), 40% HSA), formulation 4—CryoStor® CS5 (BioLife Solutions), and formulation 5 (CryoStor® CS10 (BioLife Solutions)) showed higher cell viability and lower apoptotic cells compared to other formulations.

7.13. Example 13: Evaluation of In-Process Cryopreserved Cell Banking

This example demonstrates the evaluation of 1n-Process Cryopreserved Cell Banking. The cell culture was initiated with UCB CD34+ cells using the method as described by Spanholtz et al, PLoS One. 5(2):e9221(2010) using either HS-AB or FBS as the serum source. The cell concentration was determined and adjusted, and the medium was replenished as needed. At Day 7, 9, 10 or 14, approximately $10^6$-$3\times10^6$ cells were removed from the cell culture, centrifuged and resuspended in cryopreservation medium (5.5% v/v Dextran-40, 10% v/v HSA, 5% v/v DMSO). The cells were frozen in a controlled-rate freezer and transferred to liquid phase nitrogen storage for cryopreservation. Approximately 1 mL cells each vial were cryopreserved at a concentration ranging from $10^6$-$10^7$ per mL. The remaining culture was carried forward to the end-point (Day 35), referred to as "Fresh (no in-process cryopreservation)". Phenotypic analyses were performed on Day 21, 28, and 35 of the cell culture. In vitro functionality (K562 cytotoxicity, 10:1 E:T) was assessed at Day 35 (end-point) of the culture.

Post-thaw performance of the in-process cryopreserved culture samples (Day 9 and 14) were evaluated as follows. The cell bank vials were quickly thawed in the 37° C. water bath. The cells were then diluted with RPMI-FBS medium, centrifugated, resuspended, and seeded in culture media. Each of the culture conditions were then carried forward to Day 35, cumulative from the start of culture process. Analytics (cell count, viability, phenotypic analysis, functionality assessment) were done in the same manner as their "Fresh" counterpart.

Results

Day 9, 10, and 14 in-process cryopreserved samples all yielded excellent post-thaw viability, regardless of in-process time point or cell concentration (96.2%-97.3% Trypan Blue negative, 86.1%-93.2% Annexin-V negative/TO-PRO-3 negative). The in-process banking did not have negative effects on end-of-culture (Day 35) yield loss. The final cell yield between either Day 9 or 14 post-thaw and "fresh" conditions are comparable, with either HS-AB or HS-AB as the serum source.

The phenotypic profiles of maturing NK cells at Day 21/28/35 time points were found to be quite comparable between the "Fresh" and "Post-Thaw" culture, respectively. The phenotypic purity (CD56$^+$CD3$^-$) was found to be comparable as well. The expression of certain NK functional markers (CD94, NKG2D) were slightly different due to run-to-run variabilities.

In the K562 cytotoxicity assay, the Day 9/14 post-thaw cultured NK cells were found to yield ~0-20% lower specific K562 lysis readout comparing to non in-process cryopreserved cultured NK cells. However, given the expression levels of surface markers relevant to NK cytotoxic function (DNAM1, NKp46, NKG2D, etc.) were not concurrently reduced, the trend would need to be confirmed with additional donors and assay repeats. Overall, in-process cryopreservation at Day 9/14 of cultivation had minimal impact on process outcome.

7.14. Example 14: Development of Post-thaw Medium for NK Cell Dosing

This example demonstrates the development of post-thaw medium for NK cell dosing in animals. The effects of injection media and cell density were tested on NK cell's viablilty, cytotoxicity, cell recovery and clump formation. Viability was assessed by trypan blue staining; cytotoxicity was assessed by FACS (10:1 ratio of NK:K562) and clump formulation was assessed by microscopic assay. Results are shown in Tables 9-12 for the various types of injection media and cell density.

TABLE 9

Cell recovery, viability, cytotoxicity and clump formation of specific conditions tested
Thawing media: RPMI + 10%FBS;
Injection media: PBS + 1%FBS;
Cell density: $10 \times 10^6$ cells/ml

|  | 0 hr | 1 hr | 2 hr | 3 hr | 4 hr |
|---|---|---|---|---|---|
| Cell Recovery |  |  | 98.8% |  |  |
| Viability | 74.3% | 69.0% | 66.1% | 63.3% | 62.4% |
| Cytotoxicity |  | 60.3% |  | 44.3% |  |
| Clumping |  |  | None |  |  |

TABLE 10

Cell recovery, viability, cytotoxicity and clump formation of specific conditions tested
Thawing media: RPMI + 10%FBS;
Injection media: PBS + 1%FBS;
Cell density: $30 \times 10^6$ cells/ml

|  | 0 hr | 1 hr | 2 hr | 3 hr | 4 hr |
|---|---|---|---|---|---|
| Cell Recovery |  |  | 98.8% |  |  |
| Viability (%) | 74.3% | 69.8% | 66.5% | 64.0% | 63.6% |
| Cytotoxicity (%) |  | 51.8% |  | 37.9% |  |
| Clumping |  |  | None |  |  |

TABLE 11

Cell recovery, viability, cytotoxicity and clump formation of specific conditions tested
Thawing media: RPMI + 10%FBS;
Injection media: Plasmalyte + 1%HSA;
Cell density: $10 \times 10^6$ cells/ml

|  | 0 hr | 1 hr | 2 hr | 3 hr | 4 hr |
|---|---|---|---|---|---|
| Cell Recovery |  |  | 98.8% |  |  |
| Viability | 74.9% | 76.3% | 72.0% | 70.5% | 69.4% |
| Cytotoxicity |  | 59.4% |  | 51.3% |  |
| Clumping |  |  | None |  |  |

TABLE 12

Cell recovery, viability, cytotoxicity and clump formation of specific conditions tested
Thawing media: RPMI + 10%FBS;
Injection media: Plasmalyte + 1%HSA;
Cell density: $30 \times 10^6$ cells/ml

|  | 0 hr | 1 hr | 2 hr | 3 hr | 4 hr |
|---|---|---|---|---|---|
| Cell Recovery |  |  | 98.8% |  |  |
| Viability | 74.9% | 74.7% | 71.2% | 70.3% | 69.9% |
| Cytotoxicity |  | 61.2% |  | 53.9% |  |
| Clumping |  |  | None |  |  |

The results showed that the Plasmalyte+1% HSA injection media maintained NK cells with better viability and cytotoxicity than PBS+1% FBS injection media. Cytotoxicity also decreased over time after the cells were suspended in injection media. There was no cell density effect observed on viability and cytotoxicity when cells were suspended in Plasmalyte+1% HSA. NK cells also settled down in PBS+1% FBS or Plasmalyte+1% HSA media after 1 hour; however, cells did not appear to aggregate. Finally, there was no obvious loss of cell recovery and viability observed from the freezing-thawing process.

7.15. Example 16: Development of Post-thaw Medium for NK Cell Dosing

The effects of various HSA concentrations were also tested on the NK cell's viability, cytotoxicity, cell recovery and clump formation. The same methods were utilized from Example 19. Results are shown in Tables 14-16 for the various types of injection media and cell density.

TABLE 13

Cell recovery, viability, cytotoxicity and clump
formation of specific conditions tested
Thawing media: RPMI + 10%FBS;
Injection media: Plasmalyte + 1%HSA;
Cell density: 10 × 10$^6$ cells/ml

|  | 0 hr | 1 hr | 2 hr | 3 hr | 4 hr |
|---|---|---|---|---|---|
| Cell Recovery |  |  | 82.0% |  |  |
| Viability | 75.6% | 75.3% | 74.5% | 71.8% | 71.5% |
| Cytotoxicity |  | 64.4% |  | 35.5% |  |
| Clumping |  |  | None |  |  |

TABLE 14

Cell recovery, viability, cytotoxicity and clump
formation of specific conditions tested
Thawing media: Plasmalyte + 1%HSA;
Injection media: Plasmalyte + 1%HSA;
Cell density: 10 × 10$^6$ cells/ml

|  | 0 hr | 1 hr | 2 hr | 3 hr | 4 hr |
|---|---|---|---|---|---|
| Cell Recovery |  |  | 102.4% |  |  |
| Viability (%) | 77.1% | 77.5% | 71.2% | 72.4% | 75.1% |
| Cytotoxicity (%) |  | 61.48% |  | 31.7% |  |
| Clumping |  |  | None |  |  |

TABLE 15

Cell recovery, viability, cytotoxicity and clump
formation of specific conditions tested
Thawing media: Plasmalyte + 2.5%HSA;
Injection media: Plasmalyte + 2.5%HSA;
Cell density: 10 × 10$^6$ cells/ml

|  | 0 hr | 1 hr | 2 hr | 3 hr | 4 hr |
|---|---|---|---|---|---|
| Cell Recovery |  |  | 91.6% |  |  |
| Viability | 83.9% | 82.6% | 78.9.0% | 79.0% | 79.3% |
| Cytotoxicity |  | 71.7% |  | 46.8% |  |
| Clumping |  |  | None |  |  |

TABLE 16

Cell recovery, viability, cytotoxicity and clump
formation of specific conditions tested
Thawing media: Plasmalyte + 5%HSA;
Injection media: Plasmalyte + 5%HSA;
Cell density: 10 × 10$^6$ cells/ml

|  | 0 hr | 1 hr | 2 hr | 3 hr | 4 hr |
|---|---|---|---|---|---|
| Cell Recovery |  |  | 81.2% |  |  |
| Viability | 81.8% | 80.7% | 78.2% | 78.3% | 78.6% |
| Cytotoxicity |  | 64.8% |  | 55.1% |  |
| Clumping |  |  | None |  |  |

The results show that viability was maintained well over 4 hour post-thaw in all three injection media tested. Also, cytotoxicity decreased over time in all three injection media. However, the level of reduction was smaller in higher concentrations of HSA whereas Plasmalyte+5% HSA maintained the highest cytotoxicity. It was also observed that NK cells did not aggregate in all three injection media. Overall, Plasmalyte appears to be a better injection medium candidate than PBS.

7.16. Example 17: Cultivation of NK Cells without IL-2

This example demonstrates cultivation of NK cells in the absence of IL-2. Cell culture was performed by the two-stage process described in Example 11. Five different concentration of IL-2 in the first medium was tested: 0, 200, 500, 1000, 2000 U/mL.

The results indicate that developing NK cells in culture did not appear to respond to IL-2 on growth. The putiry of NK cells did not appear to depend on IL-2: the NK cells differentiate into CD56$^+$CD3$^-$ phenotype in the absence of IL-2. The combination of IL-7, IL-15 and SCF appeared to be sufficient for in vitro NK cell development.

Equivalents:

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes. The citation of any publication is for its disclosure prior to the filing date and should not be construed as an admission that the present invention is not entitled to antedate such publication by virtue of prior invention.

What is claimed is:

1. A method of producing a population of activated natural killer (NK) cells, comprising:
    (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, and wherein the first medium further comprises one or more of Fms-like-tyrosine kinase 3 ligand (Flt3-L), thrombopoietin (Tpo), interleukin-2 (IL-2), or heparin, such that the population expands, and a plurality of hematopoietic stem or progenitor cells within said population of hematopoietic stem or progenitor cells differentiate into NK cells during said expanding; and
    (b) next expanding the NK cells from step (a) in a second medium comprising interleukin-2 (IL-2), to produce a population of activated NK cells.

2. The method of claim 1, wherein the first medium further comprises fetal bovine serum or human serum.

3. The method of claim 1, wherein the SCF is present at a concentration of about 1 to about 150 ng/mL in the first medium.

4. The method of claim 1, wherein the Flt3-L is present at a concentration of about 1 to about 150 ng/mL in the first medium.

5. The method of claim 1, wherein the IL-2 is present at a concentration of about 50 to about 1500 IU/mL in the first medium.

6. The method of claim 1, wherein the IL-7 is present at a concentration of about 1 to about 150 ng/mL in the first medium.

7. The method of claim 1, wherein the IL-15 is present at a concentration of about 1 to about 150 ng/mL in the first medium.

8. The method of claim 1, wherein the Tpo is present at a concentration of about 1 to about 150 ng/mL in the first medium.

9. The method of claim 1, wherein the heparin is present at a concentration of about 0.1 to about 30 U/mL in the first medium.

10. The method of claim 1, wherein said IL-2 in the second step is present at a concentration of about 50 to about 1500 IU/mL in the second medium.

11. The method of claim 1, wherein said second medium additionally comprises one or more of fetal calf serum (FCS), transferrin, insulin, ethanolamine, oleic acid, linoleic acid, palmitic acid, bovine serum albumin (BSA) and phytohemagglutinin.

12. The method of claim 1, wherein the hematopoietic stem or progenitor cells are $CD34^+$.

13. The method of claim 1, wherein the hematopoietic stem or progenitor cells comprise hematopoietic stem or progenitor cells from human placental perfusate and hematopoietic stem or progenitor cells from umbilical cord, wherein said placental perfusate and said umbilical cord blood are from the same placenta.

14. The method of claim 1, wherein the NK cells are $CD3^-CD56^+CD16^-$.

15. The method of claim 14, wherein the NK cells are additionally $CD94^+CD117^+$.

16. The method of claim 14, wherein the NK cells are additionally $CD161^-$.

17. The method of claim 14, wherein the NK cells are additionally $NKG2D^+$.

18. The method of claim 14, wherein the NK cells are additionally $NKp46^+$.

19. The method of claim 14, wherein the NK cells are additionally $CD226^+$.

20. A population of activated NK cells obtained by a method comprising:
   (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, and wherein the first medium further comprises one or more of Fms-like-tyrosine kinase 3 ligand (Flt3-L), thrombopoietin (Tpo), interleukin-2 (IL-2), or heparin, such that the population expands, and a plurality of hematopoietic stem or progenitor cells within said population of hematopoietic stem or progenitor cells differentiate into NK cells during said expanding; and
   (b) next expanding the NK cells from step (a) in a second medium comprising interleukin-2 (IL-2), to produce a population of activated NK cells.

21. The population of claim 20, wherein the NK cells are $CD3^-CD56^+CD16^-$.

22. The population of claim 21, wherein the NK cells are additionally $CD94^+CD117^+$.

23. The population of claim 21, wherein the NK cells are additionally $CD161^-$.

24. The population of claim 21, wherein the NK cells are additionally $NKG2D^+$.

25. The population of claim 21, wherein the NK cells are additionally $NKp46^+$.

26. The population of claim 21, wherein the NK cells are additionally $CD226^+$.

* * * * *